(12) United States Patent
Schmidhammer et al.

(10) Patent No.: US 7,655,671 B2
(45) Date of Patent: *Feb. 2, 2010

(54) MORPHINAN DERIVATIVES, THE QUATERNARY AMMONIUM SALTS THEREOF SUBSTITUTED IN POSITION 14, METHOD FOR PRODUCTION AND USE THEREOF

(75) Inventors: Helmut Schmidhammer, Innsbruck (AT); Mariana Spetea, Innsbruck (AT); Johannes Schutz, Innsbruck (AT); Elisabeth Greiner, Patsch (AT); Falko Schüllner, Mils (AT); Bettina Sailer, Innsbruck (AT); Kurt Stübegger, Innsbruck (AT)

(73) Assignee: Alcasynn Pharmaceuticals GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 11/899,585

(22) Filed: Sep. 6, 2007

(65) Prior Publication Data

US 2008/0064712 A1    Mar. 13, 2008

Related U.S. Application Data

(63) Continuation of application No. 10/519,388, filed as application No. PCT/EP03/06866 on Jun. 27, 2003.

(30) Foreign Application Priority Data

Jul. 3, 2002   (DE)   ................................ 102 29 842

(51) Int. Cl.
   A61K 31/485   (2006.01)
   C07D 489/08   (2006.01)
(52) U.S. Cl. ........................... 514/282; 546/45; 546/44
(58) Field of Classification Search ................ 514/282; 546/45, 44
   See application file for complete search history.

(56) References Cited

U.S. PATENT DOCUMENTS

| | | | |
|---|---|---|---|
| 4,176,186 A | 11/1979 | Goldberg et al. | |
| 4,272,540 A | 6/1981 | Razdan et al. | |
| 4,390,699 A | 6/1983 | Brossi et al. | |
| 4,912,114 A | 3/1990 | Revesz | |
| 6,136,817 A * | 10/2000 | Schmidhammer | 514/279 |

FOREIGN PATENT DOCUMENTS

| | | |
|---|---|---|
| DE | 3412727 A1 | 10/1985 |
| EP | 0 030 685 A2 | 6/1981 |
| EP | 0 250 796 | 1/1988 |
| GB | 1300419 | 12/1972 |
| WO | WO2004/005294 A2 | 1/2004 |

OTHER PUBLICATIONS

Chen-Yu Cheng, et al., "*N*-Cubylmethyl Substituted Morphinoids as Novel Narcotic Antagonists", *Bioorganic & Medicinal Chemistry*, vol. 4, No. 1, pp. 73-80, 1996.

A. Coop, et al., "Delta Opioid Binding Selectivity of 3-Ether Analogs of Naltrindole", *Bioorganic & Medicinal Chemistry Letters*, 9 (1999) 3435-3438.

J. Schütz, et al., "Synthesis and Biological Evaluation of 14-Alkoxymorphinans. 17. Highly δ Opioid Receptor Selective 14-Alkoxy-Substituted Indolo- and Benzofuromorphinans", *J. Med. Chem.* 2002, 45, 5378-5383.

H. Schmidhammer, et al., "Synthesis and Biological Evaluation of 14- Alkoxymorphinans. 1. Highly Potent Opioid Agonists in the Series of(-)—14 Methoxy*N*-methylmorphinan-6-ones", *J. Med. Chem.*, 1964, 27, 1575-1579.

P. Klein, et al., "$O^3$-(2-Carbomethoxyallyl) Ethers of Opioid Ligands Derived from Oxymorphone, Naltrexone, Etorphine, Diprenorphine, Norbinaltorphimine, and Naltrindole. Unexpected $O^3$-Dealkylation in the Opioid Radioligand Displacement Assay", *J. Med. Chem.*, 1992, 35, 4589-4594.

P.S. Portoghese, et al., "Synthesis of Naltrexone-Dervied δ-Opioid Antagonists. Role of Conformation of the δ Address Moiety", *J. Med. Chem.*, 1994, 37, 579-585.

C. W. Funke, et al., "A $^1$H and $^{13}$C Nuclear Magnetic Resonance Study of Three Quaternary Salts of Naloxone and Qxymorphone", *J. Chem. Soc. Perkin Trans. II*, 1986, pp. 735-738.

"Synthesis of 14-alkoxymorphinan-6-ones (starting from Naltrexon) as Potential δ-opioid Receptor Antagonists", Thesis for the Degree of Ph.D. in Natural Sciences of the Leopold-Franzens University of Innsbruck, Submitted by Mag. Pharm. Roland Krassnig, Innsbruck 1994.

* cited by examiner

*Primary Examiner*—Charanjit S Aulakh
(74) *Attorney, Agent, or Firm*—Cohen Pontani Lieberman & Pavane LLP

(57) ABSTRACT

The present invention relates to a class of morphinan compounds and quaternary ammonium salts thereof, substituted in Position 14, which may be used as highly active analgesics or also as opioid antagonists. The present invention also relates to the pharmaceutically acceptable salts and easily produced derivatives thereof, a process for the production thereof and use thereof in the production of pharmaceutical specialities.

14 Claims, No Drawings

MORPHINAN DERIVATIVES, THE QUATERNARY AMMONIUM SALTS THEREOF SUBSTITUTED IN POSITION 14, METHOD FOR PRODUCTION AND USE THEREOF

CROSS REFERENCE TO RELATED APPLICATIONS

This application is a Continuation of patent application Ser. No. 10/519,388, filed Mar. 17, 2005, which is a National Phase of PCT/EP2003/006866 filed Jun. 27, 2003 which claims priority from German Application No. 102 29 842.4 filed in Germany on Jul. 3, 2002. The disclosures of these applications are incorporated herein by reference.

The present invention relates to a class of morphinan compounds and the quaternary salts thereof substituted in Position 14, which may be used as highly active analgesics or also as opioid antagonists. The present invention further relates to pharmaceutically acceptable salts and easily-produced derivatives thereof, a process of production thereof and use thereof in the production of pharmaceutical specialities.

The existence of opioid receptors as receptors of the central nervous system (CNS), which impart analgesic effects, has been clearly proven. These receptors are subdivided into three subtypes, μ, κ and δ. Activation of these receptors by opioid agonists leads to an analgesic effect. The activation of the μ-receptors causes the highest analgesic effect, whereby particularly N-methyl substituted morphinans with an oxygen function in Position 6 (morphine, oxymorphone, hydromorphone, etc.) are particularly active opioid agonists and are used as effective analgesics. In the past a great deal of work has been invested in structure-activity relationship studies of this class of substance.

In the Journal of Medicinal Chemistry 1984, 27, pp. 1575-1579 various 14-methoxy-N-methylmorphinan-6-ones are described with various substituents in Position 3. These derivatives show higher analgesic activity than their 14-hydroxy analogues.

A detailed study of 5-methyloxymorphone (=14-hydroxy-5-methyldihydromorphinone) is described in Helvetica Chimica Acta (1988, 71, pp. 1801-1804), which arrives at the result that the introduction of a 5-methyl group reduces the opioid agonistic properties of oxymorphone.

A further study of 14-alkoxy-N-methylmorphinan-6-ones is described in Helvetica Chimica Acta 1989, 72, pp. 1233-1239, in which the influence of various substituents in Position 3 and of the amino nitrogen have been evaluated.

The German published patent application DE 34 12 727 describes 14-alkoxy-N-methylmorphinan-6-ones (14-O-alkyloxymorphones) with higher activity than their 14-hydroxy analogues.

If instead of the N-methyl group, e.g. an N-cyclopropylmethyl group, an N-allyl group or an N-tetrahydrofurfuryl group is introduced, then normally compounds result which cause antagonistic effects on opioid receptors (see Prog. Med. Chem. 1998, 35, 83-132). Such opioid antagonists cancel both the analgesic effect as well as the side effects of opioid agonists (e.g. respiratory depression or obstipation).

Surprisingly, it has now been found that e.g. N-cyclopropylmethyl, N-allyl or N-tetrahydrofurfuryl substituted morphinan-6-ones with arylalkyl substituents or longer chained alkyl substituents in Position 14 are highly active opioid agonists with excellent analgesic activity. The very high analgesic activity enables low dosing, which leads to a lower rate of side effects.

Furthermore, its has been surprisingly found that a quaternisation of morphinan-6-ones, which exhibit arylalkyl substituents or alkyl substituents in Position 14, on one hand leads to substances with higher analgesic activity, but on the other hand to substances with excellent opioid antagonism. The previously described quaternisation of 14-hydroxymorphinan-6-ones (e.g. oxymorphone or naloxone) led to a significant weakening of the effectiveness (see M. A. Iorio et al., Eur. J. Med. Chem.—Chim. Ther. 1984, 19, 301-303). Furthermore, it has been found that these new substances develop their effect primarily in the periphery, because they cannot, or can only to a slight extent, overcome the blood-brain barrier.

The present invention provides highly active compounds of the formulae (I), (Ia), (IA) and (IAa) as defined in the Claims 1 and 2. Preferred embodiments are given in the subclaims, along with further aspects of this invention, such as compositions and uses. The statements made, in particular in conjunction with the compounds, about preferred embodiments apply analogously also to the other aspects of the invention, such as the compositions and uses.

Additional preferred embodiments are defined in the following.

Compounds of the formulae (I) and (Ia), in which the substituents have the following significance:

$R_1$: $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$ and alkyl is $C_1$-$C_6$; $C_5$-$C_{16}$-cycloalkylalkenyl, where cycloalkyl is $C_3$-$C_{10}$ and alkenyl is $C_2$-$C_6$; $C_5$-$C_{16}$-cycloalkylalkinyl, where cycloalkyl is $C_3$-$C_{10}$ and alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl;

$R_2$: subject to the following definition of X, $C_4$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$ and alkyl is $C_1$-$C_6$; $C_5$-$C_{16}$-cycloalkylalkenyl, where cycloalkyl is $C_3$-$C_{10}$ and alkenyl is $C_2$-$C_6$; $C_5$-$C_{16}$-cycloalkylalkinyl, where cycloalkyl is $C_3$-$C_{10}$ and alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-aklinyl; $C_3$-$C_6$-alkenoyl; $C_3$-$C_6$-alkinoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl;

$R_3$: hydrogen; $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$.

$R_4$: hydrogen; hydroxy; $C_1$-$C_6$-alkyloxy; $C_2$-$C_{10}$-alkyloxyalkoxy, where alkyloxy is $C_1$-$C_4$ and alkoxy is $C_1$-$C_6$-alkyloxy $C_1$-$C_6$-alkyloxy; $C_2$-$C_6$-alkenyloxy; $C_2$-$C_6$-alkinyloxy; $C_4$-$C_{16}$-cycloalkylalkyloxy, where cycloalkyl is $C_3$-$C_{10}$ and alkyl is $C_1$-$C_6$; $C_5$-$C_{16}$-cycloalkylalkenyloxy, where cycloalkyl is $C_3$-$C_{10}$ and alkenyl is $C_2$-$C_6$; $C_5$-$C_{16}$-cycloalkylalkinyloxy, where cycloalkyl is $C_3$-$C_{10}$ and alkinyl is $C_2$-$C_6$; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_1$-$C_6$-alkenoyloxy; $C_1$-$C_6$-alkinoyloxy; $C_7$-$C_{16}$-arylalkanoyloxy, where aryl is $C_6$-$C_{10}$-aryl and alkanoyloxy is $C_1$-$C_6$-alkylanoyloxy; $C_9$-$C_{16}$-arylalkenoyloxy, where aryl is $C_6$-$C_{10}$-aryl and alkenoyloxy is $C_3$-$C_6$- alkenoyloxy; $C_7$-$C_{16}$-arylalkinoyloxy, where aryl is $C_6$-$C_{10}$-aryl and alkinoyloxy is $C_3$-$C_6$-alkinoyloxy;

$R_5$: hydrogen; hydroxy; $C_1$-$C_6$-alkyloxy; $C_2$-$C_{10}$-alkyloxyalkoxy, where alkyloxy is $C_1$-$C_4$ and alkoxy is $C_1$-$C_6$-alkyloxy $C_1$-$C_6$-alkyloxy; $C_2$-$C_6$-alkenyloxy; $C_2$-$C_6$-alkinyloxy; $C_4$-$C_{16}$-cycloalkylalkyloxy, where cycloalkyl is $C_3$-$C_{10}$ and alkyl is $C_1$-$C_6$; $C_5$-$C_{16}$-cycloalkylalkenyloxy, where cycloalkyl is $C_3$-$C_{10}$ and alkenyl is $C_2$-$C_6$; $C_5$-$C_{16}$-cycloalkylalkinyloxy, where cycloalkyl is $C_3$-$C_{10}$ and alkinyl is $C_2$-$C_6$; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_7$-$C_{16}$-arylalkanoyloxy, where aryl is $C_6$-$C_{10}$-aryl and alkanoyloxy is $C_1$-$C_6$-alkylanoyloxy;

X is oxygen, sulphur or methylene.

In the present invention alkyl, alkenyl and alkinyl consist of branched or unbranched alkyl, alkenyl and alkinyl.

Aryl can be unsubstituted or mono-, di- or trisubstituted independently with hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)_2$, $CO(C_1$-$C_3$-alkyl); amino; $(C_1$-$C_3$-monoalkyl) amino, $(C_1$-$C_3$-dialkyl)amino; $C_5$-$C_6$-cycloalkylamino, $(C_1$-$C_3$-alkanoyl)amido, SH, $SO_3H$, $SO_3(C_1$-$C_3$-alkyl), $SO_2(C_1$-$C_3$-alkyl), $SO(C_1$-$C_3$-alkyl)$, $C_1$-$C_3$-alkylthio or $C_1$-$C_3$-alkanoylthio.

The above stated definitions for alkyl, alkenyl, alkinyl and aryl apply to all substituents of this application.

If the (cyclical saturated group) contains heteroatoms, then there are preferably 1 to 3 heteroatoms, in particular 1 or 2 and most preferably one heteroatom, preferably selected from O, S, N, P and B and more preferably from O, S and N.

In the formulae (IA) and (IAa) the substituents preferably have the following significance:

$R_1$: $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$ and alkyl is $C_1$-$C_6$; $C_5$-$C_{16}$-cycloalkylalkenyl, where cycloalkyl is $C_3$-$C_{10}$ and alkenyl is $C_2$-$C_6$; $C_5$-$C_{16}$-cycloalkylalkinyl, where cycloalkyl is $C_3$-$C_{10}$ and alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl;

The two substituents $R_1$ can be the same or different;

$R_2$: subject to the following definition of X, $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$ and alkyl is $C_1$-$C_6$; $C_5$-$C_{16}$-cycloalkylalkenyl, where cycloalkyl is $C_3$-$C_{10}$ and alkenyl is $C_2$-$C_6$; $C_5$-$C_{16}$-cycloalkylalkinyl, where cycloalkyl is $C_3$-$C_{10}$ and alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_1$-$C_6$-alkanoyl; $C_3$-$C_6$-alkenoyl: $C_3$-$C_6$-alkinoyl; $C_7$-$C_{16}$-arylalkanoyl, where aryl is $C_6$-$C_{10}$-aryl and alkanoyl is $C_1$-$C_6$-alkyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl;

$R_3$: hydrogen; $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$.

$R_4$: hydrogen; hydroxy; $C_1$-$C_6$-alkyloxy; $C_2$-$C_{10}$-alkyloxyalkoxy, where alkyloxy is $C_1$-$C_4$ and alkoxy is $C_1$-$C_6$-alkyloxy $C_1$-$C_6$-alkyloxy; $C_2$-$C_6$-alkenyloxy; $C_2$-$C_6$-alkinyloxy; $C_4$-$C_{16}$-cycloalkylalkyloxy, where cycloalkyl is $C_3$-$C_{10}$ and alkyl is $C_1$-$C_6$; $C_5$-$C_{16}$-cycloalkylalkenyloxy, where cycloalkyl is $C_3$-$C_{10}$ and alkenyl is $C_2$-$C_6$; $C_5$-$C_{16}$-cycloalkylalkinyloxy, where cycloalkyl is $C_3$-$C_{10}$ and alkinyl is $C_2$-$C_6$; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_1$-$C_6$-alkenoyloxy; $C_1$-$C_6$-alkinoyloxy; $C_7$-$C_{16}$-arylalkanoyloxy, where aryl is $C_6$-$C_{10}$-aryl and alkanoyloxy is $C_1$-$C_6$-alkylanoyloxy; $C_9$-$C_{16}$-arylalkenoyloxy, where aryl is $C_6$-$C_{10}$-aryl and alkenoyloxy is $C_3$-$C_6$-alkenoyloxy; $C_7$-$C_{16}$-arylalkinoyloxy, where aryl is $C_6$-$C_{10}$-aryl and alkinoyloxy is $C_3$-$C_6$-alkinoyloxy;

$R_5$: hydrogen; hydroxy; $C_1$-$C_6$-alkyloxy; $C_2$-$C_{10}$-alkyloxyalkoxy, where alkyloxy is $C_1$-$C_4$ and alkoxy is $C_1$-$C_6$-alkyloxy $C_1$-$C_6$-alkyloxy; $C_2$-$C_6$-alkenyloxy; $C_2$-$C_6$-alkinyloxy; $C_4$-$C_{16}$-cycloalkylalkyloxy, where cycloalkyl is $C_3$-$C_{10}$ and alkyl is $C_1$-$C_6$; $C_5$-$C_{16}$-cycloalkylalkenyloxy, where cycloalkyl is $C_3$-$C_{10}$ and alkenyl is $C_2$-$C_6$; $C_5$-$C_{16}$-cycloalkylalkinyloxy, where cycloalkyl is $C_3$-$C_{10}$ and alkinyl is $C_2$-$C_6$; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_7$-$C_{16}$-arylalkanoyloxy, where aryl is $C_6$-$C_{10}$-aryl and alkanoyloxy is $C_1$-$C_6$-alkylanoyloxy;

X is oxygen, sulphur or methylene.

In this invention alkyl, alkenyl and alkinyl consist of branched or unbranched alkyl, alkenyl and alkinyl.

Aryl can be unsubstituted or mono-, di- or trisubstituted independently with hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)_2$, $CO(C_1$-$C_3$-alkyl); amino; $(C_1$-$C_3$-monoalkyl) amino, $(C_1$-$C_3$-dialkyl)amino; $C_5$-$C_6$-cycloalkylamino; $(C_1$-$C_3$-alkanoyl)amido, SH, $SO_3H$, $SO_3(C_1$-$C_3$-alkyl), $SO_2(C_1$-$C_3$-alkyl), $SO(C_1$-$C_3$-alkyl), $C_1$-$C_3$-alkylthio or $C_1$-$C_3$-alkanoylthio.

The above stated definitions for alkyl, alkenyl, alkinyl and aryl apply to all substituents of this application.

If the (cyclical saturated group) contains heteroatoms, then there are preferably 1 to 3 heteroatoms, in particular 1 or 2 and most preferably one heteroatom, preferably selected from O, S, N, P and B and more preferably from O, S and N.

The compounds of this invention comprise also pharmaceutically and pharmacologically acceptable salts of the compounds of the formula (I). According to this invention both inorganic and also organic salts are suitable. Examples of suitable inorganic salts for this invention are hydrochlorides, hydrobromides, sulphates and phosphates. Possible organic salts are for example methane sulphonates, salicylates, fumarates, maleinates, succinates, aspartates, citrates, oxalates and orotates.

In a preferred representation of the formula (I) or (Ia), when X is oxygen, $R_1$ is $C_1$-$C_6$-alkyl; $C_2$-$C_6$-alkenyl; $C_4$-$C_{16}$-cycloalkylalkyl, where cycloalkyl is $C_3$-$C_{10}$ and alkyl is $C_1$-$C_6$; $C_7$-$C_{16}$-arylalkyl, where aryl is $C_6$-aryl and alkyl is $C_1$-$C_3$-alkyl; $R_2$ is $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $R_3$ is hydrogen or methyl; $R_4$ is hydroxy, methoxy or acetoxy.

Strongly preferred compounds, in which X is oxygen, are those in which $R_1$ to $R_4$ are as follows (wherein these compounds can be present as free bases/acids or as acceptable salt):

R₁: methyl, ethyl, propyl, butyl, pentyl, hexyl, in particular methyl, ethyl, propyl and most preferred methyl R₂: phenylmethylene (in the examples the notation phenylmethyl is used), phenylethylene, phenylpropylene, phenylbutylene, phenylpentylene, phenylhexylene, whereby the phenyl core can be optionally substituted, in particular phenylpropylene (in the examples this radical is also termed phenylpropyl)

R₃: methyl, ethyl, propyl, butyl, pentyl, hexyl, in particular methyl, ethyl, propyl and most preferred methyl R₄: OH, methoxy, acetoxy, in particular OH One example of a particularly preferred compound is 4,5α-epoxy-3-hydroxy-5β,17-dimethyl-14β-[(3-phenylpropyl)oxy]morphinan-6-one, in particular the hydrochloride and the hydrobromide.

In a particularly preferred representation of this invention the compound is selected from:

17-allyl-4,5α-epoxy-3-methoxy-14β-(3-phenylpropyloxy)morphinan-6-one 17-allyl-4,5α-epoxy-3-hydroxy-14β-(3-phenylpropyloxy)morphinan-6-one 17-allyl-4,5α-epoxy-3-methoxy-5β-methyl-14β-(3-phenylpropyloxy)morphinan-6-one 17-allyl-4,5α-epoxy-3-hydroxy-5β-methyl-14β-(3-phenylpropyloxy)morphinan-6-one 17-cyclobutylmethyl-4,5α-epoxy-3-methoxy-14β-(3-phenylpropyloxy)morphinan-6-one 17-cyclobutylmethyl-4,5α-epoxy-3-hydroxy-14β-(3-phenylpropyloxy)morphinan-6-one 17-cyclobutylmethyl-4,5α-epoxy-3-methoxy-5β-methyl-14β-(3-phenylpropyloxy)morphinan-6-one 17-cyclobutylmethyl-4,5α-epoxy-3-hydroxy-5β-methyl-14β-(3-phenylpropyloxy)morphinan-6-one 17-cyclopropylmethyl-4,5α-epoxy-3-methoxy-14β-(3-phenylpropyloxy)morphinan-6-one 17-cyclopropylmethyl-4,5α-epoxy-3-hydroxy-14β-(3-phenylpropyloxy)morphinan-6-one 17-cyclopropylmethyl-4,5α-epoxy-3-methoxy-5β-methyl-14β-(3-phenylpropyloxy)morphinan-6-one 17-cyclopropylmethyl-4,5α-epoxy-3-hydroxy-5β-methyl-14β-(3-phenylpropyloxy)morphinan-6-one 4,5α-epoxy-3-methoxy-5β,17-dimethyl-14β-[(3-phenylpropyl)oxy]morphinan-6-one 4,5α-epoxy-3-hydroxy-5β,17-dimethyl-14β-[(3-phenylpropyl)oxy)]morphinan-6-one 17-propyl-4,5α-epoxy-3-methoxy-14β-(3-phenylpropyloxy)morphinan-6-one 17-propyl-4,5α-epoxy-3-hydroxy-14β-(3-phenylpropyloxy)morphinan-6-one 17-propyl-4,5α-epoxy-3-methoxy-5β-methyl-14β-(3-phenylpropyloxy)morphinan-6-one 17-propyl-4,5α-epoxy-3-hydroxy-5β-methyl-14β-(3-phenylpropyloxy)morphinan-6-one 17-tetrahydrofurfuryl-4,5α-epoxy-3-methoxy-14β-(3-phenylpropyloxy)morphinan-6-one 17-tetrahydrofurfuryl-4,5α-epoxy-3-hydroxy-14β-(3-phenylpropyloxy)morphinan-6-one 17-tetrahydrofurfuryl-4,5α-epoxy-3-methoxy-5β-methyl-14β-(3-phenylpropyloxy)morphinan-6-one 17-tetrahydrofurfuryl-4,5α-epoxy-3-hydroxy-5β-methyl-14β-(3-phenylpropyloxy)morphinan-6-one 17-(2-phenylethyl)-4,5α-epoxy-3-methoxy-14β-(3-phenylpropyloxy)morphinan-6-one 17-(2-phenylethyl)-4,5α-epoxy-3-hydroxy-14β-(3-phenylpropyloxy)morphinan-6-one 17-(2-phenylethyl)-4,5α-epoxy-3-methoxy-5β-methyl-14β-(3-phenylpropyloxy)morphinan-6-one 17-(2-phenylethyl)-4,5α-epoxy-3-hydroxy-5β-methyl-14β-(3-phenylpropyloxy)morphinan-6-one 17-ethyl-4,5α-epoxy-3-methoxy-14β-(3-phenylpropyloxy)morphinan-6-one 17-ethyl-4,5α-epoxy-3-hydroxy-14β-(3-phenylpropyloxy)morphinan-6-one 17-ethyl-4,5α-epoxy-3-methoxy-5β-methyl-14β-(3-phenylpropyloxy)morphinan-6-one 17-ethyl-4,5α-epoxy-3-hydroxy-5β-methyl-14β-(3-phenylpropyloxy)morphinan-6-one 17-cyclopropylmethyl-4,5α-epoxy-3-hydroxy-14β-[(2-methylbenzyl)oxy]morphinan-6-one 14β-[(2-chlorobenzyl)oxy]-17-(cyclopropylmethyl)-4,5α-epoxy-3-hydroxymorphinan-6-one 14β-benzyloxy-17-cyclopropylmethyl-4,5α-epoxy-3-hydroxymorphinan-6-one 14β-butoxy-17-cyclopropylmethyl-4,5α-epoxy-3-hydroxymorphinan-6-one 17-cyclopropylmethyl-4,5α-epoxy-3-hydroxy-14β-[(3-methylbutyl)oxy]morphinan-6-one 4,5α-epoxy-5β,17-dimethyl-14β-[(3-phenylpropyl)oxy]-3-[(prop-2-inyl)oxy]morphinan-6-one 14β-[(3-chlorobenzyl)oxy]-4,5α-epoxy-17-methyl-3-[(prop-2-inyl)oxy]morphinan-6-one 4,5α-epoxy-17-ethyl-3-methoxy-14β-[(3-phenylpropyl)oxy]morphinan-6-one 4,5α-epoxy-17-ethyl-3-hydroxy-14β-[(3-phenylpropyl)oxy]morphinan-6-one 4,5α-epoxy-3-hydroxy-14β-[(3-methylbutyl)oxy]-17-propylmorphinan-6-one 5β-benzyl-14-methoxycodeinone(=5-benzyl-7,8-didehydro-4,5α-epoxy-3,14β-dimethoxy-17-methyl-morphinan-6-one)

5β-benzyl-4,5α-epoxy-3,14β-dimethoxy-17-methylmorphinan-6-one

5β-benzyl-4,5α-epoxy-3-hydroxy-14β-methoxy-17-methylmorphinan-6-one 4-hydroxy-3-methoxy-17-methyl-14-[(3-phenylpropyl)oxy]-morphinan-6-one 3,4-dimethoxy-17-methyl-14-[(3-phenylpropyl)oxy]-morphinan-6-one 14β-benzyloxy-4-hydroxy-3-methoxy-17-methylmorphinan-6-one 14β-benzyloxy-3,4-dimethoxy-17-methylmorphinan-6-one 4-hydroxy-3-methoxy-17-methyl-14β-[(2-naphthylmethyl)oxy]morphinan-6-one 3,4-dimethoxy-17-methyl-14β-[(2-naphthylmethyl)oxy]morphinan-6-one 4-hydroxy-3-methoxy-5β,17-dimethyl-14β-[(3-phenylpropyl)oxy]-morphinan-6-one 3,4-dimethoxy-5β,17-dimethyl-14β-[(3-phenylpropyl)oxy]-morphinan-6-one 14β-ethoxy-4-hydroxy-3-methoxy-5β,17-dimethylmorphinan-6-one 14β-ethoxy-3,4-dimethoxy-5β,17-dimethylmorphinan-6-one 14β-benzyloxy-3,4-dimethoxy-5β,17-dimethylmorphinan-6-one In a preferred representation of the formula (IA) or (IAa), when X is oxygen, $R_1$ is $C_1$-$C_6$-alkyl, $C_2$-$C_6$-alkenyl, $C_4$-$C_{16}$-cycloalkylalkyl, where cycloalkyl is $C_3$-$C_{10}$ and alkyl is $C_1$-$C_6$, $C_7$-$C_{16}$-arylalkyl, where aryl is $C_6$-aryl and alkyl is $C_1$-$C_3$-alkyl; $R_2$ is $C_1$-$C_6$-alkyl, $C_2$-$C_6$-alkenyl, $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $R_3$ is hydrogen or methyl; $R_4$ is hydroxy, methoxy or acetoxy.

In a particularly preferred representation of this invention is the compound selected from:

4,5α-epoxy-3-hydroxy-17,17-dimethyl-6-oxo-14β-[(3-phenylpropyl)oxy]morphinanium-iodide (17S)-4,5α-epoxy-17-ethyl-3-hydroxy-17-methyl-6-oxo-14β-[(3-phenylpropyl)oxy]morphinanium-iodide (17R)-4,5α-epoxy-3-hydroxy-17-methyl-6-oxo-14β-[(3-phenylpropyl)oxy]-17-[(2-R,S-tetrahydrofurfuran-2-yl)methyl]morphinanium-iodide (17R)-17-allyl-4,5α-epoxy-14β-ethoxy-3-hydroxy-17-methyl-6-oxomorphinanium-iodide (17R)-17-allyl-4,5α-epoxy-3-hydroxy-14β-methoxy-17-methyl-6-oxomorphinanium-iodide (17S)-17-allyl-4,5α-epoxy-3-hydroxy-14β-methoxy-17-methyl-6-oxomorphinanium-iodide 4,5α-epoxy-3-hydroxy-14β-methoxy-17,17-dimethyl-6-oxo-morphinanium-iodide 5β-benzyl-14β-(butyloxy)-4,5α-epoxy-3-hydroxy-17,17-dimethyl-6-oxomorphinanium-iodide (17S)-17-allyl-5β-benzyl-14β-butoxy-4,5α-epoxy-3-hydroxy-17-methyl-6-oxomorphinanium-iodide 14β-butoxy-4,5α-epoxy-3-hydroxy-17,17-dimethyl-6-oxo-morphinanium-iodide (17R)-17-cyclopropylmethyl-4,5α-epoxy-3-hydroxy-17-methyl-6-oxo-14β-[(3-phenylpropyl)oxy]morphinanium-iodide (17R)-17-cyclopropylmethyl-4,5α-epoxy-3-methoxy-17-methyl-6-oxo-14β-[(3-phenylpropyl)oxy]morphinanium-iodide (17R)-17-cyclopropylmethyl-4,5α-epoxy-3-hydroxy-17-methyl-6-oxo-14β-[(2-phenylbenzyl)oxy]morphinanium-iodide (17R)-14β-[(4-chlorobenzyl)oxy]-17-cyclopropylmethyl-4,5α-epoxy-3-hydroxy-17-methyl-6-oxomorphinanium-iodide 17(R)-4,5α-epoxy-3-hydroxy-14β-methoxy-17-methyl-6-oxo-17-(2-phenylethyl)morphinanium-iodide It has now been found that the compounds of the objective invention (morphinan compounds and their quaternary salts substituted in Position 14) represent effective opioid receptor ligands and exhibit a high therapeutic usage potential as analgesics, narcotics, as immunomodulators with immunostimulating or immunosuppressive effects, as cancer therapeutics, inflammation inhibitors, as antirheumatics, for the suppression of organ rejection after transplants, as diuretics, anorectics, as agents against diarrhoea, obstipation, ileus, pruritis, as anaesthetics or as neuroprotective active substances.

The compounds stated in the claims are therefore potentially usable for the treatment of acute and chronic pain, of functional intestinal diseases, such as diarrhoea, abdominal pain, obstipation, ileus, for the treatment of inflammatory intestinal diseases, for the treatment of mammals, especially human beings, for the treatment of the Raynaud syndrome, for the treatment of complaints caused by vasoconstriction, for the treatment of dysmenorrhoea, angina pectoris, cardiac infarction, emphysema, bronchial spasms, chronic obstructive bronchitis, rheumatic complaints, oedemas, nephrosis, nephritis in conjunction with rheumatic diseases, for the treatment of tumours, phaeochromocytome, the Addison disease, hepatic cirrhosis, chronic inflammations of the small and large intestines and rectum, for the treatment of pruritis, psoriasis, neurodermatitis, for addition withdrawal from for example opioids, cocaine or alcohol, for the treatment of overweight, or for the treatment of psychic diseases such as dysphoria, depression or schizophrenia.

Surprisingly it was also found that the compounds of this objective invention were not capable of overcoming the blood-brain barrier or only to a slight extent, and therefore a special significance could be attributed to them with regard to their use as peripherally effective therapeutics, for example as medicaments for the treatment of pain, for the treatment or prevention of obstipation caused by analgesics, for the treatment or prevention of postoperative ileus, postpartum ileus, for rheumatic therapy, for suppressing organ rejection after transplants with mammals, especially human beings, also for the treatment of erection problems. The limited access to the central nervous system goes with a very reduced side-effect rate, which is relevant to central side effects, such as for example nausea, vomiting, sedation, dizziness, confusion, respiratory depression and mania.

Production of the Compounds

The compounds according to this invention, which are represented by the formula (I) or (Ia), can be obtained with the aid of the following methods:

Starting from thebaine of the formula (II),

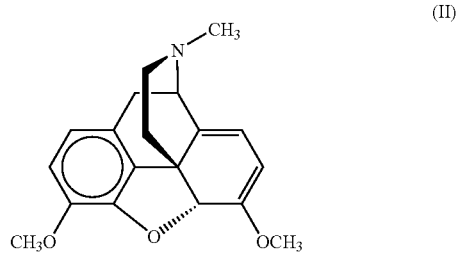

this compound is reacted with dialkylsulphates, fluorosulphonic acid alkylesters, alkylsulphonic acid alkylesters, arylsulphonic acid alkylesters, alkylhalogenides, aralkylhalogenides, alkylsulphonic acid aralkylesters, arylsulphonic acid aralkylesters, arylalkenylhalogenides, chloroformic acid esters or similar compounds in solvents such as tetrahydrofuran, 1,2-dimethoxyethane, diethylether or similar compounds in the presence of a strong base such as n-butyllithium, lithium diethylamide, lithium diisopropylamide or similar compounds at low temperatures (−20° C. to −80° C.) (see Boden et al., J. Org. Chem., Vol 47, pp. 1347-1349, 1982; Schmidhammer et al., Helv. Chim. Acta, Vol. 71, pp. 642-647, 1988; Gates et al., J. Org. Chem., Vol. 54, pp. 972-975, 1984) to obtain the compounds of formula (III), where $R_3$ is $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2$($C_1$-$C_6$-alkyl); $CO_2H$; $CH_2OH$.

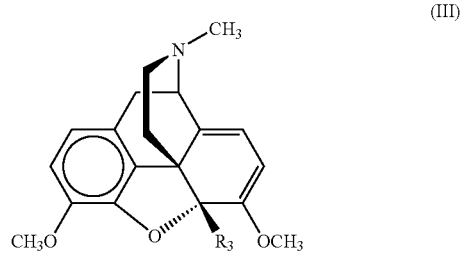

The compounds of formula (III) or thebaine (formula (II)) can be converted into the corresponding 14-hydroxycodeinones of formula (IV),

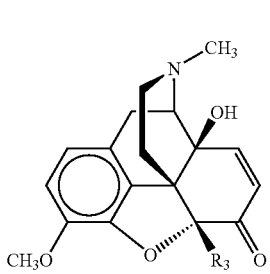

where $R_3$ represents hydrogen, $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl). This reaction is carried out with performic acid (see H. Schmidhammer et al., Helv. Chim. Acta, Vol. 71, 1801-1804, 1988), m-chloroperbenzoic acid or similar at temperatures between 0° C. and 60° C. The preferred method is the reaction with performic acid at 0° C. to 40° C.

These 14-hydroxycodeinones of formula (IV) are reacted in sequence with dialkylsulphates, alkylhalogenides, alkenylhalogenides, alkinylhalogenides, arylalkylhalogenides, arylalkenylhalogenides, arylalkinylhalogenides or chloroformates in solvents such as N,N-dimethylformamide (DMF) or tetrahydrofuran (THF) in the presence of a strong base such as sodium hydride, potassium hydride or sodium amide in order to obtain the compounds of formula (V),

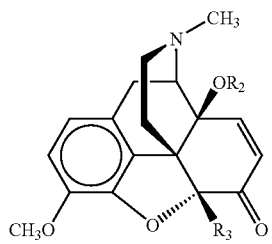

where $R_3$ is defined as above; and $R_2$ represents $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_1$-$C_6$-alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkanoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl.

These compounds are then reduced to compounds of formula (VI) using catalytic hydrogenation via a catalyst such as Pd/C, PdO, Pd/Al$_2$O$_3$, Pt/C, PtO$_2$, Pt/Al$_2$O$_3$ or similar in solvents such as alcohols, alcohol/water mixtures, glacial acetic acid or similar,

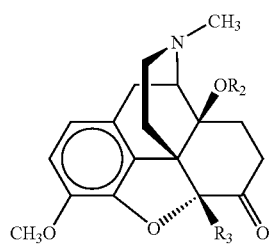

where $R_2$ and $R_3$ are defined as above.

The following N-demethylation is carried out with chloroformates or bromocyanogens in solvents such as 1,2-dichloromethane, chloroform or similar, and compounds of the formula (VII) are obtained,

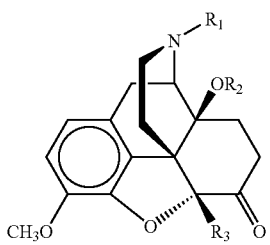

where $R_1$ represents $CO_2CH(Cl)CH_3$, $CO_2CH=CH_2$, $CO_2CH_2CCl_3$, $CO_2CH_2CH_3$, $CO_2Ph$, $CN$ or similar; and $R_2$ and $R_3$ are defined as above.

The carbamates of formula (VII) are split either by reflux heating in alcohols (in the case of 1-chloroethylcarbamates) or by the addition of hydrogen halogenides or halogens followed by reflux x heating in alcohols (in the case of vinylcarbamates) and the cyanamides of formula (VII) are obtained by acid or alkali hydrolysis, whereby N-Nor compounds of formula (VIII) are obtained,

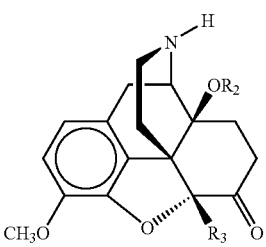

in which $R_2$ and $R_3$ are defined as above.

The N-alkylation of the compounds of formula (VIII) is achieved with alkylhalogenides, dialkylsulphates, alkenylhalogenides, alkinylhalogenides, cycloalkylalkylhalogenides, cycloalkenylalkylhalogenides, arylalkyl halogenides, arylalkenyl halogenides, arylalkinyl halogenides or similar in solvents such as dichloromethane, chloroform or N,N-dimethylformamide in the presence of a base such as sodium bicarbonate, potassium carbonate, triethylamine or similar and therefore compounds of the formula (IX) are obtained,

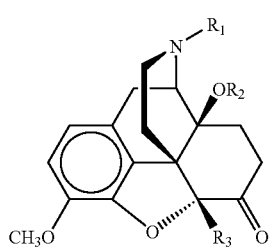

(IX)

where $R_2$ and $R_3$ are defined as above; and $R_1$ represents $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, whereby aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl.

Ether splitting of these compounds of the formula (IX) with boron tribromide (in a solvent such as dichloromethane or chloroform) at 0° C., 48% hydrobromic acid (reflux heating), with sodium alkanthiolates (in a solvent such as N,N-dimethylformamide) or with other generally well-known ether splitting reagents, gives phenolic compounds of the formula (X),

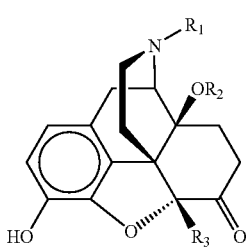

(X)

in which $R_1$, $R_2$ and $R_3$ are defined as above.

The 3-O alkylation of the compounds of formula (X) are achieved with alkylhalogenides, dialkylsulphates, alkenylhalogenides, alkinylhalogenides, cycloalkylalkylhalogenides, cycloalkylalkenylhalogenides, arylalkylhalogenides, arylalkenylhalogenides, arylalkinylhalogenides or similar in solvents such as dichloromethane, chloroform, acetone or N,N-dimethylformamide in the presence of a base such as sodium bicarbonate, potassium carbonate, triethylamine or similar; 3-O acylation of the compounds of the formula (X) is achieved with carboxylic acid halogenides, carboxylic acid anhydrides or similar in solvents such as dichloromethane, chloroform, acetone, N,N-dimethylformamide, pyridine or similar and therefore compounds of the formula (XI) are obtained;

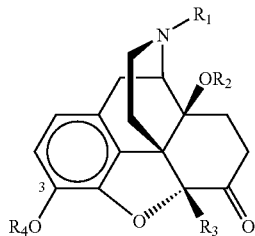

(XI)

where $R_1$, $R_2$ and $R_3$ are as defined above; $R_4$ represents $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_1$-$C_6$-alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl.

An alternative path starts with compounds of formula (XII), in which $R_1$ and $R_3$ are defined as above (see Weiss et al., J. Amer. Chem. Soc., Vol. 77, p. 5891, 1955; Iijima et al., J. Med. Chem., Vol. 21, pp. 398-400, 1978; Coop et al., J. Org. Chem., Vol. 63, pp. 4392-4396, 1998; Schmidhammer et al., Helv. Chim. Acta, Vol. 71, pp. 1801-1804, 1988; Schmidhammer et al., Helv. Chim. Acta, Vol. 73, pp. 1986-1990, 1990).

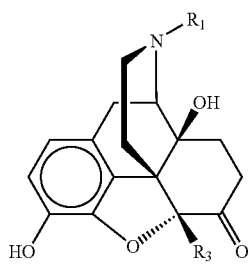

(XII)

The ketones of formula (XII) are reacted in the presence of methane sulphonic acid or similar with ethylene glycol (as reagent and solvent) to form the compounds of formula (XIII),

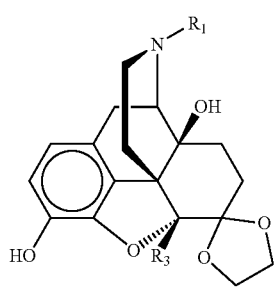

(XIII)

in which $R_1$ and $R_3$ are defined as above.

The introduction of a protective group such as for example benzyl, trityl or silyl to the 3-hydroxy group is achieved by 3-O-benzylation, 3-O-tritylation or 3-O-silylation of the compounds of the formula (XIII) with benzyl halogenides, trityl halogenides, trialkyl halogen silanes in solvents such as dichloromethane, chloroform, acetone or N,N-dimethylformamide in the presence of a base such as sodium bicarbonate, potassium carbonate, triethylamine or similar or by means of phase transfer catalysis and therefore compounds of the formula (XIV) are obtained,

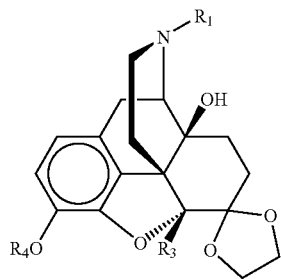

(XIV)

where $R_1$ and $R_3$ are defined as above; $R_4$ is a protective group such as benzyl, trityl, tri-($C_1$-$C_6$-alkyl)silyl or tris-($C_7$-$C_{16}$-arylalkyl)silyl or another easily split off protective group.

These 14-hydroxy compounds are following reacted with dialkylsulphates, alkylhalogenides, alkenylhalogenides, alkinylhalogenides, arylalkylhalogenides, arylalkenylhalogenides, arylalkinylhalogenides or chloroformates in solvents such as N,N-dimethylformamide (DMF) or tetrahydrofuran (THF) in the presence of a strong base such as sodium hydride, potassium hydride or sodium amide to obtain the compounds of formula (XV),

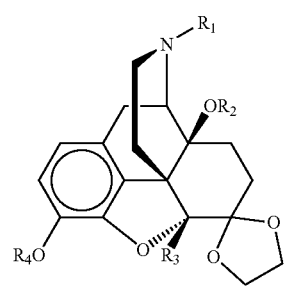

(XV)

where $R_1$, $R_2$, $R_3$ and $R_4$ are defined as above. If $R_2$ and $R_4$ are benzyl, compounds of the formula (XIII) can be directly reacted with two equivalents of benzyl bromide in DMF in the presence of sodium hydride, forming 3,14-O-dibenzyl derivatives of the formula (XV), in which $R_2$ and $R_4$ are benzyl and $R_1$ and $R_3$ are defined as above.

The acidic splitting of the 3-O protective group and the ketal function of the compounds with the formula (XV) is carried out in one step with an acid such as hydrochloric acid in methanol, tetrafluoroboric acid in dichloromethane or trifluoroacetic acid and compounds of the formula (X) are obtained (see 1st route).

Alternatively to this, if $R_4$ in compounds of formula (XV) is benzyl, one can, through hydrogenolysis of the 3-O-benzyl binding with hydrogen gas in the presence of a catalyst such as Pd/C, PdO, Pd/$Al_2O_3$, Pt/C, $PtO_2$, Pt/$Al_2O_3$ or similar in solvents such as alcohols, alcohol/water mixtures, glacial acetic acid or similar compounds, followed by acid hydrolysis of the ketal function in Position 6 with, for example, methanol and concentrated hydrochloric acid obtain compounds of the formula (X) (see 1$^{st}$ route).

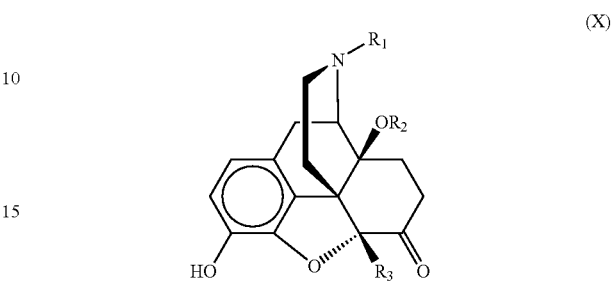

(X)

in which $R_1$, $R_2$, and $R_3$ are defined as above.

The compounds of the formula (X) are reacted according to the first scheme to form compounds according to the invention of formula (I).

Compounds of the formula (I) can be converted to compounds of the formula (Ia), in which $R_5$ is hydrogen; hydroxy; $C_1$-$C_6$-alkyloxy; $C_2$-$C_{10}$-alkyloxyalkoxy, where alkyloxy is $C_1$-$C_4$ and alkoxy is $C_1$-$C_6$-alkyloxy $C_1$-$C_6$-alkyloxy; $C_2$-$C_6$-alkenyloxy; $C_2$-$C_6$-alkinyloxy; $C_4$-$C_{16}$-cycloalkylalkyloxy, where cycloalkyl is $C_3$-$C_{10}$ and alkyl is $C_1$-$C_6$; $C_5$-$C_{16}$-cycloalkylalkenyloxy, where cycloalkyl is $C_3$-$C_{10}$ and alkenyl is $C_2$-$C_6$; $C_5$-$C_{16}$-cycloalkylalkinyloxy, where cycloalkyl is $C_3$-$C_{10}$ and alkinyl is $C_2$-$C_6$; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_7$-$C_{16}$-arylalkanoyloxy, where aryl is $C_6$-$C_{10}$-aryl and alkanoyloxy is $C_1$-$C_6$-alkylanoyloxy, as follows:

Compounds of the formula (I) can be converted to compounds of the formula (XVI) in that first a reductive opening of the 4,5-ether bridge is carried out with for example zinc in an alcohol, such as methanol or ethanol (preferred temperature 40-80° C.) in the presence of ammonium chloride.

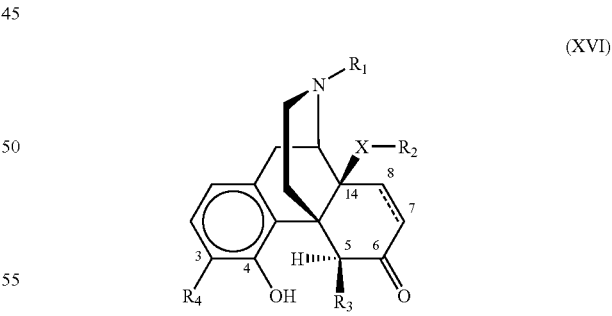

(XVI)

($R_1$, $R_2$ and $R_3$ are as stated above; for $R_4$ see formula (I))

Compounds of the formula (XVI) can be converted to the compounds according to the invention of formula (Ia) in which $R_5$ is $C_1$-$C_6$-alkyloxy; $C_2$-$C_{10}$-alkyloxyalkoxy, where alkyloxy is $C_1$-$C_4$ and alkoxy is $C_1$-$C_6$-alkyloxy $C_1$-$C_6$-alkyloxy; $C_2$-$C_6$-alkenyloxy; $C_2$-$C_6$-alkinyloxy; $C_4$-$C_{16}$-cycloalkylalkyloxy, where cycloalkyl is $C_3$-$C_{10}$ and alkyl is $C_1$-$C_6$; $C_5$-$C_{16}$-cycloalkylalkenyloxy, where cycloalkyl is $C_3$-$C_{10}$ and alkenyl is $C_2$-$C_6$; $C_5$-$C_{16}$-cycloalkylalkinyloxy, where cycloalkyl is $C_3$-$C_{10}$ and alkinyl is $C_2$-$C_6$; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_7$-$C_{16}$-arylalkanoyloxy, where aryl is $C_6$-$C_{10}$-aryl and alkanoyloxy is $C_1$-$C_6$-alkylanoyloxy, and $R_1$, $R_2$ and $R_3$ are as stated above and $R_4$ is stated in formula (I), through alkylation or acylation according to generally accepted methods.

Compounds of the formula (XVI) can be converted to the compounds according to the invention of formula (I) in which $R_5$ is hydrogen by removing the hydroxyl group in Position 4. This can occur for example by the formation of the corresponding phenyltetrazolylether in the presence of a base such as potassium carbonate in a solution such as N,N-dimethylformamide and then catalytic hydration of the phenyltetrazolylether, for example over a catalyst such as Pd/C in an alcohol or glacial acetic acid at temperatures between 20° C. and 100° C. (see for example Schmidhammer et al. J. Med. Chem. 1984, 27, pp. 1575-1579).

Compounds of the formula (I) or (Ia) can be converted into quaternary ammonium salts of the formula (IA) or (IAa) by alkylation with an appropriate alkyl halogenide or another alkylation agent in solvents such as N,N-dimethylformamide, acetonitrile, acetone, alcohols, tetrahydrofuran, ether, ethyl acetate, etc. or in a solvent mixture. The arrangement of the incoming substituents is preferably axial (see M. A. Iorio et al., Eur. J. Med. Chem.—Chim. Ther. 1984, 19, 301-303).

The following examples describe the production of the compounds according to the invention in detail.

EXAMPLE 1

Synthesis of 17-allyl-4,5α-epoxy-3-methoxy-14β-(3-phenylpropyloxy)morphinan-6-one hypochloride (compound 1.HCl (Verbindung 1))

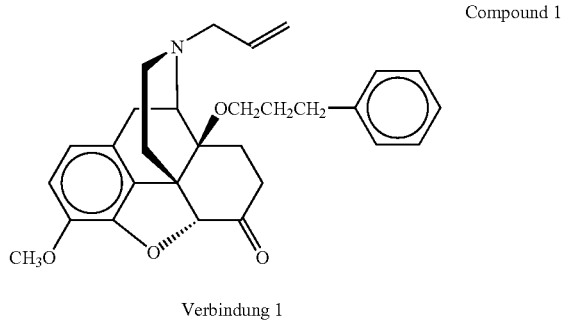

Compound 1

Verbindung 1

NaH (0.97 g, 40.4 mmol) (obtained from 1.62 g 60% NaH dispersion in oil by washing with petroleum ether) was added to a solution of 14-hydroxycodeinone (Iijima et al. J. Med. Chem. 1978, 21, pg. 398) (3.00 g, 9.6 mmol) in 100 ml of water-free N,N-dimethylformamide und $N_2$ at 0° C. (bath temperature) under stirring. After 20 min. cinnamyl bromide (2.28 g, 11.6 mmol) is added and the mixture then stirred for 30 min. at 0° C. (bath temperature), then stirred further with reducing cooling for 4.5 hours. To terminate the reaction pieces of ice were added until no more hydrogen was produced and the mixture made up to 100 ml of water. The precipitated product was extracted with dichloromethane (3×100 ml), the combined organic phases washed with 250 ml saturated sodium chloride solution and dried over sodium sulphate. After removal of the solvent under reduced pressure a brown oil was obtained. This was crystallised from methanol. Yield: 2.49 g (60%) of colourless crystals of 14-cinnamyloxycodeinone (=7,8-dihydro-4,5α-expoxy-3-methoxy-17-methyl-14β-{[(E)-3-phenylprop-2-enyl]oxy}morphinan-6-one. Fp. 216-219° C.; $^1$H-NMR (DMSO-$d_6$, δ in ppm): δ 7.46-7.17 (m, 5 arom. H), 7.19 (d, 1 olef. H, CH-8, J=10.2 Hz), 6.74 (d, 1 arom. H, J=8.3 Hz), 6.65 (d, 1 arom. H, J=8.3 Hz), 6.51-6.59 (m, 1 olef. H, —CH=C$\underline{H}$-Ph), 6.34 (trans) and 6.26 (cis) (2 ps-d, 1 olef. H, —C$\underline{H}$=CH-Ph), 6.18 (d, 1 olef. H, CH-7, J=10.2 Hz), 4.85 (s, CH-5), 4.26 and 4.11 (2 dxdxd, 2H, C-14-OCH$_2$—), 3.73 (s, CH$_3$O), 2.36 (s, CH$_3$N).

A mixture of 14-cinnamyloxycodeinone (6.27 g, 14.6 mmol) and 0.32 g Pd/C (10%) in 200 ml glacial acetic acid was hydrogenated for 3 h at 30 psi and room temperature. The catalyst was filtered off and washed with 50 ml of glacial acetic acid. The filtrate was evaporated down, water added and alkalised with concentrated ammonia and extracted with dichloromethane (3×50 ml). The combined organic phases were washed with saturated sodium chloride solution (3×70 ml), dried over sodium sulphate and evaporated down. The oily residue (6.27 g) was crystallised from methanol. Yield: 4.93 g (78%) of colourless crystals of 4,5α-epoxy-3-methoxy-17-methyl-14β-(3-phenylpropyloxy)morphinan-6-one (=14-O-(3-phenylpropyl)oxycodon). Fp. 119-121° C.; $^1$H-NMR (CDCl$_3$, δ in ppm): δ 7.35-7.15 (m, 5 arom. H), 6.68 (d, 1 arom. H, J=8.2 Hz), 6.60 (d, 1 arom. H, J=8.2 Hz), 4.63 (s, CH-5), 3.89 (s, CH$_3$O), 2.34 (s, CH$_3$N).

A mixture of 4,5α-epoxy-3-methoxy-17-methyl-14β-(3-phenylpropyloxy)morphinan-6-one (=14-O-(3-phenylpropyl)oxycodon) (5.00 g, 11.50 mmol), sodium bicarbonate (6.8 g, 80.91 mmol) and chloroformic acid-1-chloroethyl-ester (7.5 ml, 67.5 mmol) in 30 ml 1,2-dichloroethane was reflux heated with exclusion of moisture at 60° C. (bath temperature) under stirring. After 17 h filtration was carried out from the inorganic residue, washed with dichloromethane and the filtrate evaporated down. The carbamate produced was not isolated, but rather dissolved in 100 ml methanol and reflux heated for one hour. The solution was evaporated down and the evaporation residue, a colourless foamy resin (6.08 g) was crystallised out of acetone. Yield: 4.91 g (93%) 4,5β-epoxy-3-methoxy-14β-(3-phenylpropyloxy)morphinan-6-one hydrochloride as colourless crystals. Fp. 215-218° C.; IR (KBr): 1730 (CO) cm$^{-1}$; $^1$H-NMR (CDCl$_3$): δ 10.55 and 8.67 (2 s, wide, 2H, $^+$NH$_2$), 7.28-7.10 (m, 5 arom. H), 6.75 (d, 1 arom. H, J=8.2 Hz), 6.71 (d, 1 arom. H, J=8.2 Hz), 4.41 (s, C5-H), 3.89 (s, CH$_3$O); EI-MS: m/z 419 (M$^+$).

A mixture of 4,5α-epoxy-3-methoxy-14β-(3-phenylpropyloxy)morphinan-6-one hydrochloride (2.00 g, 4.76 mmol), potassium carbonate (4.00 g, 28.9 mmol) and allyl bromide (0.56 ml, 6.62 mmol) in water-free N,N-dimethylformamide (15 ml) was stirred for 7 h under exclusion of moisture and under nitrogen at 80° C. (bath temperature). After filtration from the inorganic residue, which was washed three times each time with 50 ml dichloromethane, the filtrate was evaporated down under reduced pressure. The oily residue was dissolved in 300 ml dichloromethane, washed with water (3×200 ml) and saturated sodium chloride solution (4×200 ml), dried over sodium sulphate and evaporated down. The obtained brown oil was purified by column chromatography (silica gel; CH$_2$Cl$_2$/MeOH/conc. NH$_4$OH 250:2:0.5), the oily evaporation residue dissolved in 50 ml ether and precipitated by the addition of etherial HCl up to the acid reaction. The product was recrystallised from isopropanol. Yield: 1.50 g (69%) of the compound 1.HCl as colourless crystals. Fp. 129-130° C.; MS (CI): 460 (M$^+$+1); IR (KBr): 1725 (C=O) cm$^{-1}$; $^1$H-NMR (DMSO-$d_6$, δ in ppm): δ 8.98 (s, wide, HN$^+$), 7.30-7.18 (m, 5 arom. H), 6.89 (d, 1 arom. H, J=8.4 Hz), 6.83 (d, 1 arom. H, J=8.4 Hz), 5.89 (m, 1 olef. H), 5.69 (m, 2 olef. H), 4.94 (s, CH-5), 3.81 (s, CH$_3$O).

EXAMPLE 2

Synthesis of 17-cyclobutylmethyl-4,5α-epoxy-3-methoxy-14β-(3-phenylpropyloxy)morphinan-6-one hydrochloride (compound 2.HCl)

Compound 2

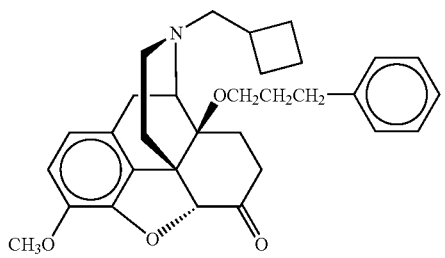

Verbindung 2

A mixture of 4,5α-epoxy-3-methoxy-14β-(3-phenylpropyloxy)morphinan-6-one hydrochloride (500 mg, 1.19 mmol), potassium carbonate (1.00 g, 7.24 mmol) and cyclobutylmethylbromide (0.6 ml, 5.43 mmol) in water-free N,N-dimethylformamide (7 ml) was stirred for 24 h under exclusion of moisture and under nitrogen at 80° C. (bath temperature). After filtration from the inorganic residue, which was washed three times each time with 20 ml dichloromethane, the filtrate was evaporated down under reduced pressure. The oily residue was dissolved in 100 ml dichloromethane, washed with water (3×100 ml) and saturated sodium chloride solution (4×100 ml), dried over sodium sulphate and evaporated down. The evaporation residue (520 mg of brown oil) was purified by column chromatography (silica gel; $CH_2Cl_2$/MeOH/conc. $NH_4OH$ 250:2:0.5), the oily evaporation residue dissolved in 10 ml ether and precipitated by the addition of etherial HCl. Yield: 0.40 g (69%) of the compound 2.HCl as colourless crystals. Fp. 128-133° C.; MS (CI): 488 (M$^+$+1); IR (KBr): 1728 (C=O) cm$^{-1}$; $^1$H-NMR (DMSO-d$_6$, δ in ppm): δ 8.48 (s, wide, HN$^+$), 7.30-7.15 (m, 5 arom. H), 6.87 (d, 1 arom. H, J=8.4 Hz), 6.77 (d, 1 arom. H, J=8.4 Hz), 4.93 (s, CH-5), 3.81 (s, CH$_3$O).

EXAMPLE 3

Synthesis of 17-cyclopropylmethyl-4,5α-epoxy-3-methoxy-14β-(3-phenylpropyloxy)morphinan-6-one hydrochloride (compound 3.HCl).

Compound 3

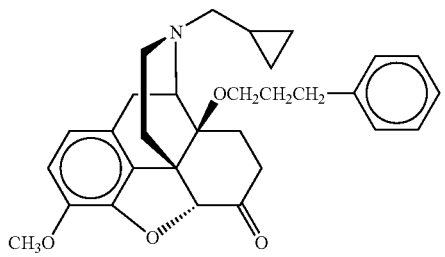

Verbindung 3

A mixture of 4,5α-epoxy-3-methoxy-14β-(3-phenylpropyloxy)morphinan-6-one hydrochloride (1.5 g, 3.57 mmol), potassium carbonate (3.00 g, 21.7 mmol) and cyclopropylmethylbromide (1.0 ml, 6.62 mmol) in water-free N,N-dimethylformamide (10 ml) was stirred for 4 h under exclusion of moisture and under nitrogen at 80° C. (bath temperature). After filtration from the inorganic residue, which was washed three times each time with 10 ml dichloromethane, the filtrate was evaporated down under reduced pressure. The oily residue was dissolved in 50 ml dichloromethane, washed with water (3×50 ml) and saturated sodium chloride solution (4×50 ml), dried over sodium sulphate and evaporated down. The evaporation residue (1.42 g of yellow oil) was purified by column chromatography (silica gel; $CH_2Cl_2$/MeOH/conc. $NH_4OH$ 250:2:0.5), the oily evaporation residue dissolved in 50 ml ether and precipitated by the addition of etherial HCl up to the acidic reaction. Yield: 0.60 g (53%) of the compound 3.HCl as colourless crystals. Fp. 130-133° C.; MS (EI): 473 (M$^+$); IR (KBr): 1725 (C=O) cm$^{-1}$; $^1$H-NMR (DMSO-d$_6$, δ in ppm): δ 8.30 (s, wide, HN$^+$), 7.31-7.18 (m, 5 arom. H), 6.88 (d, 1 arom. H, J=8.4 Hz), 6.78 (d, 1 arom. H, J=8.4 Hz), 4.96 (s, CH-5), 3.81 (s, CH$_3$O), 0.80-0.40 (m, 5 cyclopropyl H).

EXAMPLE 4

Synthesis of 4,5α-epoxy-3-methoxy-17-(2-phenylethyl)-14β-(3-phenylpropyloxy)morphinan-6-one hydrochloride (compound 4.HCl)

Compound 4

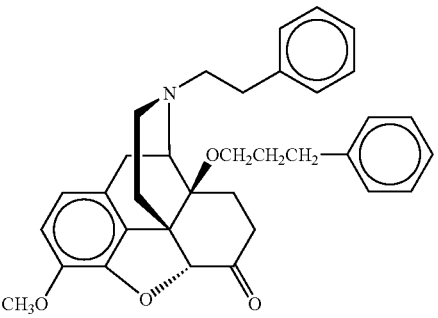

Verbindung 4

A mixture of 4,5α-epoxy-3-methoxy-14β-(3-phenylpropyloxy)morphinan-6-one hydrochloride (1.0 g, 2.38 mmol), potassium carbonate (3.00 g, 21.7 mmol) and 2-phenylethylbromide (1.19 ml, 8.8 mmol) in water-free N,N-dimethylformamide (10 ml) was stirred for 12 h under exclusion of moisture and under nitrogen at 80° C. (bath temperature). After filtration from the inorganic residue, which was washed three times each time with 50 ml dichloromethane, the filtrate was evaporated down under reduced pressure. The oily residue was dissolved in 300 ml dichloromethane, washed with water (3×200 ml) and saturated sodium chloride solution (4×200 ml), dried over sodium sulphate and evaporated down. The evaporation residue (960 mg of brown oil) was purified by column chromatography (silica gel; $CH_2Cl_2$/MeOH/conc. $NH_4OH$ 250:2:0.5), the oily evaporation residue dissolved in 50 ml ether and precipitated by the addition of etherial HCl up to the acidic reaction. Yield: 0.45 g (36%) of the compound 4.HCl as colourless crystals. Fp. 128-130° C.; MS (CI): 524 (M$^+$+1); IR (KBr): 1726 (C=O) cm$^{-1}$; $^1$H-NMR (DMSO-d$_6$, δ in ppm): δ 8.84 (s, wide, HN$^+$), 7.39-7.17 (m, 10 arom. H), 6.89 (d, 1 arom. H, J=8.2 Hz), 6.79 (d, 1 arom. H, J=8.2 Hz), 4.95 (s, CH-5), 3.81 (s, CH$_3$O).

EXAMPLE 5

Synthesis of 4,5α-epoxy-17-[2-((R,S)-tetrahydrofuran-2-yl)methyl]-3-methoxy-14β-(3-phenylpropyloxy)morphinan-6-one hydrochloride (compound 5.HCl)

Compound 5

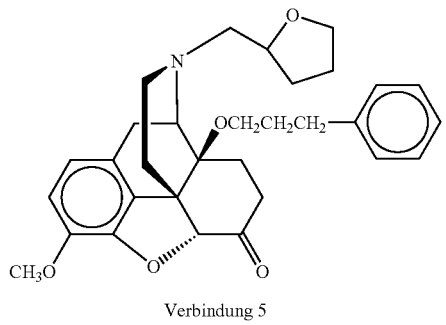

Verbindung 5

A mixture of 4,5α-epoxy-3-methoxy-14β-(3-phenylpropyloxy)morphinan-6-one hydrochloride (1.0 g, 2.38 mmol), potassium carbonate (0.6 g, 4.34 mmol) and tetrahydrofurfurylchloride (0.5 ml, 4.59 mmol) in water-free N,N-dimethylformamide (10 ml) was stirred for 15 h under exclusion of moisture and under nitrogen at 150° C. (bath temperature). The mixture was cooled, 50 ml of water added to it and it was extracted with dichloromethane (3×30 ml). The combined organic phases were washed with water (3×60 ml) and saturated sodium chloride solution (4×100 ml), dried over sodium sulphate and evaporated down. The residue (1.3 g of brown oil) was purified by column chromatography (silica gel; $CH_2Cl_2$/MeOH/conc. $NH_4OH$ 250:1.5:0.5->250:3.5:0.5), the oily evaporation residue dissolved in 50 ml ether and precipitated by the addition of etherial HCl up to the acidic reaction. Yield: 0.57 g (48%) of the compound 5.HCl as colourless crystals. Fp. 121-123° C.; MS (CI): 504 (M$^+$+1); IR (KBr): 1727 (C=O) cm$^{-1}$; $^1$H-NMR (DMSO-d$_6$, δ in ppm): δ 8.18 and 7.64 (s, wide, HN$^+$), 7.08-6.96 (m, 5 arom. H), 6.88-6.52 (d, 2 arom. H), 4.75 and 4.73 (2 s, CH-5), 3.79 and 3.81 (2s, CH$_3$O).

EXAMPLE 6

Synthesis of 17-allyl-4,5α-epoxy-3-hydroxy-14β-(3-phenylpropyloxy)morphinan-6-one hydrochloride (compound 6.HCl)

Compound 6

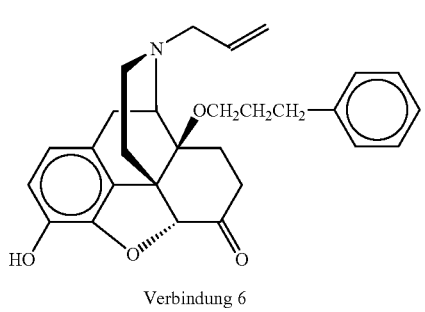

Verbindung 6

A solution of compound 1.HCl (1.50 g, 3.02 mmol) in 5 ml 48% HBr was reflux heated for 15 min. Then the solution was cooled, poured onto approx. 50 ml of ice, alkalised with conc. NH$_4$OH and extracted with dichloromethane (3×80 ml). The combined organic phases were washed with saturated sodium chloride solution (4×50 ml), dried over sodium sulphate and evaporated down. The residue (1.3 g of brown oil) was purified by column chromatography (silica gel; $CH_2Cl_2$/MeOH/conc. $NH_4OH$ 250:2:0.5), the oily evaporation residue dissolved in 50 ml ether and precipitated by the addition of etherial HCl up to the acidic reaction. Yield: 0.5 g (34%) of the compound 6.HCl as colourless crystals. Fp. >250° C. (decomp.); MS (CI): 446 (M$^+$+1); IR (KBr): 1725 (C=O) cm$^{-1}$; $^1$H-NMR (DMSO-d$_6$, δ in ppm): g 9.51 (s, OH), 8.81 (s, wide, HN$^+$), 7.30-7.16 (m, 5 arom. H), 6.71 (d, 1 arom. H, J=8.0 Hz), 6.64 (d, 1 arom. H, J=8.0 Hz), 5.92 (m, 1 olef. H), 5.61 (m, 2 olef. H), 4.87 (s, CH-5).

EXAMPLE 7

Synthesis of 17-cyclobutylmethyl-4,5α-epoxy-3-hydroxy-14β-(3-phenylpropyloxy)morphinan-6-one hydrochloride (compound 7.HCl)

Compound 7

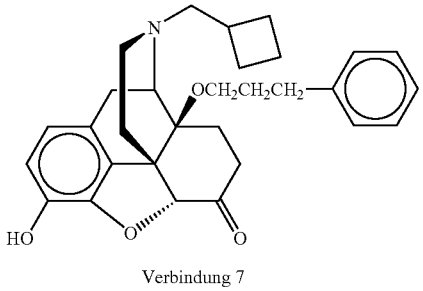

Verbindung 7

A solution of compound 2.HCl (336 mg, 0.64 mmol) in 5 ml 48% HBr was reflux heated for 15 min. Then the solution was cooled, poured onto approx. 50 ml of ice, alkalised with conc. NH$_4$OH and extracted with dichloromethane (3×50 ml). The combined organic phases were washed with saturated sodium chloride solution (4×50 ml), dried over sodium sulphate and evaporated down. The residue (210 mg of brown foamy resin) was purified by column chromatography (silica gel; $CH_2Cl_2$/MeOH/conc. $NH_4OH$ 250:2:0.5), the oily evaporation residue dissolved in 50 ml ether and precipitated by the addition of etherial HCl up to the acidic reaction. Yield: 79 mg (34%) of the compound 7.HCl as colourless crystals. Fp. >227° C. (decomp.); MS (CI): 474 (M$^+$+1); IR (KBr): 1725 (C=O) cm$^{-1}$; $^1$H-NMR (DMSO-d$_6$, δ in ppm): δ 9.51 (s, OH), 8.30 (s, wide, HN$^+$), 7.29-7.18 (m, 5 arom. H), 6.70 (d, 1 arom. H, J=8.4 Hz), 6.63 (d, 1 arom. H, J=8.4 Hz), 4.86 (s, CH-5).

EXAMPLE 8

Synthesis of 17-cyclopropylmethyl-4,5α-epoxy-3-hydroxy-14β-(3-phenylpropyloxy)morphinan-6-one hydrochloride (compound 8.HCl)

Compound 8

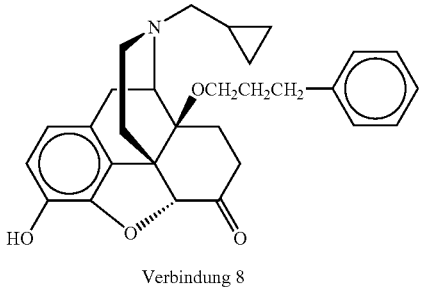

Verbindung 8

A solution of compound 3.HCl (600 mg, 1.26 mmol) in 5 ml 48% HBr was reflux heated for 12 min. Then the solution was cooled, poured onto approx. 50 ml of ice, alkalised with conc. NH$_4$OH and extracted with dichloromrethane (3×50 ml). The combined organic phases were washed with saturated sodium chloride solution (4×50 ml), dried over sodium sulphate and evaporated down. The brown oil obtained was purified by column chromatography (silica gel; CH$_2$Cl$_2$/MeOH/conc. NH$_4$OH 250:2:0.5), the oily evaporation residue dissolved in 50 ml ether and precipitated by the addition of etherial HCl up to the acidic reaction. Recrystallisation out of isopropanol gave 200 mg (34%) of the pure compound 8.HCl as colourless crystals. Fp. 175-178° C.; MS (CI): 460 (M$^+$+1); IR (KBr): 1725 (C=O) cm$^{-1}$; $^1$H-NMR (DMSO-d$_6$, δ in ppm): δ 9.52 (s, OH), 8.20 (s, wide, HN$^+$), 7.30-7.18 (m, 5 arom. H), 6.71 (d, 1 arom. H, J=8.0 Hz), 6.64 (d, 1 arom. H, J=8.0 Hz), 4.89 (s, CH-5).

EXAMPLE 9

Synthesis of 4,5α-epoxy-3-hydroxy-17-(2-phenyl-ethyl)-14β-(3-phenylpropyloxy)morphinan-6-one hydrochloride (compound 9.HCl)

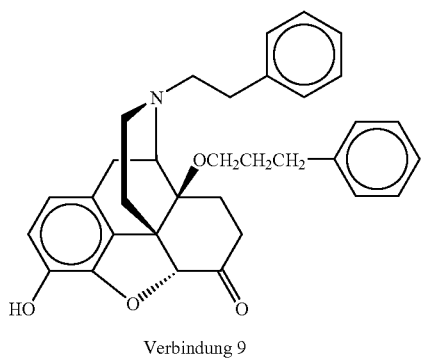

Compound 9

Verbindung 9

A solution of compound 4.HCl (1.79 g, 3.2 mmol) in 5 ml 48% HBr was reflux heated for 15 min. Then the solution was cooled, poured onto approx. 50 ml of ice, alkalised with conc. NH$_4$OH and extracted with dichloromethane (3×60 ml). The combined organic phases were washed with saturated sodium chloride solution (4×60 ml), dried over sodium sulphate and evaporated down. The brown oil obtained (1.02 g) was purified by column chromatography (silica gel; CH$_2$Cl$_2$/MeOH/conc. NH$_4$OH 250:2:0.5), the oily evaporation residue dissolved in 50 ml ether and precipitated by the addition of etherial HCl up to the acidic reaction. Yield: 247 mg (15%) of the pure compound 9.HCl as colourless crystals. Fp. >218° C. (decomp.); MS (CI): 510 (M$^+$+1); IR (KBr): 1725 (C=O) cm$^{-1}$; $^1$H-NMR (DMSO-d$_6$, δ in ppm): δ 9.51 (s, OH), 8.84 (s, wide, HN$^+$), 7.39-7.17 (m, 10 arom. H), 6.72 (d, 1 arom. H, J=8.4 Hz), 6.66 (d, 1 arom. H, J=8.4 Hz), 4.87 (s, CH-5).

EXAMPLE 10

Synthesis of 4,5α-epoxy-17-[2-((R,S)-tetrahydrofuran-2-yl)methyl]-3-hydroxy-14β-(3-phenylpropyloxy)morphinan-6-one hydrochloride (compound 10.HCl)

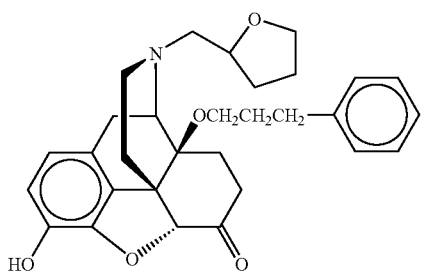

Compound 10

Verbindung 10

A solution of compound 5.HCl (600 mg, 1.11 mmol) in 5 ml 48%. HBr was reflux heated for 15 min. Then the solution was cooled, poured onto approx. 50 ml of ice, alkalised with conc. NH$_4$OH and extracted with dichloromethane (3×60 ml). The combined organic phases were washed with saturated sodium chloride solution (4×60 ml), dried over sodium sulphate and evaporated down. The brown oil obtained (0.52 g) was purified by column chromatography (silica gel; CH$_2$Cl$_2$/MeOH/conc. NH$_4$OH 250:2:0.5), the oily evaporation residue dissolved in 50 ml ether and precipitated by the addition of etherial HCl up to the acidic reaction. Yield: 210 mg (36%) of the compound 10.HCl as colourless crystals. Fp. 170-172° C.; MS (CI): 490 (M$^+$+1); IR (KBr): 1725 (C=O) cm$^{-1}$; $^1$H-NMR (DMSO-d$_6$, δ in ppm): δ 9.45 (s, OH), 8.45 and 7.85 (s, wide, HN$^+$), 7.30-7.21 (m, 5 arom. H), 6.70-6.65 (m, 2 arom. H), 4.90 and 4.87 (2 s, CH-5).

EXAMPLE 11

Synthesis of 4,5α-epoxy-3-hydroxy-14β-(3-phenylpropyloxy)-17-propylmorphinan-6-one hydrochloride (compound 11.HCl)

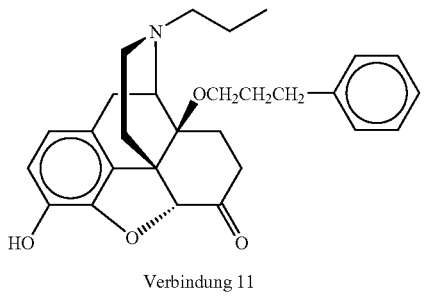

Compound 11

Verbindung 11

A mixture of compound 6.HCl (308 mg, 0.64 mmol) and 35 mg 10% Pd/C catalyst in 50 ml methanol was hydrogenated for 3 h at 30 psi and room temperature. The catalyst was filtered off and washed with 50 ml methanol. The filtrate was evaporated down. The evaporation residue, a colourless foamy resin, was dissolved in 30 ml ether and precipitated as the hydrochloride by the addition of etherial HCl up to the acid reaction. Yield: 295 mg (95%) colourless crystals of the compound 11.HCl. Fp. 162-163° C.; MS (CI): 460 ($M^++1$); IR (KBr): 1725 (C=O) $cm^{-1}$; $^1$H-NMR (DMSO-$d_6$, δ in ppm): δ 9.51 (s, OH), 8.50 (s, wide, $HN^+$), 7.30-7.18 (m, 5 arom. H), 6.75 (d, 1 arom. H, J=8.4 Hz), 6.64 (d, 1 arom. H, J=8.4 Hz), 4.86 (s, CH-5), 0.94 (t, $CH_3CH_2CH_2$, J=7 Hz).

EXAMPLE 12

Synthesis of 17-cyclopropylmethyl-4,5α-epoxy-3-hydroxy-14β-[(2-methylbenzyl)oxy]-morphinan-6-one hydrochloride (compound 12.HCl)

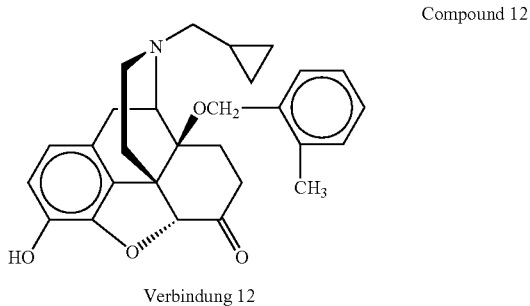

Compound 12

Verbindung 12

A solution of tritylbromide (3.8 g, 11.86 mmol), triethylamine (2.41 ml, 15.99 mmol), DMAP (14 mg, 0.21 mmol) and 17-cyclopropylmethyl-4,5α-epoxy-3,14β-dihydroxymorphinan-6-spiro-2'-(1,3-dioxolane) (Schmidhammer et al., Heterocycles 1998, 49, 489-497) (3.0 g, 7.78 mmol) in $CH_2Cl_2$ (80 ml) was reflux heated for 24 h, cooled and washed with $H_2O$ (2×100 ml). The combined organic phases were evaporated down and the residue (7.11 g of yellow crystals) was recrystallised out of MeOH (15 ml). Yield: 4.15 g (85%) of 17-cyclopropylmethyl-4,5α-epoxy-14β-hydroxy-3-triphenylmethoxymorphinan-6-spiro-2'-(1,3-dioxolane). Fp. 203-205° C.; $^1$H-NMR (CDCl$_3$) δ 7.50-7.15 (m, 15 arom. H), 6.60 (d, 1 arom. H, J=8.2 Hz), 6.30 (d, 1 arom. H, J=8.2 Hz), 6.13 (s, wide, OH), 4.37 (s, CH-5), 4.12-3.80 (m, 4H, OCH$_2$CH$_2$O); CI-MS: m/z 628 ($M^++1$).

NaH (312 mg, 13.34 mmol) (obtained from 520 mg of a 60% NaH dispersion in oil by washing with petroleum ether) was added to a solution of 17-cyclopropylmethyl-4,5α-epoxy-14β-hydroxy-3-triphenylmethoxymorphinan-6-spiro-2'-(1,3-dioxolane) (2.0 g, 3.18 mmol) in water-free N,N-dimethylformamide (20 ml) under $N_2$ at 0° C. (bath temperature) under stirring. After 20 min. 2-methylbenzylbromide (0.64 ml, 5.4 mmol) was added and the resulting mixture stirred for 20 h at room temperature. Excess NaH was broken down by the addition of small pieces of ice and then the mixture was diluted with $H_2O$ (80 ml) and extracted with $CH_2Cl_2$ (1×40 ml, 2×30 ml). The combined organic phases were washed with $H_2O$ (3×100 ml), dried (Na$_2$SO$_4$) and evaporated down. The residue (1.8 g of orange coloured oil) was purified using column chromatography (silica gel; $CH_2Cl_2$/MeOH/conc. NH$_4$OH 250:2:0.5). 480 mg of a yellow oil was obtained, which was crystallised out of MeOH. Yield: 304 mg (13%) of pure 17-cyclopropylmethyl-4,5α-epoxy-14β-[(2-methylbenzyl)oxy]-3-triphenylmethoxy)morphinan-6-spiro-2'-(1,3-dioxolane). Fp 180-182° C.; $^1$H-NMR (Me$_2$SO-d$_6$): δ 7.30-7.15 (m, 19 arom. H), 6.31 (d, 1 arom. H, J=8.2 Hz), 6.23 (d, 1 arom. H, J=8.2 Hz), 4.68 (d, 1H, OCH$_2$Ar, J=10.2 Hz), 4.22 (d, 1H, OCH$_2$Ar, J=10.2 Hz), 4.17 (s, CH-5), 4.05-3.50 (m, 4H, OCH$_2$CH$_2$O), 2.33 (s, 3H, MePh); Cl-MS: m/z 733 ($M^++1$).

A solution of 17-cyclopropylmethyl-4,5α-epoxy-14β-[(2-methylbenzyl)oxy]-3-(triphenylmethoxy)morphinan-6-spiro-2'-(1,3-dioxolane) (300 mg, 0.67 mmol) in MeOH (5 ml) and conc. HCl (0.5 ml) was reflux heated for 10 h. After cooling with ice, the solution was alkalised with conc. NH$_4$OH and extracted with $CH_2Cl_2$ (1×30 ml, 2×20 ml). The combined organic phases were washed with $H_2O$, dried over Na$_2$SO$_4$ and evaporated down. The residue (165 mg of yellow oil) was purified using column chromatography (silica gel; $CH_2Cl_2$/MeOH/conc. NH$_4$OH 250:2:0.5). 80 mg of a colourless oil was obtained, which was dissolved in ether and precipitated as the hydrochloride by the addition of etherial HCl up to the acidic reaction. Yield: 70 mg (23%) of pure compound 12.HCl. Fp. 198-200° C.; $^1$H-NMR (Me$_2$SO-d$_6$): δ 9.50 (s, OH), 8.60 (s, $^+$NH), 7.67-7.22 (m, 4 arom. H), 6.74 (d, 1 arom. H, J=8 Hz), 6.69 (d, 1 arom. H, J=8 Hz), 5.16 (s, C-5H), 2.31 (s, 3H, MePh); CI-MS: m/z 446 ($M^++1$).

EXAMPLE 13

Synthesis of 14β-[(2-chlorobenzyl)oxy]-17-(cyclopropylmethyl)-4,5α-epoxy-3-hydroxymorphinan-6-one hydrochloride (compound 13.HCl)

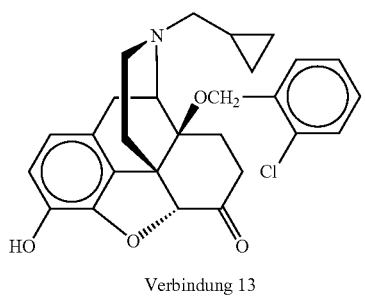

Compound 13

Verbindung 13

A mixture of 17-cyclopropylmethyl-4,5α-epoxy-3,14β-dihydroxymorphinan-6-spiro-2'-(1,3-dioxolane) (Schmidhammer et al. Heterocycles 1998, 49, 489-497) (6.9 g, 17.9 mmol), K$_2$CO$_3$ (6.7 g, 48.48 mmol), benzylbromide (2.34 ml, 19.66 mmol) and water-free N,N-dimethylformamide (70 ml) was stirred for 22 h under $N_2$ and at room temperature. The inorganic material was filtered off and the filtrate evaporated down. The residue was dissolved in $CH_2Cl_2$ (80 ml), washed with $H_2O$ (7×50 ml), dried over Na$_2$SO$_4$ and evaporated down. The residue (8.2 g of colourless crystals) was recrystallised out of MeOH. Yield: 7.37 g (87%) 3-benzyloxy-17-cyclopropylmethyl-4,5α-epoxy-14f-hydroxymorphinan-6-spiro-2'-(1,3-dioxolane). Fp. 130-131° C.; $^1$H-NMR (CDCl$_3$): δ 7.42-7.27 (m, 5 arom. H), 6.75 (d, 1 arom. H, J=8.3 Hz), 6.54 (d, 1 arom. H, J=8.3 Hz), 5.17 (d, 1H, OCH$_2$Ph, J=11.7 Hz), 5.10 (d, 1H, OCH$_2$Ph, J=11.7 Hz), 4.58 (s, C-5H), 4.19-3.73 (m, 4H, OCH$_2$CH$_2$O); CI-MS: m/z 476 ($M^++1$).

A mixture of 3-(benzyloxy)-17-(cyclopropylmethyl)-4, 5α-epoxy-14β-hydroxy-morphinan-6-spiro-2'-(1,3-dioxolane) (5.82 g, 12.2 mmol), NaH (1.47 g, 61.3 mmol; obtained from 2.45 g of a 60% NaH dispersion in oil by washing with petroleum ether) and 100 ml water-free N,N-dimethylformamide was stirred for 25 min. under $N_2$ at 0-5° C. (bath temperature). 2-chlorobenzylbromide (3.16 ml, 24.3 mmol) was added and the resulting mixture stirred for 4 h (1 h at 0-5° C., 3 h at room temperature). Excess NaH was broken down by the addition of small pieces of ice, and then the mixture diluted with H$_2$O (350 ml) and extracted with CH$_2$Cl$_2$ (1×250 ml, 3×100 ml). The combined organic phases were washed with H$_2$O (3×100 ml) and saturated sodium chloride solution (2×50 ml), dried (Na$_2$SO$_4$), and evaporated down. The residue (8.3 g of yellowish oil) was purified using column chromatography (silica gel; CH$_2$Cl$_2$/MeOH/conc. NH$_4$OH 250:4:0.5). 4.75 g (65%) of pure 3-(benzyloxy)-14β-[(2-chlorobenzyl)oxy]-17-cyclopropylmethyl-4,5α-epoxy-morphinan-6-spiro-2'-(1,3-dioxolane) was obtained as a colourless oil, which was used for the next synthetic stage as such. $^1$H-NMR (Me$_2$SO-d$_6$) δ 7.71-7.31 (m, 9 arom. H), 6.79 (d, 1 arom. H, J=8.0 Hz), 6.57 (d, 1 arom. H, J=8.0 Hz), 5.14 (d, 1H, OCH$_2$Ar, J=11.6 Hz), 5.07 (d, 1H, OCH$_2$Ar, J=11.6 Hz), 4.81 (d, 1H, OCH$_2$Ar, J=12 Hz), 4.50 (s, C$_5$—H), 4.46 (d, 1H, OCH$_2$Ar, J=12 Hz), 4.01-3.74 (m, 4H, OCH$_2$CH$_2$O).

A solution of 3-benzyloxy-14β-[(2-chlorobenzyl)oxy]-17-cyclopropylmethyl-4,5α-epoxymorphinan-6-spiro-2'-(1,3-dioxolane) (5.50 g, 9.16 mmol) in MeOH (52 ml) and conc. HCl (23 ml) was reflux heated for 2.5 h. After cooling with ice, the solution was alkalised with conc. NH$_4$OH and extracted with CH$_2$Cl$_2$ (1×200 ml, 1×100 ml, 2×50 ml). The combined organic phases were washed with H$_2$O, dried over Na$_2$SO$_4$ and evaporated down. The residue (5.54 g of yellowish oil) was purified using column chromatography (silica gel; CH$_2$Cl$_2$/MeOH/conc. NH$_4$OH 250:3:0.5) and in this way 2.69 g (63%) of pure 14β-[(2-chlorobenzyl)oxy]-17-cyclopropylmethyl)-4,5α-epoxy-3-hydroxymorphinan-6-one (compound 13) was obtained. A part was dissolved in ether and etherial HCl added to it. Compound 13.HCl was isolated. Fp. 165-168° C.; $^1$H-NMR (Me$_2$SO-d$_6$) δ 8.63 (br. s, OH), 7.96 (s, 1H, $^+$NH), 7.50-7.30 (m, 4 arom. H), 6.74 (d, 1 arom. H, J=8 Hz), 6.69 (d, 1 arom. H, J=8 Hz), 5.19 (s, C$_5$—H), 4.87 (d, 1H, OCH$_2$Ar, J=11.6 Hz), 4.81 (d, 1H, OCH$_2$Ar, J=11.6 Hz); Cl-MS: m/z 466 (M$^+$+1).

EXAMPLE 14

Synthesis of 14β-benzyloxy-17-cyclopropylmethyl-4,5α-epoxy-3-hydroxymorphinan-6-one (compound 14.HBr)

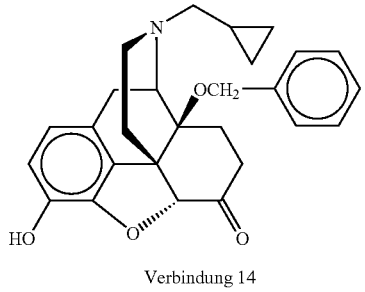

Compound 14

Verbindung 14

A solution of 3,14β-dibenzyloxy-17-cyclopropylmethyl-4,5α-epoxymorphinan-6-spiro-2'-(1,3-dioxolane) (Schmidhammer et al., Heterocycles 1998, 49, 489-497) (10.0 g, 17.68 mmol) in MeOH (200 ml)/H$_2$O (250 ml)/conc. HCl (50 ml) was reflux heated for 4 h. After cooling with ice, the solution was alkalised with conc. NH$_4$OH and extracted with CH$_2$Cl$_2$ (1×100 ml, 2×25 ml). The combined organic phases were washed with H$_2$O, dried over Na$_2$SO$_4$ and evaporated down. The residue (8.48 g of slightly brown foamy resin) was purified using column chromatography (silica gel; CH$_2$Cl$_2$/MeOH/conc. NH$_4$OH 90:9:1) and in this way 6.28 g of 3,14β-dibenzyloxy-17-cyclopropylmethyl-4,5α-epoxymorphinan-6-one (Schmidhammer et al., Heterocycles 1998, 49, 489-497) was obtained as colourless foamy resin and 1.14 g (18%) of the compound 14 as a slightly yellow foamy resin. One part of the compound 14 was converted in the usual way to the hydrobromide (compound 14.HBr) using 48% HBr. Fp. >210° C. (decomp.); $^1$H-NMR (Me$_2$SO-d$_6$) δ 9.48 (s, OH), 8.31 (s, $^+$NH), 7.56-7.32 (m, 5 arom. H), 6.72 (d, 1 arom. H, J=8 Hz), 6.68 (d, 1 arom. H, J=8 Hz), 5.10 (s, C-5H), 4.70 (d, 1H, OCH$_2$Ph, J=10.4 Hz), 4.25 (d, 1H, OCH$_2$Ph, J=10.4 Hz); Cl-MS: m/z 432 (M$^+$+1).

EXAMPLE 15

Synthesis of 14β-butoxy-17-cyclopropylmethyl-4,5α-epoxy-3-hydroxymorphinan-6-one hydrochloride (compound 15.HCl)

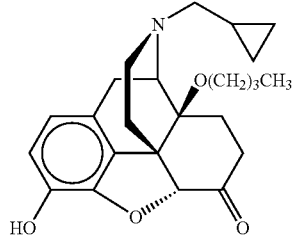

Compound 15

Verbindung 15

NaH (2.8 g, 118 mmol; obtained from 4.2 g of a 60% NaH dispersion by washing with petroleum ether) was added to an ice-cooled, stirred solution of 3-benzyloxy-17-cyclopropylmethyl-4,5α-epoxy-14β-hydroxymorphinan-6-spiro-2'-(1,3-dioxolane) (see Example 13) (10.70 g, 22.5 mmol) in 200 ml water-free N,N-dimethylformamide under N$_2$. After 15 min. trans-crotylbromide (27 mmol, 3.2 ml of an 85% trans-crotylbromide solution) was added and stirred for 3.5 h (1 h at 0-5° C., 2.5 h at room temperature). After the breakdown of excess NaH by the addition of small pieces of ice, the mixture was poured onto 500 ml H$_2$O and extracted with CH$_2$Cl$_2$ (3×100 ml, 2×50 ml). The combined organic phases were washed with H$_2$O (3×200 ml) and saturated NaCl solution, dried over Na$_2$SO$_4$ and evaporated down. The residue from the evaporation (13.85 g of yellow oil) was purified using column chromatography (silica gel; CH$_2$Cl$_2$/MeOH/conc. NH$_4$OH (250/3/0.5)). The residue from the evaporation (7.11 g of yellow oil) was dissolved in ether and 3-benzyloxy-14β-[(E)-(but-2enyl)oxy]-17-cyclopropylmethyl-4,5α-epoxy-morphinan-6-spiro-2'-(1,3-dioxolane) was precipitated as the hydrochloride by the addition of etherial HCl. Yield: 6.85 g (54%). Fp. 135-139° C.; $^1$H-NMR (DMSO-d$_6$): δ 8.11 (s, wide, $^+$NH), 7.50-7.25 (m, 5 arom. H), 6.92 (d, 1 arom. H, J=8.4 Hz), 6.68 (d; 1 arom. H, J=8.4 Hz), 5.79 (m, 2 olefin. H), 5.14 (s, 2 H, C$_3$OCH$_2$), 4.59 (s, C$_5$—H), 4.20-3.72 (m, 6 H, C$_6$—(OCH$_2$)$_2$, C$_{14}$(OCH$_2$), 1.72 (m, 3H, CH═CHC$\underline{H}$$_3$); MS (CI): m/z 530 (M$^+$+1).

A mixture of 3-benzyloxy-14β-[(E)-(but-2-enyl)oxy]-17-cyclopropylmethyl-4,5α-epoxymorphinan-6-spiro-2'-(1,3-dioxolane) hydrochloride (6.27 g, 11 mmol), 630 mg of 10% Pd/C catalyst and 100 ml MeOH was hydrogenated for 2 h at room temperature and 30 psi. Then the catalyst was filtered off and the filtrate was evaporated down in a vacuum. The evaporation residue (reddish crystals) was treated with reflux boiling MeOH. Yield: 4.17 g (79%) of colourless crystals of 14β-butoxy-17-cyclopropylmethyl-4,5α-epoxy-3-hydroxymorphinan-6-spiro-2'-(1,3-dioxolane) hydrochloride. Fp. 247-252° C.; $^1$H-NMR (DMSO-d$_6$): δ 9.23 (s, 1H, OH), 7.87 (s, wide, 1H, $^+$NH), 6.68 (d, 1 arom. H, J=8.2 Hz), 6.57 (d, 1 arom. H, J=8.2 Hz), 4.49 (s, C$_5$—H), 4.11-3.55 (m, 4H, C$_6$(OCH$_2$)$_2$), 0.95 (t, 3H, CH$_2$CH$_3$, J=7.4 Hz); MS (CI): m/z 443 (M$^+$+1).

A solution of 14β-butoxy-17-cyclopropylmethyl-4,5α-epoxy-3-hydroxymorphinan-6-spiro-2'-(1,3-dioxolane) hydrochloride (4.07 g, 8.5 mmol) in 100 ml MeOH/H$_2$O/conc. HCl (50:85:15) was reflux heated for 4 h. After the addition of H$_2$O (70 ml) and alkalisation with conc. NH$_4$OH extraction with CH$_2$Cl$_2$ (3×60 ml) occurred. The combined organic phases were washed with H$_2$O and saturated NaCl solution, dried over Na$_2$SO$_4$ and evaporated down. The evaporation residue (3.63 g of brown oil) was purified using column chromatography (silica gel; CH$_2$Cl$_2$/MeOH/conc. NH$_4$OH 250:3.5:0.5)). One part of the evaporation residue (2.71 g of colourless foamy resin, 80%) was dissolved in ether and the compound 15.HCl (2.46 g) was obtained as a pure substance by the addition of etherial HCl. Fp. 240° C. (decomp.); IR (KBr): 1725 (CO) cm$^{-1}$; $^1$H-NMR (DMSO-d$_6$): δ 9.50 (s, OH), 8.15 (s, wide, $^+$NH), 6.71 (d, 1 arom. H, J=8.0 Hz), 6.65 (d, 1 arom. H, J=8.0 Hz), 4.93 (s, C$_5$—H), 0.95 (t, 3H, CH$_2$CH$_3$, J=7.2 Hz); MS (CI): m/z 399 (M$^+$+1).

EXAMPLE 16

Synthesis of 17-cyclopropylmethyl-4,5α-epoxy-3-hydroxy-14β-[(3-methylbutyl)oxy]morphinan-6-one hydrochloride (compound 16.HCl)

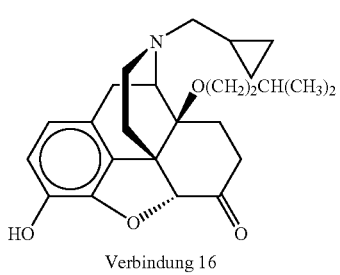

Verbindung 16

NaH (840 mg, 35 mmol; obtained from 1.4 g of a 60% NaH dispersion by washing with petroleum ether) was added to an ice-cooled, stirred solution of 3-benzyloxy-17-cyclopropylmethyl-4,5α-epoxy-14β-hydroxymorphinan-6-spiro-2'-(1,3-dioxolane) (see Example 13) (4.0 g, 8.4 mmol) in 200 ml water-free N,N-dimethylformamide under N$_2$. After 15 min. 3,3-dimethylallylbromide (1.95 ml, 16.8 mmol) was added and stirred for 19 h. (1 h at 0-5° C., 18 h at room temperature). After the breakdown of excess NaH by the addition of small pieces of ice, the mixture was poured onto 200 ml H$_2$O and extracted with CH$_2$Cl$_2$ (1×70 ml, 3×40 ml). The combined organic phases were washed with H$_2$O (3×150 ml) and saturated NaCl solution, dried over Na$_2$SO$_4$ and evaporated down. The evaporation residue (4.8 g of yellow-brown oil) was purified using column chromatography (silica gel; CH$_2$Cl$_2$/MeOH/conc. NH$_4$OH 250:3:0.5).

The oil obtained was dissolved in ether and 3-benzyloxy-17-cyclopropylmethyl-4,5α-epoxy-14β-[(3-methylbut-2-enyl)oxy]morphinan-6-spiro-2'-(1,3-dioxolane) hydrochloride was obtained as a pure substance by the addition of etherial HCl. Yield: 3.81 g (78%). Fp. 126-129° C.; $^1$H-NMR (DMSO-d$_6$): δ 8.15 (s, wide, $^+$NH), 7.45-7.25 (m, 5 arom. H), 6.92 (d, 1 arom. H, J=8.0 Hz), 6.68 (d, 1 arom. H, J=8.0 Hz), 5.51 (m, 1 olefin. H), 5.14 (s, 2H, C$_3$OCH$_2$), 4.58 (s, C$_5$—H), 3.92-3.44 (m, 4H, C$_6$(OCH$_2$)$_2$), 1.76 (s, 3H, CH=CCH$_3$); 1.67 (s, 3H, CH=CCH$_3$); MS (CI): m/z 544 (M$^+$+1).

A mixture of 3-benzyloxy-17-cyclopropylmethyl-4,5α-epoxy-14β-[(3-methylbut-2-enyl)oxy]-morphinan-6-spiro-2'-(1,3-dioxolane) hydrochloride (4.01 g, 6.9 mmol), 400 mg of 10% Pd/C catalyst and 100 ml MeOH was hydrogenated for 2.5 h at room temperature and 30 psi. Then the catalyst was filtered off and the filtrate was evaporated down. The evaporation residue was treated with ether, the insoluble portion filtered off, and etherial HCl added to the filtrate and in this way 17-cyclopropylmethyl-4,5α-epoxy-3-hydroxy-14β-[(3-methylbutyl)oxy]morphinan-6-spiro-2'-(1,3-dioxolane) hydrochloride was obtained as a pure substance. Yield: 2.24 g (66%). Fp. 191-193° C.; $^1$H-NMR (DMSO-d$_6$): δ 9.22 (s, OH), 7.83 (s, wide, $^+$NH), 6.69 (d, 1 arom. H, J=8.0 Hz), 6.58 (d, 1 arom. H, J=8.0 Hz), 4.47 (s, C$_5$—H), 4.08-3.50 (m, 4H, C$_6$(OCH$_2$)$_2$), 0.96 (d, 3H, CHCH$_3$, J=4.8 Hz); 0.92 (d, 3H, CHCH$_3$, J=4.8 Hz); MS (CI): m/z 457 (M$^+$+1).

A solution of 17-cyclopropylmethyl-4,5α-epoxy-3-hydroxy-14β-[(3-methyl-butyl)oxy]morphinan-6-spiro-2'-(1,3-dioxolane) hydrochloride (2.8 g, 5.7 mmol) in 110 ml MeOH/H$_2$O/conc. HCl (4:5:1) was reflux heated for 4.5 h. After the addition of H$_2$O (80 ml) and alkalisation with conc. NH$_4$OH extraction with CH$_2$Cl$_2$ (1×80 ml, 3×50 ml) occurred. The combined organic phases were washed with H$_2$O and saturated NaCl solution, dried over Na$_2$SO$_4$ and evaporated down. The evaporation residue (2.5 g of brown oil) was purified using column chromatography (silica gel; CH$_2$Cl$_2$/MeOH/conc. NH$_4$OH 250:3:0.5)). The evaporation residue (2.21 g of white foamy resin) was dissolved in ether and the compound 16.HCl was obtained as a pure substance by the addition of etherial HCl. Yield: 1.99 g (78%). Fp. 168-170° C.; IR (KBr): 1725 (CO) cm$^{-1}$; $^1$H-NMR (DMSO-d$_6$): δ 9.50 (s, OH), 8.08 (s, wide, $^+$NH), 6.72 (d, 1 arom. H, J=8.0 Hz), 6.66 (d, 1 arom. H, J=8.0 Hz), 4.92 (s, C$_5$—H), 0.96 (d, 3H, CHCH$_3$, J=3.8 Hz); 0.93 (d, 3H, CHCH$_3$, J=3.8 Hz); MS (CI): m/z 412 (M$^+$+1).

EXAMPLE 17

Synthesis of 4,5α-epoxy-5β,17-dimethyl-14β-[(3-phenylpropyl)oxy]-3-[(prop-2-inyl)oxy]morphinan-6-one hydrochloride (compound 17.HCl)

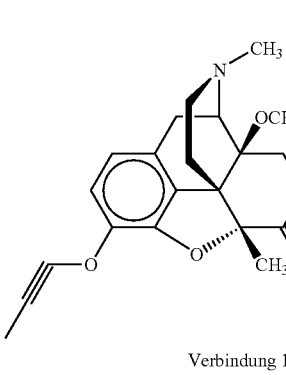

Verbindung 17

NaH (0.72 g, 30.0 mmol; obtained from 1.2 g of a 60% NaH dispersion in oil by washing with petroleum ether) was added to a solution of 14-hydroxy-5-methlycodeinone (Schmidhammer et al., Helv. Chim. Acta, 1988, 73, p. 642) (5.00 g, 15.27 mmol) in 30 ml water-free N,N-dimethylformamide under N$_2$ at 0° C. (bath temperature) under stirring. After 25 min. a solution of cinnamyl bromide (3.01 g, 15.27 mmol) in 20 ml N,N-dimethylformamide was added drop by drop and the mixture stirred for 1.5 h at 0° C. (bath temperature). Small pieces of ice were added until no more hydrogen was produced, the mixture was poured onto 500 ml H$_2$O and extracted with dichloromethane/isopropanol (4:1) (1×150 ml, 3×50 ml). The combined organic phases were washed with H$_2$O (5×400 ml) and 1× with 250 ml saturated sodium chloride solution, dried over sodium sulphate and evaporated down. The evaporation residue (7.59 g of orange coloured oil) was crystallised out of isopropanol/ether (1:1) (20 ml). Yield: 3.03 g (45%) of colourless crystals of 14-cinnamyloxy-5-methylcodeinone (=7,8-didehydro-4,5α-epoxy-3-methoxy-5β,17-dimethyl-14β-{[(E/Z)-3-phenylprop-2-enyl]oxy}morphinan-6-one). Fp. >150° C. (decomp.); IR (KBr): 1675 (CO) cm$^{-1}$; $^1$H-NMR (DMSO-d$_6$, δ in ppm): δ 7.44-7.23 (m, 5 arom. H, 1 olef. H), 6.70 (d, 1 arom. H, J=8.2 Hz), 6.62 (d, 1 arom. H, J=8.2 Hz), 6.56 (d, 1 olefin. H, —CH═CH-Ph, J=15.7 Hz)), 6.33 (dt, 1 olef. H, —CH═CH-Ph, J=15.7 Hz), 6.10 (d, 1 olef. H, J=10.0 Hz), 4.26 and 4.11 (2 dd, 2H, C-14-OCH$_2$—, J=5.0 and 10.6 Hz), 3.70 (s, CH$_3$O), 2.36 (s, CH$_3$N), 1.61 (s, C5-CH$_3$); CI-MS: m/z 444 (M$^+$+1).

A mixture of 14-cinnamyloxy-5-methylcodeinone (3.44 g, 7.76 mmol), 10% Pd/C catalyst (350 mg) and 80 ml EtOH was hydrogenated for 2 h at a temperature of 50° C. and 50 psi. Then the catalyst was filtered off, the filtrate was evaporated down and the residue (3.31 g of dark oil) was crystallised out of 10 ml EtOH. Yield: 2.52 g (73%) of 4,5α-epoxy-3-methoxy-5β,17-dimethyl-14β-[(3-phenylpropyl)oxy]morphinan-6-one (compound 17a). Fp. 126-128° C.; IR (KBr): 1720 (CO) cm$^{-1}$; $^1$H-NMR (CDCl$_3$, δ in ppm): δ 7.32-7.17 (m, 5 arom. H), 6.67 (d, 1 arom. H, J=8.2 Hz), 6.58 (d, 1 arom. H, J=8.2 Hz), 3.87 (s, CH$_3$O), 2.34 (s, CH$_3$N), 1.65 (s, C5-CH$_3$); CI-MS: m/z 448 (M$^+$+1).

A solution of 4,5α-epoxy-3-methoxy-5β,17-dimethyl-14β-[(3-phenylpropyl)oxy]morphinan-6-one (2.23 g, 4.98 mmol) in 13 ml 48% HBr was reflux heated for 20 min, then cooled and evaporated down. The evaporation residue was dissolved in 20 ml MeOH and evaporated down. The process was repeated 1×, whereby 2.48 g of beige crystals were obtained, which were recrystallised out of 15 ml MeOH. Yield: 2.26 g (88%) 4,5α-epoxy-3-hydroxy-5β,17-dimethyl-14β-[(3-phenylpropyl)oxy]morphinan-6-one hydrobromide (compound 17b.HBr). Fp. >270° C. (decomp.); IR (KBr): 1720 (CO) cm$^{-1}$; $^1$H-NMR (DMSO-d$_6$, δ in ppm): δ 9.42 (s, OH), 8.58 (s, $^+$NH), 7.36-7.16 (m, 5 arom. H), 6.69 (d, 1 arom. H, J=8.2 Hz), 6.64 (d, 1 arom. H, J=8.2 Hz), 2.97 (s, CH$_3$N), 1.65 (s, C5-CH$_3$); CI-MS: m/z 434 (M$^+$+1).

A mixture of 4,5α-epoxy-3-hydroxy-5β,17-dimethyl-14β-[(3-phenylpropyl)oxy]morphinan-6-one hydrobromide (380 mg, 0.88 mmol), calcium carbonate (370 mg, 2.68 mmol), propargylbromide (0.20 ml, 2.66 mmol) and 25 ml acetone was reflux heated under N$_2$ for 7 h. The inorganic material was filtered off, the filtrate evaporated down and the residue (460 mg of orange coloured oil) was purified using column chromatography (silica gel; CH$_2$Cl$_2$/MeOH/conc. NH$_4$OH 250:2:0.5). The evaporation residue (350 mg of yellow oil) was dissolved in ether and etherial HCl was added to it, whereby 220 mg (49%) of the compound 17.HCl was obtained. Fp. >130-133° C.; IR (KBr): 1727 (CO) cm$^{-1}$; $^1$H-NMR (DMSO-d$_6$, δ in ppm): δ 9.38 (s, $^+$NH), 7.34-7.19 (m, 5 arom. H), 6.92 (d, 1 arom. H, J=8.4 Hz), 6.78 (d, 1 arom. H, J=8.4 Hz), 4.81 (d, 2H, HCCCH$_2$O—C3, J=1 Hz), 3.59 (d, 1H, HCCCH$_2$O—C3, J=1 Hz), 2.94 (s, CH$_3$N), 1.53 (s, C5-CH$_3$); CI-MS: m/z 472 (M$^+$+1).

EXAMPLE 18

Synthesis of 14β-[(3-chlorobenzyl)oxy]-4,5α-epoxy-17-methyl-3-[(prop-2-inyl)oxy]-morphinan-6-one hydrochloride (18.HCl)

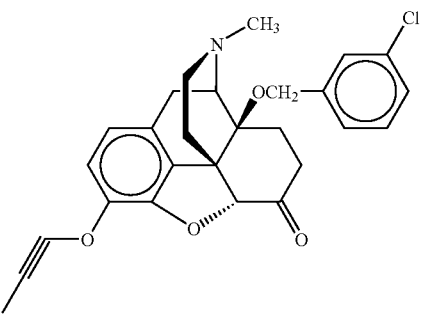

Compound 18

Verbindung 18

NaH (1.60 g, 66.76 mmol; obtained from 2.67 g of a 60% NaH dispersion by washing with petroleum ether) was added to a solution of 4,5α-epoxy-14β-hydroxy-3-methoxy-17-methylmorphinan-6-spiro-2'-(1,3-dioxolane) (Lester et al., Tetrahedron 1965, 21. pp. 771-778) (6.00 g, 16.69 mmol) in 100 ml water-free N,N-dimethylformamide under N$_2$ at 0° C. (bath temperature) under stirring. After 15 min. 3-chlorobenzylbromide (4.4 ml, 33.38 mmol) was added and stirred for 24 h (1 h at 0-5° C., 23 h at room temperature). After the breakdown of excess NaH by adding small pieces of ice, the mixture was poured onto 300 ml H$_2$O and extracted with CH$_2$Cl$_2$ (1×100 ml, 3×40 ml). The combined organic phases were washed with H$_2$O (4×200 ml) and saturated NaCl solution, dried over Na$_2$SO$_4$ and evaporated down. The evaporation residue (13.36 g of yellow oil) was crystallised out of MeOH and recrystallised. Yield: 4.29 g (53%) of 14β-[(3-chlorobenzyl)oxy]-4,5α-epoxy-3-methoxy-17-methylmorphinan-6-spiro-2'-(1,3-dioxolane) as colourless crystals. Fp. 131-133° C.; $^1$H-NMR (DMSO-d$_6$): δ 7.58-7.26 (m, 4 arom. H), 6.74 (d, 1 arom. H, J=8.1 Hz), 6.60 (d, 1 arom. H, J=8.1 Hz), 4.55 (d, 1H, C$_{14}$OCH$_2$, J=11.8 Hz), 4.31 (d, 1H, C$_{14}$OCH$_2$, J=11.8 Hz), 4.42 (s, C$_5$—H), 4.10-3.61 (m, 4H, C$_6$(OCH$_2$)$_2$), 3.78 (s, OCH$_3$), 2.30 (s, NCH$_3$); MS (CI): m/z 485 (M$^+$+1).

A mixture of 14β-[(3-chlorobenzyl)oxy]-4,5α-epoxy-3-methoxy-17-methylmorphinan-6-spiro-2'-(1,3-dioxolane) (3.00 g, 6.2 mmol), sodium ethane thiolate (2.32 g, 27.6 mmol) and 30 ml of water-free N,N-dimethylformamide was stirred for 5 h under N$_2$ at 130° C. (bath temperature) and then poured onto 400 ml H$_2$O and extracted with CH$_2$Cl$_2$ (1×100 ml, 3×60 ml). The combined organic phases were washed with H$_2$O (4×200 ml) and saturated NaCl solution, dried over Na$_2$SO$_4$ and evaporated down. The evaporation residue (3.36 g of dark brown oil 14β-[(3-chlorobenzyl)oxy]-4,5α-epoxy-3-hydroxy-17-methylmorphinan-6-spiro-2'-(1,3-dioxolane)) could not be crystallised. Therefore one part (2.8 g) was used without further purification for representing 14β-[(3-chlorobenzyl)oxy]-4,5α-epoxy-3-hydroxy-17-methylmorphinan-6-one. The remainder (414 mg) was purified using column chromatography (silica gel; CH$_2$Cl$_2$/MeOH/conc. NH$_4$OH (250:2:0.5)). The evaporation residue (352 mg of yellow oil) was dissolved in ether and 14β-[(3-chlorobenzyl)oxy]-4,5α-epoxy-3-hydroxy-17-methylmorphinan-6-spiro-2'-(1,3-dioxolane) hydrochloride (250 mg) was precipitated as a pure substance by the addition of etherial HCl. Fp. 202-205° C.; $^1$H-NMR (DMSO-d$_6$): δ 9.28 (s, OH), 8.92 (s, wide, $^+$NH), 7.60-7.36 (m, 4 arom. H), 6.70 (d, 1 arom. H, J=8.2 Hz), 6.60 (d, 1 arom. H, J=8.2 Hz), 4.59 (s, C$_5$—H), 4.76 (d, 1H, C$_{14}$OCH$_2$, J=11.9 Hz), 4.57 (d, 1H, C$_{14}$OCH$_2$, J=11.9

Hz), 4.11-3.61 (m, 4H, C$_6$(OCH$_2$)$_2$), 2.88 (d, $^+$NCH$_3$, J=4.6 Hz); MS (CI): m/z 471 (M$^+$+1).

A solution of unpurified 14β-[(3-chlorobenzyl)oxy]-4,5α-epoxy-3-hydroxy-17-methylmorphinan-6-spiro-2'-(1,3-dioxolane) (2.8 g of dark brown oil) in 100 ml MeOH/H$_2$O/conc. HCl (4:5:1) was reflux heated for 7 h. After the addition of ice-water and alkalisation with conc. NH$_4$OH extraction took place with CH$_2$Cl$_2$ (3×60 ml). The combined organic phases were washed with H$_2$O (3×100 ml) and saturated NaCl solution, dried over Na$_2$SO$_4$ and evaporated down. From the evaporation residue (1.94 g of brown foamy resin 14β-[(3-chlorobenzyl)oxy]-4,5α-epoxy-3-hydroxy-17-methyl-morphinan-6-one) one part (1.50 g) was used for further syntheses without further purification. The remainder (443 mg) was purified using column chromatography (silica gel; CH$_2$Cl$_2$/MeOH/conc. NH$_4$OH (250:4:0.5)). The evaporation residue (353 mg of yellow foamy resin) was dissolved in ether and 14β-[(3-chlorobenzyl)oxy]-4,5α-epoxy-3-hydroxy-17-methylmorphinan-6-one hydrochloride (335 mg) was precipitated as a pure substance by the addition of etherial HCl. Fp. 205-210° C.; IR (KBr): 1724 (CO) cm$^{-1}$; $^1$H-NMR (DMSO-d$_6$): δ 9.55 (s, OH), 9.15 (s, wide, $^+$NH), 7.70-7.25 (m, 4 arom. H), 6.73 (d, 1 arom. H, J=8 Hz), 6.67 (d, 1 arom. H, J=8 Hz), 5.10 (s, C$_5$—H), 4.87 (d, 1H, OCH$_2$), J=12.4 Hz), 4.68 (d, 1H, OCH$_2$), J=12.4 Hz, 2.93 (d, $^+$NCH$_3$, J=4.6 Hz); MS (CI): m/z 427 (M$^+$+1).

A mixture of unpurified 14β-[(3-chlorobenzyl)oxy]-4,5α-epoxy-3-hydroxy-17-methylmorphinan-6-one (500 mg of brown foamy resin), K$_2$CO$_3$ (485 mg, 3.51 mmol) and propargylbromide (0.26 ml, 3.51 mmol) and 40 ml acetone (with 0.5% H$_2$O) was reflux heated under N$_2$ for 3 h. After cooling the inorganic material was filtered off, washed with CH$_2$Cl$_2$ and the filtrate evaporated down. The evaporation residue (538 mg of brown oil) was purified using column chromatography (silica gel; CH$_2$Cl$_2$/MeOH/conc. NH$_4$OH (250:2:0.5)). The evaporation residue (337 mg of yellow oil) was dissolved in ether and 18.HCl was precipitated as a pure substance by the addition of etherial HCl. Yield: 347 mg (74%). Fp. 145-150° C.; IR (KBr): 1717 (CO), 2118 (C≡C) cm$^{-1}$; $^1$H-NMR (DMSO-d$_6$): δ 9.21 (s, wide, $^+$NH), 7.71-7.32 (m, 4 arom. H), 6.96 (d, 1 arom. H, J=8.4 Hz), 6.82 (d, 1 arom. H, J=8.4 Hz), 5.20 (s, C$_5$—H), 4.89 (d, 1H, C$_{14}$OCH$_2$, J=12.1 Hz), 4.69 (d, 1H, C$_{14}$OCH$_2$, J=12.1 Hz), 4.84 (d, 2H, C$_3$OCH$_2$, J=2.2 Hz), 3.58 (t, 1H, C≡CH, J=2.2 Hz), 2.94 (d, $^+$NCH$_3$, J=4.4 Hz); MS (CI): m/z 465 (M$^+$+1).

EXAMPLE 19

Synthesis of 4,5α-epoxy-17-ethyl-3-methoxy-14β-[(3-phenylpropyl)oxy]morphinan-6-one (compound 19)

Compound 19

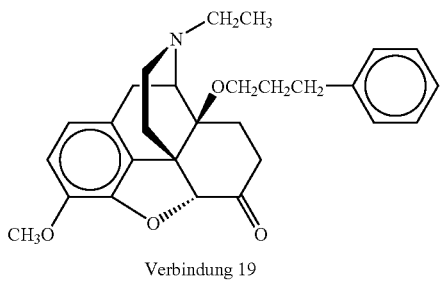

Verbindung 19

A mixture of 4,5α-epoxy-3-methoxy-14β-[(3-phenylpropyl)oxy]morphinan-6-one hydrochloride (see Example 1) (4.0 g, 8.77 mmol), K$_2$CO$_3$ (8.0 g, 57.89 mmol), ethyl iodide (0.99 ml, 12.40 mmol) and 50 ml of water-free N,N-dimethylformamide was stirred for 5 h under N$_2$ at 80° C. (bath temperature). After filtration from the inorganic residue, the filtrate was evaporated down and the residue (4.7 g of brown oil) was purified using column chromatography (silica gel; CH$_2$Cl$_2$/MeOH/conc. NH$_4$OH: 8 l: (250/2/0.5)); 0.5 l: (250/3/0.5), (250/4/0.5), (250/6/0.5), (250/8/0.5), (250/10/0.5)). The evaporation residue (1.3 g of bright yellow oil) was crystallised out of MeOH. Yield: 1.2 g (30%) of compound 19. Fp. 95-101° C.; IR (KBr): 1719 (C=O) cm$^{-1}$; $^1$H-NMR (DMSO-d$_6$): δ 7.30-7.13 (m, 5 arom. H), 6.73 (d, J=8.2 Hz, 1 arom. H), 6.64 (d, J=8.2 Hz, 1 arom. H), 4.76 (s, 1H, C$_5$—H), 3.78 (s, 3H, OCH$_3$), 0.96 (t, 3H, N—CH$_2$—CH$_3$), J=7 Hz); MS (CI): m/z 448 (M$^+$+1).

EXAMPLE 20

Synthesis of 4,5α-epoxy-17-ethyl-3-hydroxy-14β-[(3-phenylpropyl)oxy]morphinan-6-one hydrochloride (compound 20.HCl)

Compound 20

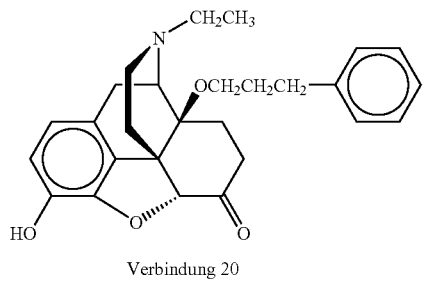

Verbindung 20

A solution of compound 19 (1.0 g, 2.23 mmol) in 48% HBr (10 ml) was reflux heated for 13 minutes. After cooling it was diluted with water (50 ml), ice was added, it was alkalised with conc. NH$_4$OH and extracted with CH$_2$Cl$_2$ (5×50 ml). The combined organic phases were washed with water (3×50 ml) and NaCl solution (1×50 ml), dried over Na$_2$SO$_4$ and evaporated down. The evaporation residue (1.3 g of brown foamy resin) was purified using column chromatography (silica gel; CH$_2$Cl$_2$/MeOH/conc. NH$_4$OH (250:2:0.5)). The evaporation residue (448 mg of yellow foamy resin) was dissolved in ether, etherial HCl added and the compound 20.HCl isolated. Yield: 380 mg (36%). Fp. 178-180° C.; IR (KBr): 1724 (C=O) cm$^{-1}$; $^1$H-NMR (DMSO-d$_6$): δ 9.14 (s, OH), 7.29-7.03 (m, 5 arom. H), 6.56 (d, 1 arom. H, J=8 Hz), 6.50 (d, 1 arom. H, J=8 Hz), 4.69 (s, C$_5$—H), 0.96 (t, 3H, N—CH$_2$—CH$_3$), J=7.2 Hz); MS (CI): m/z 434 (M$^+$+1).

EXAMPLE 21

Synthesis of 4,5α-epoxy-3-hydroxy-14β-[(3-methylbutyl)oxy]-17-propylmorphinan-6-one hydrochloride (compound 21.HCl)

Compound 21

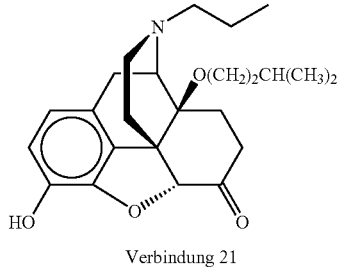

Verbindung 21

A solution of naloxone.HCl.2H$_2$O (20.0 g, 50.0 mmol) and methane sulphonic acid (3.9 ml, 60.0 mmol) in 150 ml ethylene glycol was stirred for 18 h at a bath temperature of 80-90° C. under $N_2$. After the addition of 200 ml of ice-water and alkalising with conc. $NH_4OH$ extraction took place with $CH_2Cl_2$ (2×100 ml, 2×50 ml). The combined organic phases were washed with $H_2O$ (2×100 ml) and saturated NaCl solution, dried over $Na_2SO_4$ and evaporated down. The evaporation residue (beige crystals) was treated with boiling MeOH, whereby 16.52 g (89%) of colourless crystals of 4,5α-epoxy-3,14β-dihydroxy-17-(prop-2-enyl)morphinan-6-spiro-2'-(1,3-dioxolane) was obtained. Fp. 244-247° C.; $^1$H-NMR (DMSO-$d_6$): δ 8.87 (s, $C_3$—OH), 6.54 (d, 1 arom. H, J=8 Hz), 6.44 (d, 1 arom. H, J=8 Hz), 5.93-5.70 (m, 1 olef. H), 5.27-5.04 (m, 2 olef. H), 4.79 (s, $C_{14}$—OH), 4.33 (s, $C_5$—H), 4.11-3.61 (m, 4H, $C_6(OCH_2)_2$); MS (CI): m/z 372 ($M^+$+1).

A mixture, consisting of 4,5α-epoxy-3,14β-dihydroxy-17-(prop-2-enyl)morphinan-6-spiro-2'-(1,3-dioxolane) (16.0 g, 43.1 mmol), $K_2CO_3$ (16.2 g, 117 mmol), benzyl bromide (5.63 ml, 47.4 mmol) and 80 ml of water-free N,N-dimethylformamide was stirred for 24 h under $N_2$ at room temperature. The inorganic material was filtered off, rinsed with $CH_2Cl_2$ and the filtrate was evaporated down. The evaporation residue (white crystals) was treated for 1 h with reflux boiling ether to remove the solvent and the benzylbromide. The cooled mixture was filtered off, the remaining crystals washed again with a little cold ether and then treated with reflux boiling MeOH. 12.53 g (63%) of 3-benzyloxy-4,5α-epoxy-14β-hydroxy-17-(prop-2-enyl)morphinan-6-spiro-2'-(1,3-dioxolane) was obtained as colourless crystals. Fp. 142-144° C.; $^1$H-NMR (DMSO-$d_6$): δ 7.50-7.22 (m, 5 arom. H), 6.77 (d, 1 arom. H, J=8.0 Hz), 6.56 (d, 1 arom. H, J=8.0 Hz), 5.95-5.68 (m, 1H, 1 olef. H), 5.30-5.01 (m, 4H, 2 olef. H, $C_3OCH_2$), 4.81 (s, OH), 4.40 (s, $C_5$—H), 4.08-3.65 (m, 4H, $C_6(OCH_2)_2$); MS (CI): m/z 463 ($M^+$+1).

NaH (650 mg, 27 mmol) (obtained from 1.1 g of a 60% NaH dispersion in oil by washing with petroleum ether) was added to a solution of 3-benzyloxy-4,5α-epoxy-14β-hydroxy-17-(prop-2-enyl)morphinan-6-spiro-2'-(1,3-dioxolane) (5.00 g, 10.83 mmol) in 40 ml water-free N,N-dimethylformamide under $N_2$ at 0° C. (bath temperature) under stirring. After 15 min. 3,3-dimethylallylbromide (1.90 ml, 16.25 mmol) was added and the mixture first stirred for 1 h at 0° C. (bath temperature) and then with reducing cooling stirred further for 4 hours. To terminate the reaction pieces of ice were added until no more hydrogen was produced. The mixture was poured onto 100 ml water and extracted with dichloromethane (3×100 ml). The combined organic phases were washed with $H_2O$ (3×100 ml) and 250 ml of saturated sodium chloride solution, dried over sodium sulphate and evaporated down. The evaporation residue (6.02 g of yellow oil),was purified using column chromatography (silica gel; $CH_2Cl_2$/MeOH/conc. $NH_4OH$ (250:2:0.5)). The evaporation residue (5.01 g of bright yellow oil) was dissolved in ether and pure 3-benzyloxy-4,5α-epoxy-14β-[(3-methylbut-2-enyl)oxy-17-(prop-2-enyl)morphinan-6-spiro-2'-(1,3-dioxolane) hydrochloride was precipitated by the addition of etherial HCl. Yield: 4.83 g (79%); Fp. 122-124° C.; $^1$H-NMR (DMSO-$d_6$): δ 8.61 (s, wide, $^+$NH), 7.50-7.25 (m, 5 arom. H), 6.92 (d, J=8.4 Hz, 1 arom. H), 6.70 (d, $^3$J=8.4 Hz, 1 arom. H), 5.99-5.41 (m, 4 olefin. H), 5.14 (s, $C_3$—$OCH_2$), 4.57 (s, $C_5$—H), 1.75 (s, 3H, CH=CC$\underline{H}_3$), 1.66 (s, 3H, CH=CC$\underline{H}_3$); MS (CI): m/z 531 ($M^+$+1).

A mixture of 3-benzyloxy-4,5α-epoxy-14β-[(3-methylbut-2-enyl)oxy]-17-(prop-2-enyl)morphinan-6-spiro-2'-(1,3-dioxolane) hydrochloride (4.59 g, 8.11 mmol), 460 mg 10% Pd/C catalyst and 100 ml MeOH was hydrogenated for 4 h at room temperature and 30 psi. Then the catalyst was filtered off and the filtrate was evaporated down in a vacuum. The evaporation residue (slightly grey crystals) was recrystallised out of MeOH/$Et_2O$. Yield: 3.54 g (91%) of pure 4,5α-epoxy-3-hydroxy-14β-[(3-methylbutyl)oxy]-17-propylmorphinan-6-spiro-2'-(1,3-dioxolane) hydrochloride. Fp. 176-185° C.; $^1$H-NMR (DMSO-$d_6$): δ 9.22 (s, OH), 8.12 (s, wide, 1H, $^+$NH), 6.68 (d, J=8.0 Hz, 1 arom. H), 6.58 (d, J=8.0 Hz, 1 arom. H), 4.46 (s, 1H, $C_5$—H), 4.11-3.62 (m, 4H, $C_6(OCH_2)_2$), 0.99-0.85 (m, 9H, $N^+(CH_2)_2C\underline{H}_3$, CH(C$\underline{H}_3$)$_2$); MS (CI): m/z 445 ($M^+$+1).

A solution of 4,5α-epoxy-3-hydroxy-14β-[(3-methylbutyl)oxy]-17-propylmorphinan-6-spiro-2'-(1,3-dioxolane) hydrochloride (3.40 g, 7.1 mmol) in 40 ml MeOH/$H_2O$/conc. HCl (50:85:15) was reflux heated for 4 h. After the addition of $H_2O$ (50 ml) and alkalising with conc. $NH_4OH$ extraction was carried out with $CH_2Cl_2$ (3×60 ml). The combined organic phases were washed with $H_2O$ (2×100 ml) and saturated NaCl solution, dried over $Na_2SO_4$ and evaporated down. The evaporation residue (2.61 g of dark brown oil) was purified using column chromatography (silica gel; $CH_2Cl_2$/MeOH/ conc. $NH_4OH$ (250:3:0.5)). From the evaporation residue (1.77 g of white foamy resin, 62%) a part (1.39 g) was dissolved in ether and 21.HCl (1.42 g) precipitated as a pure substance by the addition of etherial HCl. Fp. 175-185° C. (decomp.); IR (KBr): 1725 (CO) $cm^{-1}$; $^1$H-NMR (DMSO-$d_6$): δ 9.52 (s, OH), 8.33 (s, wide, $^+$NH), 6.70 (d; 1 arom. H, J=8.2 Hz), 6.65 (d, 1 arom. H, J=8.2 Hz), 4.91 (s, $C_5$—H), 1.00-0.85 (m, 9H, $N^+(CH_2)_2C\underline{H}_3$, CH(C$\underline{H}_3$)$_2$); MS (CI): m/z 401 ($M^+$+1).

EXAMPLE 22

Synthesis of 5β-benzyl-14-methoxycodeinone hydrochloride (=5β-benzyl-7,8-didehydro-4,5α-epoxy-3,14β-dimethoxy-17-methyl-morphinan-6-one hydrochloride) (compound 22.HCl)

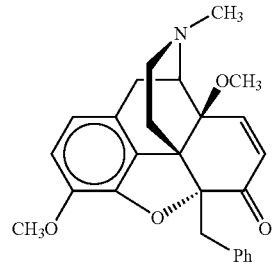

Compound 22

Verbindung 22

NaH (1.2 g, 50 mmol) (obtained from 2.0 g of a 60% NaH dispersion in oil by washing with petroleum ether) was added to a solution of 5β-benzyl-14-hydroxycodeinone (M. Gates et al., J. Org. Chem. 1989, 54, pp. 972-974) (7.95 g, 19.7 mmol) in 100 ml water-free N,N-dimethylformamide under $N_2$ at 0° C. (bath temperature) under stirring. After 15 min. dimethylsulphate (2.43 ml, 25.6 mmol) was added and the mixture stirred for 1 h at 0° C. (bath temperature). To terminate the reaction pieces of ice were added until no more hydrogen was produced. The mixture was poured onto 250 ml water and extracted with dichloromethane (3×100 ml). The combined organic phases were washed with $H_2O$ (1×100 ml, 3×60 ml) and saturated sodium chloride solution, dried over sodium sulphate and evaporated down. From the evaporation residue (8.3 g of yellow-brown oil) a part was used further unmodified and the remainder (500 mg) purified using column chromatography (silica gel; $CH_2Cl_2$/MeOH/conc. $NH_4OH$ (250: 20.5)). The evaporation residue (210 mg of yellow oil) was dissolved in ether and pure compound 22.HCl was precipitated by the addition of etherial HCl. Yield: 148 mg. Fp. 164-166° C.; IR (KBr): 1680 (CO) cm$^{-1}$; $^1$H-NMR (DMSO-d$_6$): δ 9.47 (s, wide, $^+$NH), 7.37-7.09 (m, 5 arom. H), 7.04 (d, 1H, C$_8$H, J=10.0 Hz), 6.84 (d, 1 arom. H, J=8.4 Hz), 6.74 (d, 1 arom. H, J=8.4 Hz), 6.29 (d, 1H, C$_7$—H, J=10.0 Hz), 3.76 (s, 3H, C$_3$OCH$_3$), 3.59 (d, 1H, C$_5$—CH$_2$, J=15.1 Hz), 3.29 (d, 1H, C$_5$—CH$_2$), J=15.1 Hz), 2.98 (s, 3H, C$_{14}$—OCH$_3$), 2.88 (d, 3H, $^+$NCH$_3$, J=4.6 Hz); MS (CI): m/z 419 (M$^+$+1).

EXAMPLE 23

Synthesis of 5β-benzyl-4,5α-epoxy-3,14β-dimethoxy-17-methylmorphinan-6-one (compound 23)

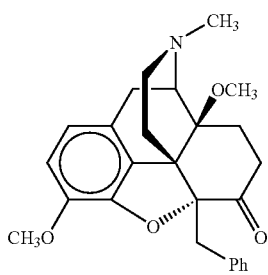

Compound 23

Verbindung 23

A mixture of unpurified compound 22 (6.96 g, 16.7 mmol of yellow-brown oil), 0.7 g 10% Pd/C catalyst and 150 ml MeOH was hydrogenated for 3 h at room temperature and 30 psi. Then the catalyst was filtered off and the filtrate was evaporated down in a vacuum. The evaporation residue (light brown foamy resin) was recrystallised out of isopropanol, whereby 3.14 g (45%) of pure compound 23 was obtained. Fp. 136-138° C.; IR (KBr): 1725 (CO) cm$^{-1}$; $^1$H-NMR (CDCl$_3$): δ 7.35-7.18 (m, 5 arom. H), 6.66 (d, 1 arom. H, J=8.2 Hz), 6.57 (d, 1 arom. H, J=8.2 Hz), 3.90 (s, C$_3$—OCH$_3$), 3.48 (s, 2H, C$_5$—CH$_2$), 3.34 (s, C$_{14}$—OCH$_3$), 2.42 (s, NCH$_3$); MS (CI): m/z 421 (M$^+$+1).

EXAMPLE 24

Synthesis of 5β-benzyl-4,5α-epoxy-3-hydroxy-14β-methoxy-17-methylmorphinan-6-one hydrochloride (compound 24.HCl)

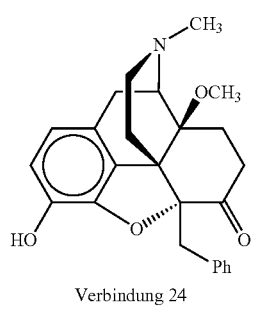

Compound 24

Verbindung 24

A solution of compound 23 (2.90 g, 6.9 mmol) in 40 ml of 48% hydrobromic acid was reflux heated for 15 min. Then the solution was cooled and evaporated down. The evaporation residue was dissolved in MeOH and again evaporated down. The resulting foamy resin (2.50 g) was converted to the base and purified using column chromatography (silica gel; CH$_2$Cl$_2$/MeOH/conc. NH$_4$OH (250:3:0.5)). The evaporation residue (2.27 g of yellow oil) was dissolved in ether and the pure compound 24.HCl precipitated with etherial HCl. Yield: 2.30 g (75%); Fp. 222-224° C.; IR (KBr): 1725 (CO) cm$^{-1}$; $^1$H-NMR (DMSO-d$_6$): δ 9.45 (s, OH), 9.38 (s, wide, +NH), 7.37-7.09 (m, 5 arom. H), 6.70 (d, 1 arom. H, J=8.2 Hz), 6.62 (d, 1 arom. H, J=8.2 Hz), 3.41 (s, OCH$_3$), 2.89 (d, 3H, $^+$NCH$_3$, J=3.4 HZ); MS (CI): m/z 407 (M$^+$+1).

EXAMPLE 25

Synthesis of 4-hydroxy-3-methoxy-17-methyl-14-[(3-phenylpropyl)oxy]-morphinan-6-one (compound 25)

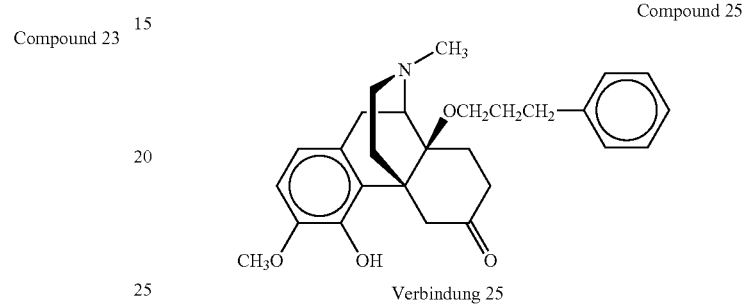

Compound 25

Verbindung 25

A mixture of 4,5α-epoxy-3-methoxy-17-methyl-14-[(3-phenylpropyl)oxy]-morphinan-6-one (=14-O-(3-phenylpropyl)oxycodon) (see Example 1) (600 mg, 1.4 mmol), ammonium chloride (0.97 g, 18.0 mmol) and 30 ml MeOH was reflux heated under stirring. Then within 5 minutes activated zinc powder (0.94 g, 14.0 mmol) was added in portions and the mixture reflux heated for 6 h. After filtration from the inorganic residue, the filtrate was evaporated down, alkalised with conc. NH$_4$OH, extracted with CH$_2$Cl$_2$ (3×40 ml), washed with H$_2$O, dried over Na$_2$SO$_4$ and evaporated down. The evaporation residue (605 mg) was crystallised out of a little MeOH. Yield: 562 mg (86%) of compound 25. Fp. >258° C. (decomp.); IR (KBr): 3145 (OH), 1734 (CO) cm$^{-1}$; $^1$H-NMR (CDCl$_3$): δ 7.37-7.05 (m, 5 arom. H), 6.64 (d, 1 arom. H, J=8.3 Hz), 6.54 (d, 1 arom. H, J=8.3 Hz), 3.79 (s, OCH$_3$), 2.30 (s, NCH$_3$); MS (CI): m/z 436 (M$^+$+1).

EXAMPLE 26

Synthesis of 3,4-dimethoxy-17-methyl-14-[(3-phenylpropyl)oxy]morphinan-6-one salicylate (compound 26, C$_7$H$_6$O$_3$)

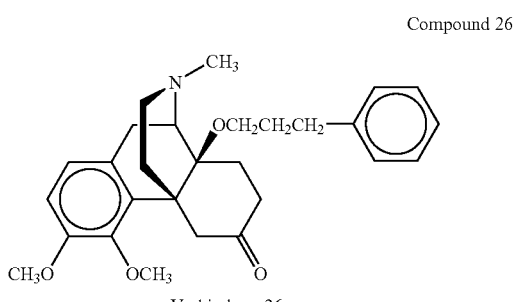

Compound 26

Verbindung 26

A mixture of compound 25 (200 mg, 0.5 mmol), K$_2$CO$_3$ (420 mg, 3.0 mmol) and phenyltrimethyl ammonium chloride (254 mg, 1.5 mmol) and 50 ml water-free N,N-dimethylformamide was stirred for 9 h at 80° C. (bath temperature) under $N_2$. After filtration from the inorganic residue, the filtrate was evaporated down, and the evaporation residue was purified using column chromatography (silica gel; $CH_2Cl_2$/MeOH/conc. $NH_4OH$ (93:7:1)). The evaporation residue (250 mg of foamy resin) was dissolved in MeOH and salicylic acid added to it. 102 mg (41%) of the compound 26.$C_7H_6O_3$ was isolated. Fp. 110-115° C.; IR (KBr): 1720 (CO) cm$^{-1}$; $^1$H-NMR (CDCl$_3$): δ 7.29-7.18 (m, 5 arom. H), 6.75, (s, 2 arom. H), 3.93 (s, $C_4$—OCH$_3$), 3.80 (s, $C_3$—OCH$_3$), 2.31 (s, NCH$_3$); MS (CI): m/z 450 (M$^+$+1).

EXAMPLE 27

Synthesis of 14β-benzyloxy-4-hydroxy-3-methoxy-17-methylmorphinan-6-one hydrochloride (compound 27.HCl)

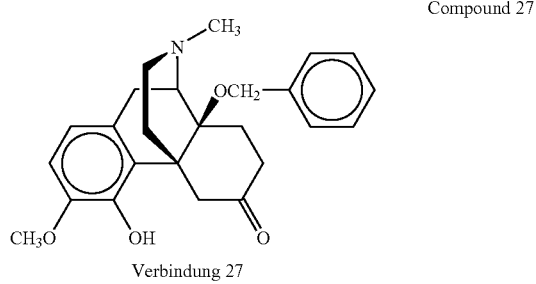

Verbindung 27

A mixture of 4,5α-epoxy-14β-hydroxy-3-methoxy-17-methylmorphinan-6-spiro-2'-(1,3-dioxolane) (Lester et al. 1965, 21, p. 771) (6.0 g, 16.69 mmol), NaH (2.16 g, 90.0 mmol), obtained from 3.6 g of 60% dispersion by washing with petroleum ether) and 150 ml water-free N,N-dimethylformamide was stirred for 20 min. at 0° C. (bath temperature) under $N_2$. After the addition of benzylbromide (4.0 ml, 33.39 mmol) it was stirred further for 16 h at room temperature. Then pieces of ice were added until no more $H_2$ was given off, it was diluted with water (100 ml) and extracted with $CH_2Cl_2$ (1×250 ml, 3×150 ml, 1×100 ml). The combined organic phases were washed with water (4×250 ml) and NaCl solution (1×250 ml), dried over $Na_2SO_4$ and evaporated down. The evaporation residue (7.47 g of red-brown oil) was crystallised out of MeOH (12 ml). 6.01 g of colourless 4,5α-epoxy-14β-benzyloxy-3-methoxy-17-methylmorphinan-6-spiro-2'-(1,3-dioxolane) was isolated. The mother liquor was evaporated down and purified using column chromatography (silica gel; $CH_2Cl_2$/MeOH/conc. $NH_4OH$: 2 l: (250/2/0.5); each 1 l: (250/4/0.5), (250/6/0.5), (250/8/0.5), (250/10/0.5)). The evaporation residue (551 mg, bright yellow oil) was crystallised out of MeOH (1 ml). Total yield: 6.32 g (84%) of 4,5α-epoxy-14β-benzyloxy-3-methoxy-17-methylmorphinan-6-spiro-2'-(1,3-dioxolane). Fp. 121-124° C.; $^1$H-NMR (DMSO-d$_6$): δ 7.44-7.26 (m, 5 arom. H), 6.74 (d, 1 arom. H, J=8.2 Hz), 6.60 (d, 1 arom. H, J=8.2 Hz), 4.55 (d, 1 aliph. H, 14-O—$\underline{CH_2}$.$C_6H_5$, J=11.2 Hz), 4.41 (s, $C_5$—H), 4.31 (d, 1 aliph. H, 14-O—$\underline{CH_2}$—$C_6H_5$, J=11.2 Hz), 4.02-3.67 (m, 4H, OCH$_2$CH$_2$O), 3.77 (s, OCH$_3$); 2.31 (s, NCH$_3$); MS (CI): m/z 450 (M$^+$+1).

A solution of 4,5α-epoxy-14β-benzyloxy-3-methoxy-17-methylmorphinan-6-spiro-2'-(1,3-dioxolane) (957 mg, 2.13 mmol) in MeOH (15 ml) and 2N HCl (22.5 ml) was reflux heated for 4 h. After cooling, it was diluted with water (20 ml), alkalised with conc. $NH_4OH$ and extracted with $CH_2Cl_2$ (1×100 ml, 1×50 ml, 3×25 ml). The combined organic phases were washed with water (1×100 ml) and NaCl solution (1×100 ml), dried over $Na_2SO_4$ and evaporated down. The evaporation residue (879 mg of dark yellow oil) was crystallised out of MeOH. Yield: 801 mg (89%) of 14β-benzyloxy-4,5α-expoxy-3-methoxy-17-methylmorphinan-6-one. Fp. 136-138° C.; IR (KBr): 1721 (CO) cm$^{-1}$; $^1$H-NMR (CDCl$_3$): δ 7.45-7.24 (m, 5 arom. H), 6.68 (d, 1 arom. H, J=8.3 Hz), 6.62 (d, 1 arom. H, J=8.3 Hz), 4.77 (d, 1H, OCH$_2$Ph, J=10.3 Hz), 4.64 (s, CH-5), 4.37 (d, 1H, OCH$_2$Ph, J=10.3 Hz), 3.88 (s, CH$_3$O), 2.39 (s, CH$_3$N); MS (CI): m/z 406 (M$^+$+1).

Zinc powder was carefully added in portions (totalling 1.4 g, 21.45 mmol) to a reflux boiling mixture of 14β-benzyloxy-4,5α-expoxy-3-methoxy-17-methylmorphinan-6-one (870 mg, 2.15 mmol), $NH_4Cl$ (1.4 g, 26.21 mmol) and MeOH (40 ml) under stirring. The mixture was reflux heated for 2 h. After filtration from the inorganic material, the filtrate was evaporated down, water (40 ml) was added to the evaporation residue, extracted with a mixture of $CH_2Cl_2$ and isopropanol (3:1) (3× each with 40 ml), the combined organic phases washed with water (1×20 ml) and NaCl solution (1×20 ml), dried over $Na_2SO_4$ and evaporated down. The evaporation residue (961 mg of white foamy resin) was purified using column chromatography (silica gel; $CH_2Cl_2$/MeOH/conc. $NH_4OH$ (250:4:0.5)). The evaporation residue (750 mg) was dissolved in ether and etherial HCl added to it. Yield: 730 mg (77%) of compound 27.HCl. Fp. >220-224° C. (decomp.); IR (KBr): 1714 (C=O) cm$^{-1}$; $^1$H-NMR (DMSO-d$_6$): δ 9.26 (s, wide, $^+$NH), 8.84 (s, C4-OH), 7.55-7.31 (m, 5 arom. H), 6.91 (d, 1 arom. H, J=8.2 Hz), 6.68 (d, 1 arom. H, J=8.2 Hz), 4.87 (d, 1 aliph. H, O$\underline{CH_2}$C$_6$H$_5$, J=11.6,Hz), 4.66 (d, 1 aliph. H, O$\underline{CH_2}$C$_6$H$_5$, J=$\overline{11.6}$ Hz), 3.76 (s, C$_3$—OCH$_3$), 2.88 (d, 3H, $^+$N—CH$_3$). MS (CI): m/z 408 (M$^+$+1).

EXAMPLE 28

Synthesis of 14β-benzyloxy-3,4-dimethoxy-17-methylmorphinan-6-one hydrochloride (compound 28.HCl)

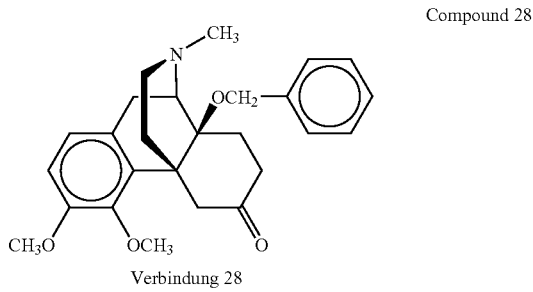

Verbindung 28

A mixture of 27.HCl (343 mg, 0.84 mmol), $K_2CO_3$ (353 mg, 2.52 mmol) and phenyltrimethyl ammonium chloride (285 mg, 1.68 mmol) and N,N-dimethylformamide (25 ml) was stirred for 4 h at 80° C. (bath temperature) under $N_2$. After filtration from the inorganic material, the filtrate was evaporated down, the evaporation residue (red-brown oil) dissolved in $CH_2Cl_2$ (50 ml), washed with water (2×20 ml) and NaCl solution (1×20 ml), dried over $Na_2SO_4$ and evaporated down. The evaporation residue (470 mg of brown oil) was purified using column chromatography (silica gel; $CH_2Cl_2$/MeOH/conc. $NH_4OH$: each 1 l: (250/2/0.5), (250/3/0.5), (250/4/0.5), (250/6/0.5), (250/8/0.5)). The evaporation residue (280 mg, yellow oil) was dissolved in ether and precipitated as compound 28.HCl using etherial HCl. Yield: 251 mg (66%); Fp. 140-145° C.; IR (KBr): 1710 (C=O) cm$^{-1}$; $^1$H-NMR (DMSO-d$_6$): δ 9.27 (s, wide, $^+$NH), 7.53-7.30 (m, 5 arom. H), 7.02 (d, 1 arom. H, J=8.4 Hz), 6.91 (d, 1 arom. H, J=8.4 Hz), 4.84 (d, 1 aliph. H, OCH$_2$C$_6$H$_5$) J=11 Hz), 4.64 (d, 1 aliph. H, OCH$_2$C$_6$H$_5$), J=11 Hz), 3.78 and 3.82 (2 s, 2 OCH$_3$), 2.87 (s, $^+$N—CH$_3$); MS (CI): m/z 422 (M$^+$+1).

EXAMPLE 29

Synthesis of 4-hydroxy-3-methoxy-17-methyl-14β-[(2-naphthylmethyl)oxy]morphinan-6-one hydrochloride (compound 29.HCl)

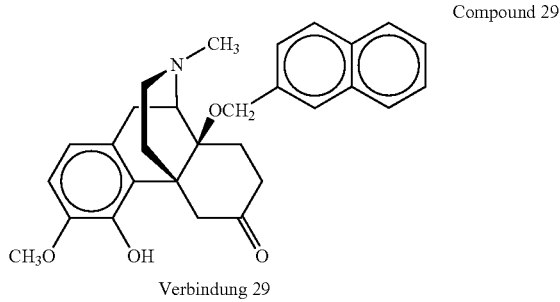

Verbindung 29

A mixture of 4,5α-expoxy-14β-hydroxy-3-methoxy-17-methylmorphinan-6-spiro-2'-(1,3-dioxolane) (Lester et al., 1965, 21, p. 771) (1.96 g, 5.45 mmol), NaH (682 mg, 28.43 mmol, obtained from 1.14 g of 60% dispersion by washing with petroleum ether) and 40 ml of water-free N,N-dimethylformamide was stirred for 45 min. at 0° C. (bath temperature) under N$_2$. After the addition of 2-bromomethylnaphthalin (96%, 2.31 g, 10.9 mmol) stirring continued for 2 h at 0° C. (bath temperature). Then small ice pieces were added until no more H$_2$ was given off, the mixture was diluted with water (50 ml) and extracted with CH$_2$Cl$_2$ (3×50 ml, 2×25 ml). The combined organic phases were washed with water (4×50 ml) and NaCl solution (1×250 ml), dried over Na$_2$SO$_4$ and evaporated down. The crystalline evaporation residue (1.26 g) was treated twice each time with 10 ml of reflux boiling MeOH for purification. Yield: 960 mg (35%) of 4,5-expoxy-3-methoxy-17-methyl-140-[(2-naphthylmethyl)oxy]morphinan-6-spiro-2'-(1,3-dioxolane). Fp. 184-185° C.; $^1$H-NMR (DMSO-d$_6$): δ 7.93-7.89 (m, 4 arom. H), 7.62-7.48 (m, 3 arom. H), 6.75 (d, 1 arom. H, J=8.2 Hz), 6.62 (d, 1 arom. H, J=8.2 Hz), 4.72 (d, 1 aliph. H, OCH$_2$naphthyl, J=11.4 Hz), 4.47 (d, 1 aliph. H, OCH$_2$naphthyl, J=11.4 Hz), 4.43 (s, C$_5$—H), 4.06-3.68 (m, 4H, OCH2CH2O), 3.78 (s, OCH$_3$), 2.34 (s, N—CH$_3$); MS (CI): m/z 500 (M$^+$+1).

A solution of 4,5α-expoxy-3-methoxy-17-methyl-14β-[(2-naphthylmethyl)oxy]-morphinan-6-spiro-2'-(1,3-dioxolane) (2.3 g, 4.60 mmol) in MeOH (30 ml) and 2N HCl (45 ml) was reflux heated for 4 h. After cooling, it was diluted with water (40 ml), alkalised with conc. NH$_4$OH and extracted with CH$_2$Cl$_2$ (1×200 ml, 1×100, 3×50 ml). The combined organic phases were washed with water (1×200 ml) and NaCl solution (1×200 ml), dried over Na$_2$SO$_4$ and evaporated down. The evaporation residue (1.84 g of dark yellow oil) was crystallised out of MeOH. Yield: 1.63 g (78%) 4,5α-expoxy-3-methoxy-17-methyl-14β-[(2-naphthylmethyl) oxy]-morphinan-6-one. Fp. 195-199° C.; IR (KBr): 1724 (vC=O) cm$^{-1}$; $^1$H-NMR (DMSO-d$_6$): δ 8.00-7.90 (m, 4 arom. H), 7.68-7.48 (m, 3 arom. H), 6.77 (d, 1 arom. H, J=8.2 Hz), 6.70 (d, 1 arom. H, J=8.2 Hz), 4.88 (s, C$_5$—H), 4.84 (d, aliph. H, 14OCH$_2$-naphthyl, J=11.2 Hz), 4.64 (d, 1 aliph. H, 14OCH$_2$-naphthyl, J=11.2 Hz), 3.80 (s, 3OCH$_3$), 2.37 (s, N—CH$_3$); MS (CI): m/z 456 (M$^+$+1).

Zinc powder was added in portions (totalling 1.75 g, 26.76 mmol) to a reflux boiling mixture of 4,5α-expoxy-3-methoxy-17-methyl-14β-[(2-naphthylmethyl)oxy]-morphinan-6-one (1.0 g, 2.20 mmol), NH$_4$Cl (1.75 g, 32.71 mmol) and MeOH (42 ml) under stirring. The mixture was reflux heated for 3 h. After filtration from the inorganic residue and washing with MeOH, the filtrate was evaporated down, water (40 ml) added to the evaporation residue, alkalised with conc. NH$_4$OH and extracted with CH$_2$Cl$_2$ (1×70 ml, 2×50 ml). The combined organic phases were washed with water (1×40 ml), 1×30 ml) and NaCl solution (1×30 ml), dried over Na$_2$SO$_4$ and evaporated down. The evaporation residue (1.09 g of light brown foamy resin) was purified using column chromatography (silica gel; CH$_2$Cl$_2$/MeOH/conc. NH$_4$OH: 1.5 l: (250/2/0.5); 0.5 l each of: (250/3/0.5), (250/14/0.5), (250/6/0.5). The evaporation residue (836 mg of beige foamy resin) was dissolved in ether and compound 29 was precipitated out as the hydrochloride (29.HCl) with etherial HCl. Yield: 729 mg (68%); Fp. 195-197° C.; IR (KBr): 1710 (C=O) cm$^{-1}$; $^1$H-NMR (DMSO-d$_6$): δ 9.24 (s, wide, $^+$NH), 8.86 (s, 4-OH), 8.02-7.91 (m, 4 arom. H, naphthyl), 7.70-7.48 (m, 3 arom. H, naphthyl), 6.91 (d, 1 arom. H, J=8.2 Hz), 6.69 (d, 1 arom. H, J=8.2 Hz), 5.01 (d, 1 aliph. H, 14OCH$_2$-naphthyl, J=12 Hz), 4.82 (d, 1 aliph. H, 14OCH$_2$-naphthyl, J=12 Hz), 3.77 (s, 3OCH$_3$), 2.90 (ps-d, $^+$NCH$_3$); MS (CI): m/z 458 (M$^+$+1).

EXAMPLE 30

Synthesis of 3,4-dimethoxy-17-methyl-14β-[(2-naphthylmethyl)oxy]morphinan-6-one hydrochloride (compound 30.HCl)

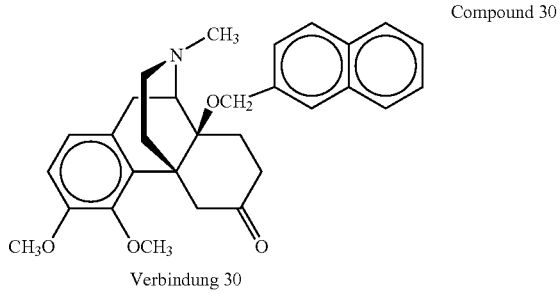

Verbindung 30

A mixture of 29.HCl (316 mg, 0.64 mmol), K$_2$CO$_3$ (304 mg, 2.17 mmol), phenyltrimethyl ammonium chloride (280 mg, 1.53 mmol) and N,N-dimethylformamide (25 ml) was stirred at 80° C. (bath temperature) under N$_2$ for 2 h. After filtration from the inorganic material, the filtrate was evaporated down, the evaporation residue (red-brown oil) absorbed in CH$_2$Cl$_2$ (50 ml), washed with water (2×20 ml) and NaCl solution (1×20 ml), dried over Na$_2$SO$_4$ and evaporated down. The evaporation residue (237 mg of brown oil) was purified using column chromatography (silica gel; CH$_2$Cl$_2$/MeOH/ conc. NH$_4$OH: 1.5 l: (250/2/0.5); 0.5 l each of: (250/3/0.5), (250/4/0.5), (250/6/0.5), (250/8/0.5). The evaporation residue (265 mg of beige foamy resin) was dissolved in ether and compound 30 was precipitated out as the hydrochloride (30.HCl) with etherial HCl. Yield: 257 mg (80%): Fp. 165-170° C.; IR (KBr): 1712 (C=O) cm$^{-1}$; $^1$H-NMR (DMSO-d$_6$): δ 9.27 (s, wide, $^+$NH), 8.03-7.91 (m, 4 arom. H), 7.70-7.51 (m, 3 arom. H), 7.05 (d, 1 arom. H, J=8.6 Hz), 6.97 (d, 1 arom. H, J=8.6 Hz), 5.01 (d, 1 aliph. H, 14OCH$_2$-naphthyl, J=11.6 Hz), 4.83 (d, 1 aliph. H, 14OCH$_2$-naphthyl, J=11.6 Hz), 3.84 and 3,79 (s, 2 OCH$_3$), 2.90 (d, $^+$NCH$_3$); MS (CI): m/z 472 (M$^+$+1).

EXAMPLE 31

Synthesis of 4-hydroxy-3-methoxy-5β,17-dimethyl-14β-[(3-phenylpropyl)oxy]morphinan-6-one hydrochloride (compound 31.HCl)

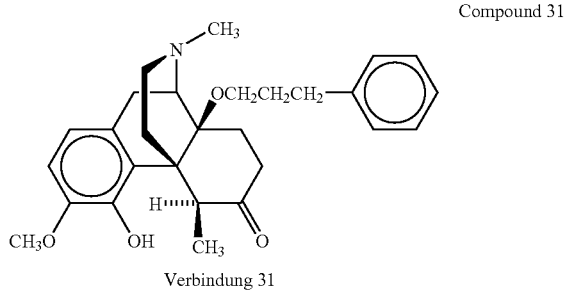

Verbindung 31

Zinc powder was added in portions (totalling 5.5 g, 84.12 mmol) to a reflux boiling mixture of 4,5α-expoxy-3-methoxy-5β,17-dimethyl-14β-[(3-phenylpropyl)oxy]morphinan-6-one (see Example 17) (3.7 g, 8.27 mmol), NH$_4$Cl (4.5 g, 83.87 mmol) and EtOH (50 ml) under stirring. The mixture was reflux heated for 47 h. After filtration from the inorganic residue and washing with EtOH, the filtrate was evaporated down, water (200 ml) added to the evaporation residue (6.35 g of white foamy resin), alkalised with conc. NH$_4$OH and extracted with CH$_2$Cl$_2$ (1×100 ml, 4×50 ml). The combined organic phases were washed with water (4×200 ml) and NaCl solution (1×200 ml), dried over Na$_2$SO$_4$ and evaporated down. The evaporation residue (3.93 g of yellow oil) was purified using column chromatography (silica gel; CH$_2$Cl$_2$/MeOH/conc. NH$_4$OH (250/2/0.5). 2.99 g (80%) of the pure compound 31 was obtained as a yellow oil. 500 mg of it was dissolved in ether and the compound 31 was precipitated out as the hydrochloride (31.HCl) with etherial HCl. Fp. >210° C. (decomp.); IR (KBr): 1700 (C=O) cm$^{-1}$; $^1$H-NMR (DMSO-d$_6$): δ 9.64 (s, C4-OH), 8.88 (s, wide, $^+$NH), 7.33-7.17 (m, 5 arom. H), 6.91 (d, 1 arom. H, J=8.2 Hz), 6.70 (d, 1 arom. H, J=8.2 Hz); 3.78 (s, 3OCH$_3$), 2.80 (d, $^+$NCH$_3$, J=3.4 Hz), 1.28 (d, C$_5$—CH$_3$, J=6.6 Hz); MS (CI): m/z 450 (M$^+$+1).

EXAMPLE 32

Synthesis of 3,4-dimethoxy-5β,17-dimethyl-14β-[(3-phenylpropyl)oxy]morphinan-6-one hydrochloride (compound 32.HCl)

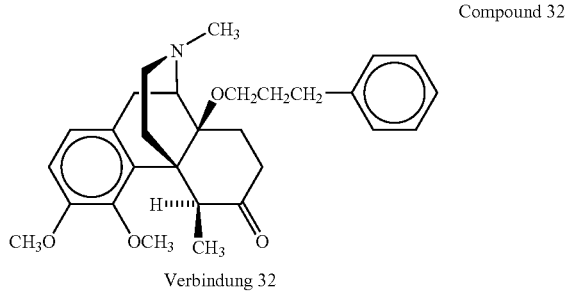

Verbindung 32

Compound 31 (base) (1.55 g, 3.44 mmol) was dissolved in 20 g of 40% tetrabutyl ammonium hydroxide solution at room temperature under N$_2$. Then a solution of dimethyl sulphate (0.48 g, 3.8 mmol) in 15 ml of dichloromethane was added. The mixture was vigorously stirred for 12.5 h at room temperature under N$_2$ and then 300 ml water and 50 ml dichloromethane were added. The aqueous phase was extracted with dichloromethane (2×50 ml). The combined organic phases were washed with conc. ammonia (1×50 ml), water (6×200 ml) and saturated sodium chloride solution (1×200 ml), dried over sodium sulphate and evaporated down. The evaporation residue (1.25 g of yellow oil) was purified using column chromatography (silica gel; CH$_2$Cl$_2$/MeOH/conc. NH$_4$OH (250/2/0.5). 1.0 g (53%) of the pure compound 32 was obtained as a yellow oil. 810 mg of it was dissolved in ether and the compound 32 was precipitated out as the hydrochloride (32.HCl) with etherial HCl. Fp. 135-138° C.; IR (KBr): 1700 (C=O) cm$^{-1}$; $^1$H-NMR (DMSO-d$_6$): δ 9.36 (s, wide, $^+$NH), 7.31-7.21 (m, 5 arom. H), 7.05 (d, 1 arom. H, J=8.4 Hz), 6.95 (d, 1 arom. H, J=8.4 Hz), 3.80 and 3.79 (2 s, 2 OCH$_3$), 2.81 (d, $^+$NCH$_3$, J=4.8 Hz), 1.25 (d, C$_5$—CH$_3$, J=7 Hz); MS (CI): m/z 464 (M$^+$+1).

EXAMPLE 33

Synthesis of 14β-ethoxy-4-hydroxy-3-methoxy-5β,17-dimethylmorphinan-6-one (compound 33)

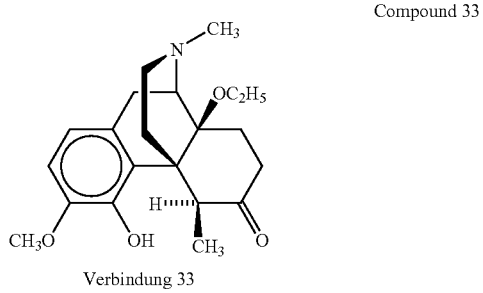

Verbindung 33

Zinc powder was added in portions (totalling 15.0 g, 229.4 mmol) to a reflux boiling mixture of 4,5α-expoxy-14β-ethoxy-3-methoxy-5β,17-dimethylmorphinan-6-one (Schmidhammer et al., Helv. Chim. Acta 1990, 73, pp. 1784-1787) (3.0 g, 8.4 mmol), NH$_4$Cl (15.0 g, 280.1 mmol) and MeOH (30 ml) under stirring. The mixture was reflux heated for 24 h. After filtration from the inorganic residue and washing with MeOH, the filtrate was evaporated down, the evaporation residue alkalised with diluted NH$_4$OH and extracted with a mixture of CH$_2$Cl$_2$ and MeOH (2:1) (1×100 ml, 3×30 ml). The combined organic phases were dried over Na$_2$SO$_4$ and evaporated down. The evaporation residue (2.82 g of brown foamy resin) was crystallised out of MeOH and in this way 684 mg of pure compound 33 was obtained. The mother liquor was evaporated down and the evaporation residue (1.895 g of brown foamy resin) was used for the production of the compound 34 without further purification. Compound 33: Fp. 122-129° C.; IR (KBr): 3480 (OH), 0.1715 (C=b) cm$^{-1}$; $^1$H-NMR (CDCl$_3$): δ 6.67 (d, 1 arom. H, J=8.0 Hz), 6.57 (d, 1 arom. H, J=8.0 Hz), 3.82 (s, OCH$_3$), 2.32 (s, NCH$_3$), 1.54 (s, C$_5$—CH$_3$),1.18 (t, CH$_3$CH$_2$, J=5.7 Hz); MS (CI): m/z 360 (M$^+$+1).

EXAMPLE 34

Synthesis of 14β-ethoxy-3,4-dimethoxy-5β,17-dimethylmorphinan-6-one salicylate (compound 34.C$_7$H$_6$O$_3$

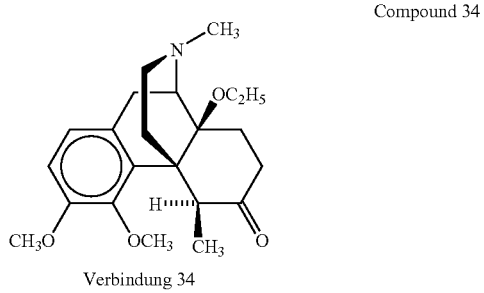

Verbindung 34

A mixture of the compound 33 (1.895 g, 5.3 mmol) (evaporation residue of the mother liquor, see above), K$_2$CO$_3$ (2.12 g, 15.3 mmol), phenyltrimethyl ammonium chloride (1.8 g, 10.5 mmol) and water free N,N-dimethylformamide (20 ml) was stirred at 80° C. (bath temperature) under $N_2$ for 3 h. After filtration from the inorganic material and washing with dichloromethane, the filtrate was evaporated down. The evaporation residue was dissolved in dichloromethane, washed with water (2×50 ml) and saturated NaCl solution (1×50 ml), dried over sodium sulphate and evaporated down. The evaporation residue (2.11 g of dark brown oil) was purified using column chromatography (basic aluminium oxide, activity level III; dichloromethane). The evaporation residue was crystallised as compound 34.$C_7H_6O_3$ with salicylic acid in diisopropylether. Yield: 1.32 g (49%). Fp. 135-141° C.; IR (KBr): 3400 ($^+$NH, OH), 1710 (C=O), 1630 ($CO_2$) cm$^{-1}$; $^1$H-NMR (CDCl$_3$): δ 7.88 (m, $^+$NH), 7.27 (m, 2 arom. H), 6.81 (m, 4,arom. H), 3.86 (s, OCH$_3$), 3.83 (s, OCH$_3$), 2.84 (s, $^+$NCH$_3$), 1.40 (d, C$_5$—CH$_3$, 5.8 Hz), 1.17 (t, C$\underline{H_3}$CH$_2$, J=5.3 Hz); MS (CI): m/z 374 (M$^+$+1).

EXAMPLE 35

Synthesis of 14β-benzyloxy-3,4-dimethoxy-5β,17-dimethylmorphinan-6-one (compound 37)

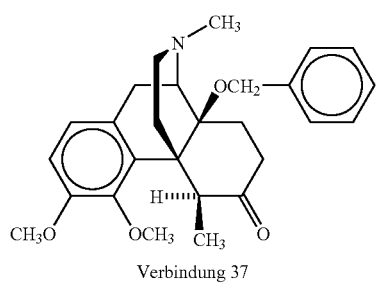

Verbindung 37

Zinc powder was added in portions (totalling 10.5 g, 160.6 mmol) to a reflux boiling mixture of 4,5α-expoxy-3-methoxy-5β,17-dimethyl-14β-hydroxymorphinan-6-one (Schmidhammer et al., Helv. Chim. Acta 1988, 71, pp. 1801-1804) (4.17 g, 12.66 mmol), NH$_4$Cl (7.0 g, 130.87 mmol) and EtOH (50 ml) under stirring. The mixture was reflux heated for 68 h. After filtration from the inorganic residue and washing with EtOH, the filtrate was evaporated down, water (150 ml) was added to the evaporation residue (7.65 g of white foamy resin), it was alkalised with conc. NH$_4$OH and extracted with CH$_2$Cl$_2$/isopropanol (3:1) (2×80 ml, 1×60 ml, 1×40 ml). The combined organic phases were washed with water (3×70 ml) and NaCl solution (1×70 ml), dried over Na$_2$SO$_4$ and evaporated down. The evaporation residue (5.02 g of brown oil) was crystallised out of CH$_2$Cl$_2$/isopropanol (5:3) to form compound 35 (4,14β-dihydroxy-3-methoxy-5β,17-dimethylmorphinan-6-one) (3.39 g, (81%). 200 mg of it was dissolved in acetone and 135 mg was precipitated with etherial HCl to give the compound 35.HCl: Fp. >185° C. (decomp.); IR (KBr): 3200 (OH), 1700 (C=O) cm$^{-1}$; Analytical data of the base compound 35: $^1$H-NMR (DMSO-d$_6$): δ 8.43 (s, C$_4$—OH), 6.77 (d, 1 arom. H, J=8.2 Hz), 6.57 (d, 1 arom. H, J=8.2 Hz), 4,49 (s, C$_{14}$—OH), 3.74 (s, C$_3$—OCH$_3$), 2.25 (s, NCH$_3$), 1.30 (d, C$_5$—CH$_3$, J=7.4 Hz); MS (CI): m/z 332 (M$^+$+1).

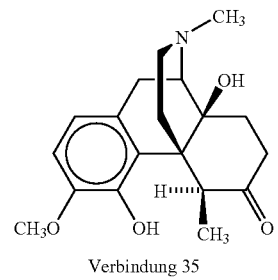

Verbindung 35

Compound 35 (base) (9.5 g, 28.67 mmol) was dissolved in 45 g of 40% tetrabutyl ammonium hydroxide solution at room temperature under $N_2$. Then a solution of dimethyl sulphate (2.75 ml (=3.67 g), 29.06 mmol) in 50 ml of dichloromethane was added. The mixture was vigorously stirred at room temperature for 5 h under $N_2$ and then 100 ml of water was added. The aqueous phase was extracted with dichloromethane (3×50 ml). The combined organic phases were washed with 2 M ammonia solution (1×70 ml), water (12×100 ml) and saturated sodium chloride solution (1×100) ml), dried over sodium sulphate and evaporated down. The evaporation residue (8.16 g of light coloured oil) was crystallised out of 4 ml MeOH. Yield: 5.06 g (51%) 14β-hydroxy-3,4-dimethoxy-5β-17-dimethylmorphinan-6-one (compound 36). Fp. 122-124° C.; IR (KBr): 1704 (C=O) cm$^{-1}$; $^1$H-NMR (COCl$_3$): δ 6.78 (s, 2 arom. H), 4.31 (s, C14-OH), 3.87 and 3.82 (2 s, 2 OCH$_3$), 2.32 (s, NCH$_3$); 1.28 (d, C$_5$—CH$_3$, J=6.8 Hz); MS (CI): m/z 346 (M$^+$+1).

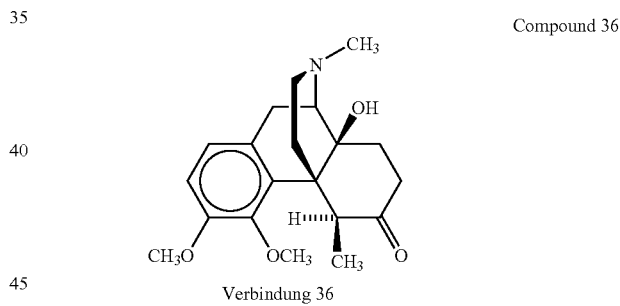

Verbindung 36

A mixture of compound 36 (7.42 g, 21.48 mmol), 2.20 ml methane sulphonic acid (3.26 g, 33.93 mmol) and 100 ml diethylene glycol was stirred for 1 h under $N_2$ and at a bath temperature of 80° C. Then the mixture was poured onto 600 ml of ice-water, alkalised with concentrated ammonia and extracted with dichloromethane (1×200 ml, 4×50 ml). The combined organic phases were washed with water (5×200 ml) and saturated sodium chloride solution (1×200 ml), dried over sodium sulphate and evaporated down. The evaporation residue (8.13 g of reddish crystals) was recrystallised out of 8 ml methanol. Yield: 4.91 g (59%) of 14β-hydroxy-3,4-dimethoxy-5β,17-dimethylmorphinan-6-spiro-2'-(1,3-dioxolane). Fp. 155-157° C.; $^1$H-NMR (CDCl$_3$): δ 6.76 (s, 2 arom. H), 4.36 (s, C14-OH), 3.91-3.57 (m, 4H, OCH$_2$CH$_2$O—C), 3.83 and 3.74 (2 s, 2CH$_3$O), 2.30 (s, CH$_3$N), 1.35 (d, C5-CH$_3$, J=5.2 Hz); MS (CI): m/z 390 (M$^+$+1).

NaH (0.13 g, 5.41 mmol) (obtained from 0.21 g of a 60% NaH dispersion in oil by washing with petroleum ether) was added to a solution of 14β-hydroxy-3,4-dimethoxy-5β,17-dimethylmorphinan-6-spiro-2'-(1,3-dioxolane) (1.00 g, 2.57 mmol) in 100 ml water-free N,N-dimethylformamide under $N_2$ at 0° C. (bath temperature) under stirring. After 15 min. benzyl bromide (0.88 g, 5.14 mmol) was added and the mixture stirred for 3 h at room temperature. Then the excess sodium hydride was broken down with pieces of ice, the reaction mixture was poured onto 300 ml water and extracted with dichloromethane/isopropanol (5:2) (3×70 ml). The combined organic phases were, washed with $H_2O$ (5×200 ml) and a saturated sodium chloride solution (1×200 ml), dried over sodium sulphate and evaporated down. The evaporation residue (1.65 g of yellowish crystals) was crystallised but of 2 ml ethanol. Yield: 0.65 g (53%) 14β-benzyloxy-3,4-dimethoxy-5β,17-dimethylmorphinan-6-spiro-2'-(1,3-dioxolane). Fp. 201-202° C.; $^1$H-NMR ($CDCl_3$): δ 7.49-7.23 (m, 5 arom. H), 6.77 (s, 2 arom. H), 4.61 (d, 1H, $PhCH_2O$, J=10.5 Hz), 4.29 (d, 1H, $PhCH_2O$, J=10.5 Hz), 3.88-3.56 (m, 4H, $OCH_2CH_2O$), 3.83 and 3.76 (2 s, $2CH_3O$), 2.30 (s, $CH_3N$), 1.25 (d, $C5-CH_3$, J=7.4 Hz); MS (CI): m/z 480 ($M^+$+1).

A solution of 14β-benzyloxy-3,4-dimethoxy-5β,17-dirmethylmorphinan-6-spiro-2'-(1,3-dioxolane) (0.50 g, 1.04 mmol) in 10 ml of a mixture of 5 ml methanol, 4 ml water and 1 ml conc. HCl was reflux heated for 30 minutes. Then the mixture was poured onto 150 ml of ice-water, alkalised with concentrated ammonia and extracted with dichloromethane/isopropanol (4:1) (2×50 ml, 2×25 ml). The combined organic phases were washed with water (2×100 ml) and a saturated sodium chloride solution (1×100 ml), dried over sodium sulphate and evaporated down. The evaporation residue (0.51 g of light coloured oil) was crystallised out of 1 ml methanol. Yield: 0.34.g (76%) of compound 37. Fp. 166-167° C.; IR (KBr): 1695 (CO) $cm^{-1}$; $^1$H-NMR ($CDCl_3$): δ 7.34-7.21, (m, 5 arom. H), 6.83 (d, 1 arom. H, J=8.6 Hz), 6,78 (d, 1 arom. H, J=8.6 Hz), 4.63 (d, 1H, $PhCH_2O$, J=10.8 Hz), 4.32 (d, 1H, $PhCH_2O$, J=10.8 Hz), 3.86 and 3.83 (2 s, $2CH_3O$), 2.30 (s, $CH_3N$), 1.43 (d, $C5-CH_3$, J=7.0 Hz); MS (CI): m/z 436 ($M^+$+1).

EXAMPLE 36

Synthesis of 4,5α-epoxy-3-hydroxy-17,17-dimethyl-6-oxo-14β-[(3-phenylpropyl)oxy]morphinanium-iodide (compound 38)

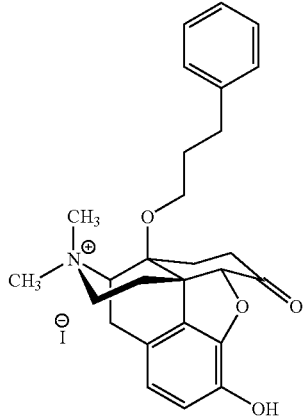

Compound 38

A solution of 4,5α-epoxy-3-methoxy-17-methyl-14-[(3-phenylpropyl)oxy]morphinan-6-one (=14-O-(3-phenylpropyl)oxycodon; see Example 1) (3.0 g, 6.90 mmol) in 48% HBr (30 ml) was reflux heated for 15 minutes. After the reaction had finished, the solution was cooled with ice, alkalised with conc. $NH_4OH$ and extracted with $CH_2Cl_2$ (5×50 ml). The combined organic phases were washed with water (3×50 ml) and a saturated NaCl solution (1×50 ml), dried over $Na_2SO_4$ and evaporated down. The evaporation residue (3.5 g of brown oil) was purified using column chromatography (silica gel; $CH_2Cl_2$/MeOH/conc. $NH_4OH$: 6 1: (250/2/0.5): each 0.5 l: (250/3/0.5), (250/4/0.5), (250/6/0.5), (250/8/0.5)). The evaporation residue (4,5α-epoxy-3-hydroxy-17-methyl-14β-[(3-phenylpropyl)oxy]morphinan-6-one, 1.36 g of yellow oil, 47%) could not be crystallised. Therefore one part was passed as oil to the next reaction and the remainder converted as usual to the hydrochloride (4,50-epoxy-3-hydroxy-17-methyl-14β-[(3-phenylpropyl)oxy]morphinan-6-one hydrochloride). Analytical data of the hydrochloride: Fp. 185-189° C.; $^1$H-NMR (DMSO-$d_6$): δ 9.50 (s, $C_3$—OH), 8.68 (s, wide, $^+$NH), 7.34-7.16 (m, 5 arom. H), 6.70 (d, 1 arom. H, J=8.0 Hz), 6.65 (d, 1 arom. H, J=8.0 Hz), 4.87 (s, C5-H), 2.92 (d, $^+NCH_3$).

A solution of 4,5α-epoxy-3-hydroxy-17-methyl-14β-[(3-phenylpropyl)oxy]morphinan-6-one (oil, 257 mg, 0.61 mmol) and methyl iodide (0.38 ml, 6.11 mmol) in acetonitrile (10 ml) was stirred for 2 days at 50° C. (bath temperature) under $N_2$. A DC examination showed that the reaction was not concluded. Therefore further methyl iodide (0.38 ml, 6.11 mmol) was added and the solution stirred further for 3 days under the same conditions. Then the solvent was evaporated off and the evaporation residue (367 mg of yellow foamy resin) was purified using column chromatography (silica gel; $CH_2Cl_2$/MeOH (10:1)). Evaporation residue 240 mg (71%) amorphous compound 38. Fp. 164-170° C.; IR (KBr): 1723 (C=O) $cm^{-1}$; $^1$H-NMR (DMSO-$d_6$): δ 9.57 (s, C3-OH), 7.3-7.16 (m, 5 arom. H), 6.67 (s, 2 arom. H, $C_1$—H, $C_2$—H), 4.88 (s, $C_5$—H), 3.56 (s, $N^+CH_3$, axial), 3.21 (s, $^+NCH_3$, equatorial); MS (CI): m/z 434 ($M^+$).

EXAMPLE 37

Synthesis of (17S)-4,5α-epoxy-17-ethyl-3-hydroxy-17-methyl-6-oxo-14β-[(3-phenylpropyl)oxy]morphinanium-iodide (compound 39)

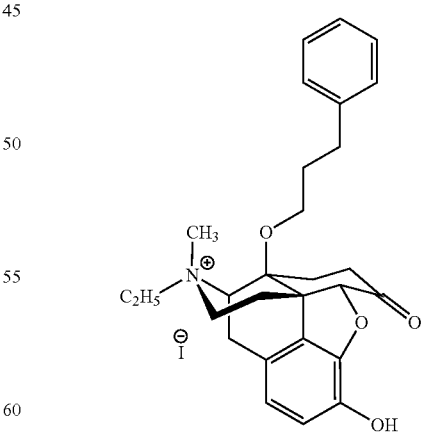

Compound 39

A solution of compound 20 (see Example 20) (250 mg, 0.58 mmol) and methyl iodide (0.36 ml, 5.80 mmol) in acetonitrile (10 ml) was stirred for 6 days at 50° C. (bath temperature) under $N_2$. The solution was evaporated down and the evaporation residue (320 mg of bright beige foamy resin) was purified using column chromatography (silica gel; CH₂Cl₂/MeOH: each 1 l: (95/5), (92.5/7.5)). Evaporation residue (240 mg, 72%) of amorphous compound 39. Fp. 171-176° C.; IR (KBr): 1723 (C=O) cm⁻¹; ¹H-NMR (DMSO-d₆): δ 9.55 (s, C3-OH), 7.31-7.16 (m, 5 arom. H), 6.68 (s, 2 arom. H, C₁—H, C₂—H), 4.87 (s, C₅—H), 3.44 (3H, N⁺CH₃, axial), 1.34 (t, 3H, ⁺NCH₂CH₃, J=7 Hz); MS (CI): m/z 448 (M⁺).

EXAMPLE 38

Synthesis of (17R)-4,5α-epoxy-3-hydroxy-17-methyl-6-oxo-14β-[(3-phenylpropyl)oxy]-17-[(2-R,S-tetrahydrofuran-2-yl)methyl]morphinanium-iodide (compound 40)

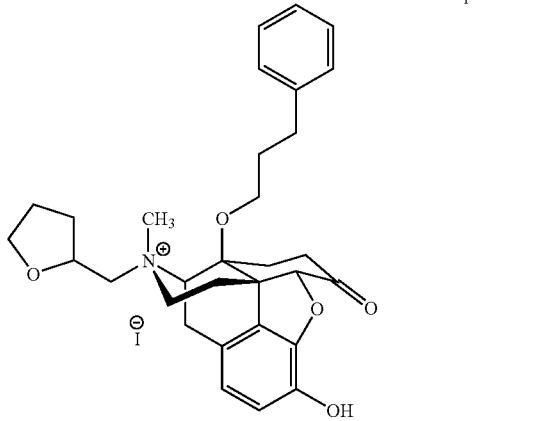

Compound 40

A solution of the compound 10 (see Example 10) (190 mg, 0.39 mmol) and methyl iodide (0.24 ml, 3.9 mmol) in acetonitrile (8 ml) was stirred for 10 days at 40-50° C. (bath temperature) under N₂. The solution was evaporated down and the evaporation residue (248 mg of beige foamy resin) was purified using column chromatography (silica gel; CH₂Cl₂/MeOH: 2 l: (250/5); 1 l: (250/7.5)). The resulting evaporation residue (70 mg of yellow foamy resin, 28%) was pure compound 40. Fp. 156-159° C.; IR (KBr): 1724 (C=O) cm⁻¹; ¹H-NMR (DMSO-d₆): δ 9.53 (s, C3-OH), 7.30-7.16 (m, 5 arom. H), 6.68 (s, 2 arom. H, C₁—H, C₂—H), 4.85 (s, 1H, C₅—H), 3.58 (s, ⁺NCH₃, axial); MS (CI): m/z 504 (M⁺).

EXAMPLE 39

Synthesis of (17R)-17-allyl-4,5α-epoxy-14β-ethoxy-3-hydroxy-17-methyl-6-oxomorphinanium-iodide (compound 41)

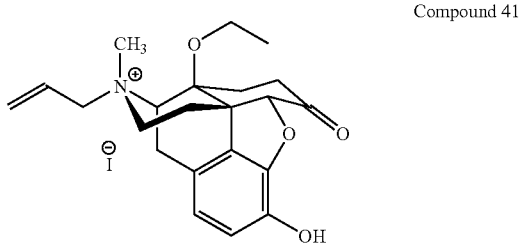

Compound 41

A solution of 14-O-ethylnaloxone (Kobylecki et al., J. Med. Chem. 1982, 25, p. 116) (300 mg, 0.84 mmol) and methyl iodide (0.25 ml, 4.2 mmol) in 8 ml acetonitrile for 7 days at 30° C. (bath temperature) and then evaporated down. The evaporation residue (450 mg of light brown oil) was purified using column chromatography (silica gel; CH₂Cl₂/MeOH (250:4)). Evaporation residue (110 mg, 35%) of amorphous compound 41. Fp. 130-134° C.; IR (KBr): 1724 (CO) cm⁻¹; ¹H-NMR (DMSO-d₆): δ 9.54 (s, C3-OH), 6.70 (s, 2 arom. H), 6.32-6.07 (m, 1 olef. H), 5.84-5.63 (m, 2 olef. H), 4.92 (s, C5-H), 3.49 (s, ⁺NCH₃, axial), 1.24 (t, 3H, OCHCH₃, J=6.8 Hz); MS (CI): m/z 370 (M⁺).

EXAMPLE 40

Synthesis of (17R)-17-allyl-4,5α-epoxy-3-hydroxy-14β-methoxy-17-methyl-6-oxomorphinanium-iodide (compound 42)

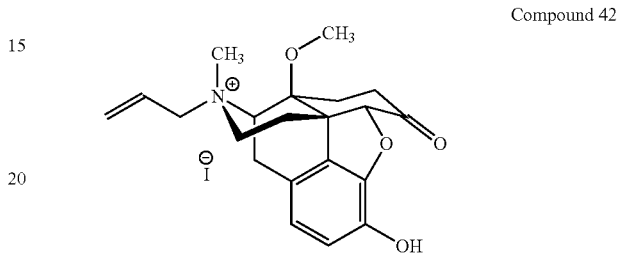

Compound 42

A solution of 14-O-methylnaloxone (Kobylecki et al., J. Med. Chem. 1982, 25, p. 116) (230 mg, 0.67 mmol) and methyl iodide (0.21 ml, 3.37 mmol) was stirred in 10 ml acetonitrile for 7 days at 40° C. (bath temperature) and then evaporated down. The evaporation residue (341 mg of light brown oil) was purified using column chromatography (silica gel; CH₂Cl₂/MeOH (250:4.5->250:9)). Evaporation residue (202 mg, 62%) of amorphous compound 42. Fp. 178-181° C.; IR (KBr): 1722 (CO) cm⁻¹; ¹H-NMR (DMSO-d₆): δ 9.55 (s, C3-OH), 6.70 (s, 2 arom. H), 6.28-6.06 (m, 1 olef. H), 5.82-5.64 (m, 2 olef. H), 4.94 (s, C5-H), 3.45 (s, ⁺NCH₃, axial), 3.38 (s, CH₃O); MS (CI): m/z 356 (M⁺).

EXAMPLE 41

Synthesis of (17S)-17-allyl-4,5α-epoxy-3-hydroxy-14β-methoxy-17-methyl-6-oxomorphinanium-iodide (compound 43)

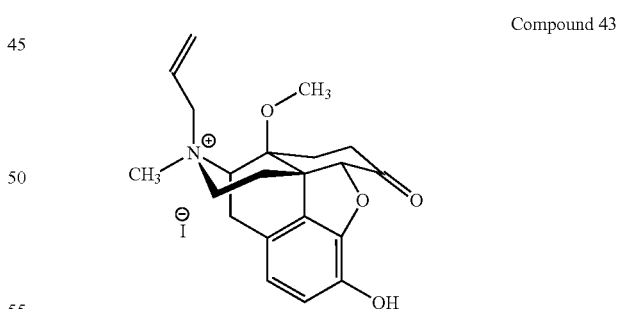

Compound 43

A solution of 14-O-methyloxymorphone (Schmidhammer et al., J. Med. Chem. 1984, 27, pp. 1575-1579) (210 mg, 0.67 mmol) and allyl iodide (0.28 ml, 3.35 mmol) was stirred in 5 ml N,N-dimethylformamide for 7 days at 40° C. (bath temperature) and then evaporated down. The evaporation residue (484 mg of brown oil) was purified using column chromatography (silica gel; CH₂Cl₂/MeOH (250:5->250:12)). The evaporation residue (134 mg) was again purified using column chromatography (silica gel; CH₂Cl₂/MeOH (250:4.5)). Evaporation residue 77 mg (27%) of amorphous compound 43. Fp. >140° C.; IR (KBr): 1724 (CO) cm⁻¹; ¹H-NMR (DMSO-d$_6$): δ 9.57 (s, C3-OH), 6.68 (s, 2 arom. H), 6.28-6.08 (m, 1 olef. H), 5.75-5.63 (m, 2 olef. H), 4.95 (s, C5-H), 3.42 (s, CH$_3$O), 3.05 (s, $^+$NCH$_3$, equatorial); MS (CI): m/z 356 (M$^+$).

EXAMPLE 42

Synthesis of 4,5α-epoxy-3-hydroxy-14β-methoxy-17,17-dimethyl-6-oxomorphinanium-iodide (compound 44)

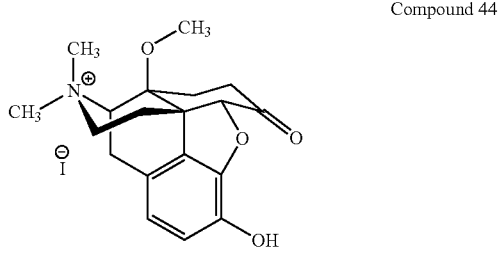

Compound 44

A solution of 14-O-methyloxymorphone (Schmidhammer et al., J. Med. Chem. 1984, 27, pp. 1575-1579) (200 mg, 0.63 mmol) and methyl iodide (0.32 ml, 5.07 mmol) in acetonitrile (10 ml) was stirred for 21 hours under N$_2$ at 50° C. (bath temperature). Then methyl iodide (0.2 ml, 3.17 mmol) was again added, stirred further for 24 h under the same conditions and evaporated down. The evaporation residue (324 mg of brown foamy resin) was crystallised out of MeOH (0.5 ml) and purified by recrystallisation out of MeOH. Yield: 244 mg (84%) of compound 44. Fp. 225-240° C.; IR (KBr): 1725 (C=O) cm$^{-1}$; $^1$H-NMR (DMSO-d$_6$): δ 9.55 (s, C$_3$—OH), 6.69 (s, 2 arom. H, C$_1$—H, C$_2$—H), 4.94 (s, C$_5$—H), 3.55 (s, $^+$NCH$_3$, axial), 3.38 (s, OCH$_3$), 3.22 (s, $^+$NCH$_3$, equatorial); MS (CI): m/z 330 (M$^+$).

EXAMPLE 43

Synthesis of 5β-benzyl-14β-(butyloxy)-4,5α-epoxy-3-hydroxy-17,17-dimethyl-6-oxomorphinanium-iodide (compound 45)

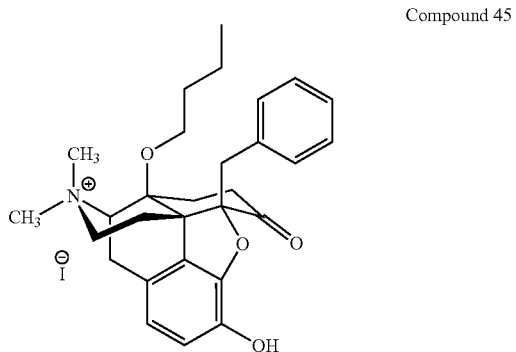

Compound 45

NaH (0.52 g, 21.6 mmol) (obtained from 0.86 g of a 60% NaH dispersion in oil by washing with petroleum ether) was added to a solution of 5β-benzyl-14-hydroxycodeinone (M. Gates et al., J, Org. Chem. 1989, 54, pp. 972-974) (2.90 g, 7.2 mmol) in 40 ml water-free N,N-dimethylformamide under N$_2$ at 0° C. (bath temperature) under stirring. After 20 min. trans-crotylbromide (1.26 g, 9.3 mmol) was added and the mixture first stirred for 40 min at 0° C. (bath temperature), then for 2 h at room temperature. Then small pieces of ice were added until no more hydrogen was given off, the reaction mixture was poured onto 100 ml water and extracted with dichloromethane (1×100 ml, 5×50 ml). The combined organic phases were washed with saturated sodium chloride solution (6×250 ml), dried over sodium sulphate and the evaporation residue (3.25 g of brown oil) purified using column chromatography (silica gel; CH$_2$Cl$_2$/MeOH/conc. NH$_4$OH 250:6:0.5). From the resulting yellowish oil (1.86 g, 56%) 0.1 g was dissolved in 5 ml ether and etherial HCl added. 0.1 g of colourless crystals of 5β-benzyl-14β-{[(E)-(but-2-enyl]oxy}-7,8α-didehydro-4,5α-epoxy-3-methoxy-17-methylmorphinan-6-one hydrochloride was isolated. Fp. 125-130° C.; MS (CI): 458 (M$^+$+1); IR (KBr): 1684 (C=O) cm$^{-1}$; $^1$H-NMR (DMSO-d$_6$, δ in ppm): 9.22 (s, wide HN$^+$), 7.28-7.13 (m, 5 arom. H; 1 olefin. H, CH-8), 6.84 (d, 1 arom. H, J=8.4 Hz), 6.74 (d, 1 arom. H, J=8.4 Hz), 6.23 (d, 1 olefin. H, CH-7, J=10.2 Hz), 5.69-5.34 (m, 2 olefin. H), 3.75 (s, CH$_3$O), 2.91 (d, CH$_3$N$^+$), 1.69-1.65 (d, 3H, C14-OCH$_2$CHCHCH$_3$, J=7.4 Hz).

A mixture of 5β-benzyl-14β-{[(E)-(but-2-enyl]oxy}-7,8-didehydro-4,5α-epoxy-3-methoxy-17-methylmorphinan-6-one (1.75 g, 3.8 mmol) and 0.24 g Pd/C (10%) in 60 ml methanol was hydrogenated for 1.5 hours at 35 psi and room temperature. The catalyst was filtered off and washed with 20 ml methanol. The filtrate was evaporated down. Yield: 1.43 g (81%) of bright yellow oil of which 0.1 g was dissolved in 5 ml ether and the hydrochloride was precipitated by the addition of etherial HCl. 0.1 g of colourless crystals of 5β-benzyl-14β-(butoxy)-4,5α-epoxy-3-methoxy-17-methylmorphinan-6-one hydrochloride was isolated. Fp. 148-152° C.; MS (CI): 462 (M$^+$+1); IR (KBr): 1729 (C=O) cm$^{-1}$; $^1$H-NMR (DMSO-d$_6$, δ in ppm): 9.00 (s, wide HN$^+$), 7.29-7.16 (m, 5 arom. H); 6.85 (d, 1 arom. H, J=8.4 Hz), 6.75 (d, 1 arom. H, J=8.4 Hz), 3.80 (s, CH$_3$O), 2.94 (d, CH$_3$N$^+$, J=4.4 Hz), 1.02 (t, 3H, C14-O(CH$_2$)$_3$CH$_3$, J=7.2 Hz).

A solution of 5β-benzyl-14β-butoxy-4,5α-epoxy-3-methoxy-17-methylmorphinan-6-one (1.30 g, 2.82 mmol) in 10 ml 48% HBr was reflux heated for 20 min. Then the solution was cooled, poured onto 100 ml of ice, alkalised with conc. NH$_4$OH and extracted with dichloromethane (5×50 ml). The combined organic phases were washed with saturated sodium chloride solution (3×150 ml), dried over sodium sulphate and evaporated down. The residue (0.97 g of grey-black foamy resin) was purified using column chromatography (silica gel; CH$_2$Cl$_2$/MeOH/conc. NH$_4$OH 250:6:0.5). Yield: 0.82 g (65%) of dark yellow oil of which 0.06 g was dissolved in 5 ml ether and the hydrochloride precipitated by the addition of etherial HCl. 0.06 g of beige crystals of 5β-benzyl-14β-butoxy-4,5α-epoxy-3-hydroxy-17-methylmorphinan-6-one hydrochloride was isolated. Fp. 200-204° C.; MS (CI): 448 (M$^+$+1); IR (KBr): 1729 (C=O) cm$^{-1}$; $^1$H-NMR (DMSO-d$_6$, δ in ppm): 9.45 (s, OH), 8.72 (s, wide HN$^+$), 7.25-7.22 (m, 5 arom. H); 6.67-6.63 (s, 2 arom. H, CH-1 and CH-2), 2.93 (d, CH$_3$N$^+$), 1.02 (t, 3H, C14-O(CH$_2$)$_3$CH$_3$, J=7.3 Hz).

A solution of 5β-benzyl-14β-butoxy-4,5α-epoxy-3-hydroxy-17-methylmorphinan-6-one (0.32 g, 0.72 mmol) and methyl iodide (0.51 g, 3.58 mmol) in 10 ml of water-free acetonitrile was stirred under N$_2$ at 40° C. (bath temperature) for 2 days and then evaporated down. The evaporation residue (0.41 g of brown oil) was purified using column chromatography (silica gel; CH$_2$Cl$_2$/MeOH 250:6). Yield: 0.22 g (54%) slightly beige crystals of the compound 45. Fp. 188-195° C.;

MS (CI): 462 (M$^+$); IR (KBr): 1729 (C=O) cm$^{-1}$; $^1$H-NMR (DMSO-d$_6$, δ in ppm): 9.49 (s, OH), 7.28-7.20 (m, 5 arom. H), 6.69 (d, 1 arom. H, J=8.2 Hz), 6.62 (d, 1 arom. H, J=8.2 Hz), 3.61 (s, CH$_3$N$^+$, axial), 3.23 (s, CH$_3$N$^+$, equatorial), 1.01 (t, 3H, C14-O(CH$_2$)$_3$C$\underline{H}_3$, J=7.0 Hz).

EXAMPLE 44

Synthesis of (17S)-17-allyl-5β-benzyl-14β-butoxy-4,5α-epoxy-3-hydroxy-17-methyl-6-oxomorphinanium-iodide (compound 46)

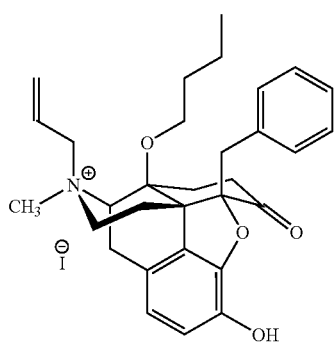

Compound 46

A solution of 5β-benzyl-14β-butoxy-4,5α-epoxy-3-hydroxy-17-methylmorphinan-6-one (see Example 45) (0.31 g, 0.69 mmol) and allyl bromide (0.94 g, 5.59 mmol) in 10 ml of water-free acetonitrile was stirred under N$_2$ at 40° C. (bath temperature) for one day and then evaporated down. The evaporation residue (0.45 g of brown oil) was purified using column chromatography (silica gel; CH$_2$Cl$_2$/MeOH 250:5). Yield: 0.11 g (26%) of beige crystals of the compound 46. Fp. 200-205° C.; MS (CI): 488.2 (M$^+$); IR (KBr): 1728 (C=O) cm$^{-1}$; $^1$H-NMR (DMSO-d$_6$, δ in ppm): 9.49 (s, OH), 7.26-7.23 (m, 5 arom. H), 6.67 (s, 2 arom. H, CH-1 and CH-2), 6.22-6.13 (m, 1 olefin. H), 5.80-5.66 (m, 2 olefin. H), 3.50 (s, CH$_3$N$^+$, equatorial), 1.02 (t, C14-O(CH$_2$)$_3$C$\underline{H}_3$, J=7.4 Hz).

EXAMPLE 45

Synthesis of 14β-butoxy-4,5α-epoxy-3-hydroxy-17,17-dimethyl-6-oxomorphinanium-iodide (compound 47)

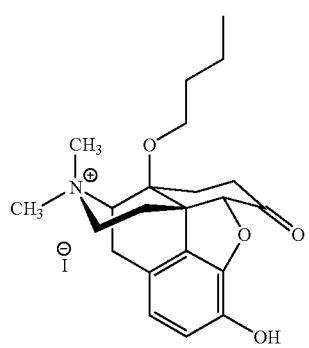

Compound 47

NaH (0.92 g, 38.3 mmol) (obtained from 1.53 g of a 60% NaH dispersion in oil by washing with petroleum ether) was added to a suspension of 14-hydroxycodeinone (Iijima et al., J. Med. Chem. 1978, 21, p. 398) (4.0 g, 12.8 mmol) in 50 ml water-free N,N-dimethylformamide under N$_2$ at 0° C. (bath temperature) under stirring. After 20 min. trans-crotylbromide (2.24 g, 16.6 mmol), dissolved in 20 ml DMF, was added drop by drop and the mixture stirred further for 40 min at 0° C. (bath temperature), then for 3 h at room temperature. Then small pieces of ice were added until no more hydrogen was given off, the mixture was poured onto 100 ml water and extracted with dichloromethane (1×100 ml, 0.5×50 ml), the combined organic phases were washed with saturated sodium chloride solution (6×250 ml) and dried over sodium sulphate. The evaporation residue (5.2 g of yellow-brown oil) was purified using column chromatography (silica gel; CH$_2$Cl$_2$/MeOH/conc: NH$_4$OH (250:5:0.5)). A yellowish oil (2.20 g) was produced which was crystallised out of methanol. Yield: 1.75 g (36%) of yellowish crystals of 14β-{[(E)-(but-2-enyl]oxy}-7,8-didehydro-4,5α-epoxy-3-methoxy-17-methylmorphinan-6-one. Fp. 113-117° C.; MS (CI): 368.2 (M$^+$+1); IR (KBr): 1679 (C=O) cm$^{-1}$; $^1$H-NMR (DMSO-d$_6$, δ in ppm): 7.13 (d, 1 olefin. H; CH-8, J=10.0 Hz), 6.73 (d, 1 arom. H, J=8.0 Hz), 6.64 (d, 1 arom. H, J=8.0 Hz), 6.14 (d, 1 olefin. H, CH-7, J=9.8 Hz), 5.69-5.43 (m, 2 olefin. H), 4.78 (s, CH-5), 4.03-3.80 (m, 2H, C14-OC$\underline{H}_2$—), 3.72 (s, CH$_3$O), 2.34 (s, CH$_3$N$^+$), 1.64 (d, OCH$_2$CHCHC$\underline{H}_3$, J=6.0 Hz).

A mixture of 14β-{[(E)-(but-2-enyl]oxy}-7,8α-didehydro-4,5α-epoxy-3-methoxy-17-methylmorphinan-6-one (0.82 g, 2.23 mmol) and 0.82 g Pd/C (10%) in 50 ml methanol was hydrogenated for 45 min. at 30 psi and at room temperature. The catalyst was filtered off, washed with 20 ml methanol and the filtrate evaporated down. Yield: 1.02 g of bright yellow oil, which was purified using column chromatography (silica gel; CH$_2$Cl$_2$/MeOH/conc. NH$_4$OH (250:2:0.5)). This gave a yellowish oil which was crystallised out of methanol. Yield: 0.52 g (63%) of colourless crystals of 14β-butoxy-4,5α-epoxy-3-methoxy-17-methylmorphinan-6-one was isolated. Fp. 112-117° C.; MS (CI): 371.1 (M$^+$+1); IR (KBr): 1722 (C=O) cm$^{-1}$; $^1$H-NMR (DMSO-d$_6$, δ in ppm): 6.74 (d, 1 arom. H, J=8.0 Hz), 6.65 (d, 1 arom. H, J=8.2 Hz), 4.75 (s, CH-5), 3.78 (s, CH$_3$O), 2.29 (s, CH$_3$N), 0.93 (t, OCH$_2$CH$_2$CH$_2$C$\underline{H}_3$, J=7.2 Hz).

A solution of 14β-butoxy-4,5α-epoxy-3-methoxy-17-methylmorphinan-6-one (0.30 g, 0.81 mmol) in 3.2 ml 48% HBr was reflux heated for 8 min. Then the solution was cooled, poured onto 20 ml of ice, alkalised with conc. NH$_4$OH and extracted with dichloromethane (5×30 ml). The combined organic phases were washed with saturated sodium chloride solution (3×100 ml), dried over sodium sulphate and evaporated down. The residue (0.29 g of brown oil) was purified using column chromatography (silica gel; CH$_2$Cl$_2$/MeOH/conc. NH$_4$OH 250:5:0.5). Yield: 0.06 g (21%) of dark yellow oil which was dissolved in 5 ml ether and converted into the hydrochloride with etherial HCl. 0.06 g of light brown crystals of 14β-butoxy-4,5α-epoxy-3-hydroxy-17-methylmorphinan-6-one hydrochloride was isolated. Fp. 168-172° C.; MS (CI): 358.2 (M$^+$+1); IR (KBr): 1725 (C=O) cm$^{-1}$; $^1$H-NMR (DMSO-d$_6$, δ in ppm): 9.51 (s, OH), 8.75 (s, wide, HN$^+$), 6.71 (d, 1 arom. H, J=8.2 Hz), 6.65 (d, 1 arom. H, J=8.0 Hz), 4.92 (s, CH-5), 2.82 (d, CH$_3$N$^+$, J=4.4 Hz), 0.95 (t, O(CH$_2$)$_3$C$\underline{H}_3$, J=7.4 Hz).

A solution of 14β-butoxy-4,5α-epoxy-3-hydroxy-17-methylmorphinan-6-one (0.53 g, 1.49 mmol) and methyl iodide (1.06 g, 7.44 mmol) in 10 ml of water-free acetonitrile was stirred under N$_2$ at 40° C. (bath temperature) for 2 days and then evaporated down. The evaporation residue (0.70 g of brown oil) was purified using column chromatography (silica gel; CH₂Cl₂/MeOH 250:4). Yield: 0.31 g (42%) of colourless crystals of the compound 47. Fp. 180-185° C.; MS (CI): 372.2 (M⁺); IR (KBr): 1726 (C=O) cm⁻¹; ¹H-NMR (DMSO-d₆, δ in ppm): 9.55 (s, OH), 6.68 (s, 2 arom. H), 4.95 (s, CH-5), 3.57 (s, CH₃N⁺, axial), 3.21 (s, CH₃N⁺, equatorial), 0.94 (t, O(CH₂)₃C$\underline{H_3}$, J=7.3 Hz).

EXAMPLE 46

Synthesis of (17R)-17-cyclopropylmethyl-4,5α-epoxy-3-hydroxy-17-methyl-6-oxo-14β-[(3-phenylpropyl)oxy]morphinanium-iodide (compound 48) and of (17R)-17-cyclopropylmethyl-4,5α-epoxy-3-methoxy-17-methyl-6-oxo-14β-[(3-phenylpropyl)oxy]morphinanium-iodide (compound 49)

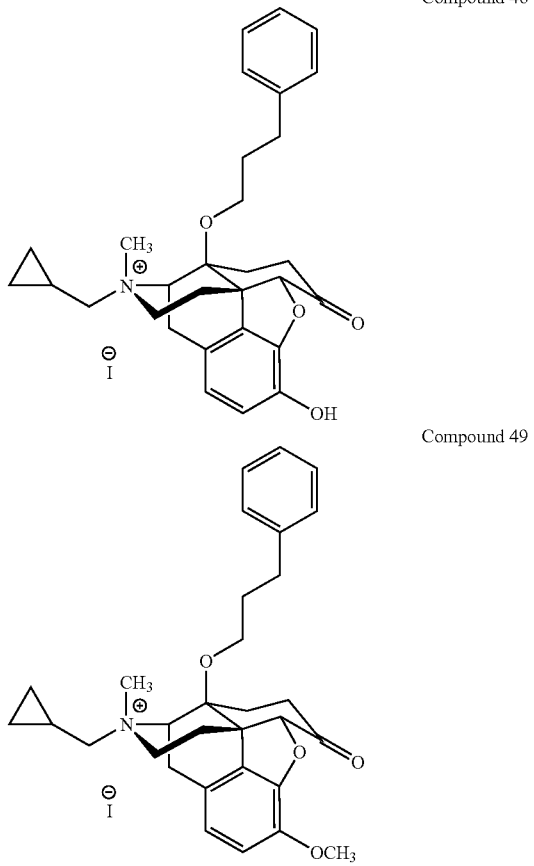

Compound 48

Compound 49

A mixture of 17-cyclopropylmethyl-4,5α-epoxymorphinan-6-spiro-2'-(1,3-dioxolane)-3,14β-diol (Schmidhammer et al., Heterocycles 1998, 49, 1, pp. 489-498) (7.92 g, 20.55 mmol), K₂CO₃ (7.67 g, 55.49 mmol), benzyl bromide (4.57 g, 26.72 mmol) and 80 ml of water-free N,N-dimethylformamide was stirred for 12 h under N₂ at room temperature. The inorganic material was filtered off, washed with dichloromethane and the filtrate evaporated down. The crystalline evaporation residue (10.97 g) was recrystallised out of methanol. Yield: 8.80 g (90%) of colourless crystals of 3-benzyloxy-17-cyclopropylmethyl-4,5α-epoxy-14β-hydroxymorphinan-6-spiro-2'-(1,3-dioxolane). Fp. 130-131° C.; MS (CI): 476 (M⁺+1); IR (KBr): 3352 (OH) cm⁻¹; ¹H-NMR (CDCl₃, δ in ppm): 7.42-7.27 (m, 5 arom. H), 6.75 (d, 1 arom. H, J=8.3 Hz), 6.54 (d, 1 arom. H, J=8.3 Hz), 5.17 (d, 1H, J=11.7 Hz, OCH₂Ph), 5.10 (d, 1H, J=11.7 Hz, OCH₂Ph), 4.58 (s, CH-5), 4.19-3.73 (m, 4H, OCH₂CH₂O). NaH (2.24 g, 93.6 mmol) (obtained from 3.75 g of a 60% NaH dispersion in oil by washing with petroleum ether) was added to a solution of 3-benzyloxy-17-cyclopropylmethyl-4,5α-epoxy-14β-hydroxymorphinan-6-spiro-2'-(1,3-dioxolane) (14.8 g, 31.2 mmol) in 100 ml water-free N,N-dimethylformamide under N₂ at 0° C. (bath temperature) under stirring. After 20 min. cinnamyl bromide (7.99 g, 40.6 mmol), dissolved in 20 ml DMF, was added drop by drop and the mixture stirred further for 25 min at 0° C. (bath temperature), then for 3.5 h at room temperature. Then small pieces of ice were added until no more hydrogen was given off. The mixture was poured onto 200 ml water and extracted with dichloromethane (4×100 ml), the combined organic phases were washed with saturated sodium chloride solution (5×250 ml), dried over sodium sulphate and evaporated down. The evaporation residue (18.2 g of yellow-brown oil) was purified using column chromatography (silica gel; CH₂Cl₂/MeOH/conc. NH₄OH 250:3:0.5). A yellowish oil (6.1 g, 33%) was produced of which 0.2 g was dissolved in 5 ml ether and converted into the hydrochloride with etherial HCl. 0.1 g of beige crystals of 3-benzyloxy-17-cyclopropylmethyl-4,5α-epoxy-14β-{[(E)-3-phenylprop-2-enyl]oxy}morphinan-6-spiro-2'-(1,3-dioxolane) hydrochloride was isolated. Fp. 133-136° C.; MS (CI): 592 (M⁺+1); ¹H-NMR (DMSO-d₆): δ 8.23 (s, wide, HN⁺), 7.63-7.24 (m, 10 arom. H), 6.93 (d, 1 arom. H, J=8.4 Hz), 6.70 (d, 1 arom. H, J=8.4 Hz), 6.70 (m, 2 olefin. H), 5.15 (s, 2H, C3-OCH₂Ph), 4.65 (s, CH-5), 4.33-4.20 (m, 2H, OCH₂CHCHPh), 4.04-3.74 (m, 4H, OCH₂CH₂).

A mixture of 3-benzyloxy-17-cyclopropylmethyl-4,5α-epoxy-14β-{[(E)-3-phenylprop-2-enyl]oxy}morphinan-6-spiro-2'-(1,3-dioxolane) (6.08 g, 10.3 mmol) and 0.60 g of Pd/C (10%) in a mixture of 100 ml methanol and 50 ml tetrahydrofuran was hydrogenated for 2.5 hours at 30 psi and at room temperature. The catalyst was filtered off, washed with 20 ml each of methanol and tetrahydrofuran and the filtrate evaporated down. Evaporation residue 4.02 g of bright yellow oil, which was purified using column chromatography (silica gel; CH₂Cl₂/MeOH/conc. NH₄OH 250:5:0.5). This gave a yellowish oil (2.75 g, 53%) of which 0.07 g was dissolved in 5 ml ether and converted into the hydrochloride with etherial HCl. 0.06 g of colourless crystals of 17-cyclopropylmethyl-4,5α-epoxy-3-hydroxy-14β-[(3-phenylpropyl)oxy]morphinan-6-spiro-2'-(1,3-dioxolane) hydrochloride was isolated. Fp. 158-162° C.; MS (CI): 504 (M⁺+1); ¹H-NMR (DMSO-d₆, δ in ppm): 9.24 (s, OH), 7.79 (s, wide, HN⁺), 7.35-7.18 (m, 5 arom. H), 6.68 (d, 1 arom. H, J=8.0 Hz), 6.57 (d, 1 arom. H, J=8.0 Hz), 4.51 (s, CH-5),14.09-3.71 (m, 4H, OCH₂CH₂O).

A solution of 17-cyclopropylmethyl-4,5α-epoxy-3-hydroxy-14β-[(3-phenylpropyl)oxy]morphinan-6-spiro-2'-(1,3-dioxolane) (0.22 g, 0.44 mmol) was reflux heated for 1 h in 5 ml of a+mixture of conc. HCl/MeOH (4:9). After cooling the resulting crystals were filtered off, the filtrate evaporated down and the residue crystallised out of ether. Yield: 0.122 g (61%) of colourless needle-shaped crystals of 17-cyclopropylmethyl-4,5α-epoxy-3-hydroxy-14β-[(3-phenylpropyl)oxy]morphinan-6-one hydrochloride. Fp. 200-230° C.; MS (CI): 460.3 (M⁺+1); IR (KBr): 1725 (C=O) cm⁻¹; ¹H-NMR (DMSO-d₆, δ in ppm): 9.52 (s, OH), 8.20 (s, wide, HN⁺), 7.30-7.18 (m, 5 arom. H), 6.71 (d, 1 arom. H, J=8.0 Hz), 6.64 (d, 1 arom. H, J=8.0 Hz), 4.89 (s, CH-5).

A solution of 17-cyclopropylmethyl-4,5α-epoxy-3-hydroxy-14β-[(3-phenylpropyl)oxy]morphinan-6-one (0.54 g, 1.17 mmol) and methyl iodide, (0.83 g, 5.84 mmol) in 10 ml of water-free acetonitrile was stirred under $N_2$ at 40° C. (bath temperature) for 5 days and then evaporated down. The residue (0.72 g of brown oil) was purified using column chromatography (silica gel; $CH_2Cl_2$/MeOH 250:4). Two different products were isolated:

Compound 48: Yield: 0.21 g (30%) of colourless crystals. Fp. 175-176° C.; MS (CI): 474 ($M^+$); IR (KBr): 1726 (C=O) $cm^{-1}$; $^1$H-NMR (DMSO-$d_6$, δ in ppm): 9.53 (s, wide, OH), 7.31-7.17 (m, 5 arom. H), 6.69 (s, 2 arom. H), 4.87 (s, CH-5), 3.53 (s, $CH_3N^+$, axial).

Compound 49: Yield: 0.03 g (4%) of bright orange crystals. Fp. 133-136° C.; MS (CI): 488 ($M^+$); IR (KBr): 1725 (C=O) $cm^{-1}$; $^1$H-NMR (DMSO-$d_6$, δ in ppm): 7.31-7.19 (m, 5 arom. H), 6.89 (d, 1 arom. H, J=8.4 Hz), 6.82 (d, 1 arom. H, J=8.4 Hz), 4.94 (s, CH-5), 3.81 (s, $C3-OCH_3$), 3.55 (s, $CH_3N^+$, axial).

EXAMPLE 47

Synthesis of (17R)-17-cyclopropylmethyl-4,5α-epoxy-3-hydroxy-17-methyl-6-oxo-14β-[(2-phenylbenzyl)oxy]morphinanium-iodide (compound 50)

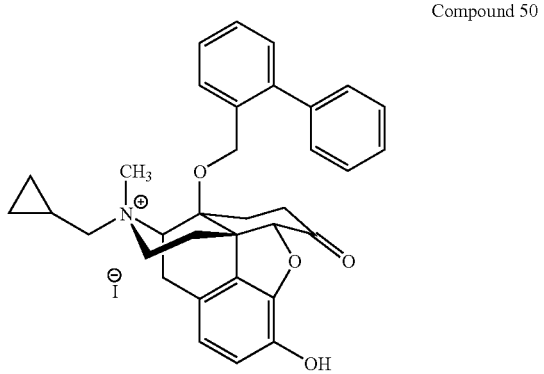

Compound 50

NaH (1.51 g, 62.9 mmol) (obtained from 2.51 g of a 60% NaH dispersion in oil by washing with petroleum ether) was added to a solution of 3-benzyloxy-17-cyclopropylmethyl-4,5α-epoxy-14β-hydroxymorphinan-6-spiro-2'-(1,3-dioxolane) (see Example 46) (5.99 g, 12.6 mmol) in 75 ml water-free N,N-dimethylformamide under $N_2$ at 0° C. (bath temperature) under stirring. After 20 min. 2-phenylbenzyl bromide (4.04 g, 16.4 mmol) was added and the mixture stirred for 20 min at 0° C. (bath temperature), then for 2 h at room temperature. Then small pieces of ice were added until no more hydrogen was given off, the mixture was poured onto 200 ml water and extracted with dichloromethane (1×100 ml, 2×75 ml), the combined organic phases were washed with water (5×300 ml) and saturated sodium chloride solution (1×100 ml), dried over sodium sulphate and evaporated down. From the evaporation residue (7.90 g of brown oil) 3.52 g were purified using column chromatography (silica gel; $CH_2Cl_2$/MeOH/conc. $NH_4OH$ 250:2.5:0.5). A yellowish oil (2.83 g) was produced which was dissolved in 15 ml ether and converted into the hydrochloride with etherial HCl. In this way 2.20 g of colourless crystals of 3-benzyloxy-17-cyclopropylmethyl-4,5α-epoxy-14β-[(2-phenylbenzyl)oxy]morphinan-6-spiro-2'-(1,3-dioxolane) hydrochloride was obtained. Fp. 142-144° C.; MS (CI): 642 ($M^+$+1); $^1$H-NMR of the purified base (DMSO-$d_6$): δ 7.70-7.25 (m, 14 arom. H), 6.76 (d, 1 arom. H, J=8.4 Hz), 6.53 (d, 1 arom. H, J=8.4 Hz), 5.10 (s, 2H, $C3-OCH_2Ph$), 4.63 (d, 1H, $C14-OCH_2$, J=10.6 Hz), 4.46 (s, CH-5), 4.34 (d, 1H, $C14-OCH_2$, J=10.6 Hz), 4.10-3.69 (m, 4H, $OCH_2CH_2O$).

A solution of 3-benzyloxy-17-cyclopropylmethyl-4,5α-epoxy-14β-[(2-phenylbenzyl)oxy]morphinan-6-spiro-2'-(1,3-dioxolane) hydrochloride (2.10 g, 3.10 mmol) in 40 ml of a mixture of conc. HCl/MeOH (4:9) was reflux heated for 1.5 h. After cooling the mixture was poured onto 100 ml of ice, alkalised with conc. $NH_4OH$ and extracted with dichloromethane (1×100 ml, 4×75 ml), the combined organic phases washed with water (2×150 ml) and a saturated sodium chloride solution (1×100 ml), dried over sodium sulphate and evaporated down. A yellow oil (1.90 g) was obtained, which was purified using column chromatography (silica gel; $CH_2Cl_2$/MeOH/conc. $NH_4OH$ (250:3:0.5)). This gave a yellowish oil (0.7 g, 42%) of which 0.16 g was dissolved in 5 ml ether and converted to the hydrochloride with etherial HCl. 0.12 g of colourless crystals of 17-cyclopropylmethyl-4,5α-epoxy-3-hydroxy-14ββ-[(2-phenylbenzyl)oxy]morphinan-6-one hydrochloride was isolated. Fp. 181-186° C.; MS (CI): 508 ($M^+$+1); IR (KBr): 1725 (C=O) $cm^{-1}$; $^1$H-NMR (DMSO-$d_6$, δ in ppm): 9.58 (s, OH), 8.33 (s, wide, $HN^+$), 7.95-7.25 (m, 9 arom. H), 6.72 (d, 1 arom. H, J=8.0 Hz), 6.64 (d, 1 arom. H, J=8.0 Hz), 5.14 (s, CH-5), 4.84 (d, 1H, $C14-OCH_2$—, J=12.4 Hz), 4.56 (d, 1H, $C14-OCH_2$—R, J=12.4 Hz).

A solution of 17-cyclopropylmethyl-4,5α-epoxy-3-hydroxy-14β-[(2-phenylbenzyl)oxy]morphinan-6-one (0.39 g, 0.76 mmol) and methyl iodide (0.54 g, 3.79 mmol) in 6 ml of water-free acetonitrile was stirred under $N_2$ at 40° C. (bath temperature) for 2 days and then evaporated down. The residue (0.5 g of brown oil) was purified using column chromatography (silica gel; $CH_2Cl_2$/MeOH 250:4). Yield: 0.02 g (4%) of beige crystals of the compound 50. Fp. 219-221° C.; MS (CI): 522 ($M^+$); IR (KBr): 1725 (C=O) $cm^{-1}$; $^1$H-NMR (DMSO-$d_6$): δ 9.53 (s, OH), 7.68-7.25 (m, 9 arom. H), 6.67 (s, 2 arom. H), 4.73 (d, $C14-OCH_2$), 4.61 (s, CH-5), 3.26 (s, $CH_3N^+$, axial).

EXAMPLE 48

Synthesis of (17R)-14β-[(4-chlorobenzyl)oxy]-17-cyclopropylmethyl-4,5α-epoxy-3-hydroxy-17-methyl-6-oxomorphinanium-iodide (compound 51)

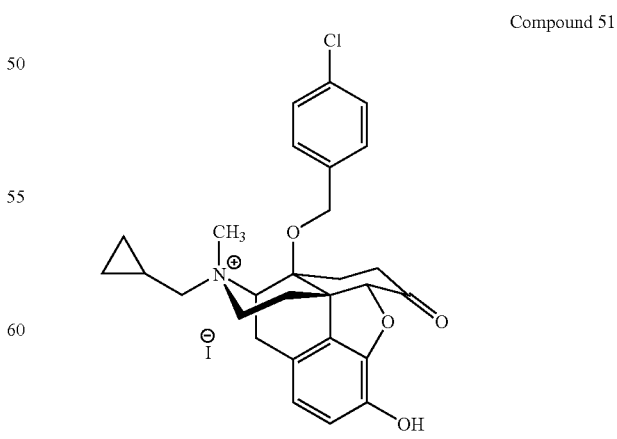

Compound 51

NaH (1.28 g, 53.3 mmol) (obtained from 2.13 g of a 60% NaH dispersion in oil by washing with petroleum ether) was added to a solution of 3-(benzyloxy)-17-(cyclopropylmethyl)-4,5α-epoxy-14β-hydroxymorphinan-6-spiro-2'-(1,3-dioxolane) (see Example 48) (5.00 g, 10.6 mmol) in 75 ml water-free N,N-dimethylformamide under $N_2$ at 0° C. (bath temperature) under stirring. After 20 min. 4-chlorobenzyl bromide (2.95 g, 14.3 mmol) was added and the mixture first stirred for 30 min at 0° C. (bath temperature), then for 1.5 h at room temperature. Then small pieces of ice were added until no more hydrogen was given off, the mixture was poured onto 400 ml water and extracted with dichloromethane (3×100 ml), the combined organic phases were washed with water (5×400 ml) and saturated sodium chloride solution (1×100 ml), dried over sodium sulphate and evaporated down. The evaporation residue (6.45 g of yellow oil) was crystallised out of methanol. Yield: 4.72 g (75%) of colourless crystals of 3-benzyloxy-14β-[(4-chlorobenzyl)oxy]-17-cyclopropylmethyl-4,5α-epoxymorphinan-6-spiro-2'-(1,3-dioxolane). Fp. 122-125° C.; MS (CI): 600 (M$^+$+1); $^1$H-NMR (DMSO-d$_6$ δ in ppm): 7.53-7.35 (m, 9 arom. H), 6.78 (d, 1 arom. H, J=8.4 Hz), 6.57 (d, 1 arom. H, J=8.4 Hz), 5.11 (d, 2H, C$_3$—OC$\underline{H_2}$Ph), 4.65 (d, 1H, C$_{14}$-OC$\underline{H_2}$, J=11.2 Hz), 4.23 (s, CH-5), 4.30 (d, 1H, C14-OC$\underline{H_2}$, J=11.2 Hz), 4.10-3.70 (m, 4H, OCH$_2$CH$_2$O).

A solution of 3-benzyloxy-14β-[(4-chlorobenzyl)oxy]-17-cyclopropylmethyl-4,5α-epoxymorphinan-6-spiro-2'-(1,3-dioxolane) (4.60 g, 7.66 mmol) in 100 ml of a mixture of conc. HCl/MeOH (4:9) was reflux heated for 1.5 h. After cooling the reaction mixture was poured onto 300 ml of ice, alkalised with conc. NH$_4$OH, extracted with dichloromethane (3×150 ml), the combined organic phases were washed with water (2×150 ml) and a saturated sodium chloride solution (1×100 ml), dried over sodium sulphate and evaporated down. The evaporation residue (4.86 g of yellow oil) was purified using column chromatography (silica gel; CH$_2$Cl$_2$/MeOH/conc. NH$_4$OH 250:3:0.5). This gave a yellowish oil (1.18 g, 33%) of which 0.26 g was dissolved in 5 ml ether and converted to the hydrochloride with etherial HCl. 0.23 g of colourless crystals of 14β-[(4-chlorobenzyl)oxy]-17-cyclopropylmethyl-4,5α-epoxy-3-hydroxymorphinan-6-one hydrochloride was isolated. Fp. 195-200° C.; MS (CI): 466.1 (M$^+$+1); IR (KBr): 1725 (C=O) cm$^{-1}$; $^1$H-NMR (DMSO-d$_6$, δ in ppm): 9.59 (s, OH), 8.63 (s, wide, HN$^+$), 7.61 (d, 2 arom. H, C14-OCH$_2$Ph—Cl, J=8.4 Hz), 7.47 (d, 2 arom. H, C14-OCH$_2$Ph—Cl, J=8.4 Hz), 6.73 (d, 1 arom. H, J=8.2 Hz), 6.68 (d, 1 arom. H, J=8.0 Hz), 5.08 (s, CH-5), 4.80 (d, 1H, C14-OC$\underline{H_2}$, J=12 Hz), 4.72 (d, 1H, C14-OC$\underline{H_2}$, J=12 Hz).

A solution of 14β-[(4-chlorobenzyl)oxy]-17-cyclopropylmethyl-4,5α-epoxy-3-hydroxymorphinan-6-one (0.50 g, 1.07 mmol) and methyl iodide (0.76 g, 5.37 mmol) in 8 ml of water-free acetonitrile was stirred under N$_2$ at 40° C. (bath temperature) for 6 days and then evaporated down. The residue (0.56 g of brown oil) was purified using column chromatography (silica gel; CH$_2$Cl$_2$/MeOH 250:4). Yield: 0.07 g (11%) of beige crystals of the compound 51. Fp. 214-219° C.; MS (CI): 480 (M$^+$); IR (KBr): 1733 (C=O) cm$^{-1}$; $^1$H-NMR (DMSO-d$_6$ δ in ppm): 9.57 (s, OH), 7.57 (d, 2 arom. H, C14-OCH$_2$Ph—Cl, J=8.6 Hz), 7.48 (d, 2 arom. H, C14-OCH$_2$Ph—Cl, J=8.6 Hz), 6.71 (s, 2 arom. H), 5.10 (s, CH-5), 4.86 (d, 1H, C14-OCH$_2$, J=11.4 Hz), 4.75-4.66 (m, 3H, C14-OCH$_2$ and CH-9), 3.44 (s, CH$_3$N$^+$, axial).

EXAMPLE 49

Synthesis of 17(R)-4,5α-epoxy-3-hydroxy-14β-methoxy-17-methyl-6-oxo-17-(2-phenylethyl)morphinanium-iodide (compound 52)

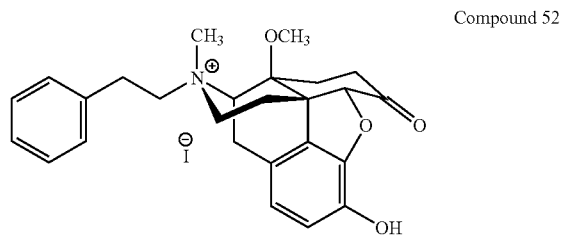

Compound 52

A mixture of 4,5α-epoxy-3,14β-dimethoxymorphinan-6-one (Kobylecki et al., J. Med. Chem., 1989, 25, 2, pp. 116-120) (1.44 g, 4.57 mmol), potassium carbonate (4.11 g, 29.7 mmol), 2-phenylethyl bromide (1.1 g, 5.94 mmol) and 20 ml of N,N-dimethylformamide was stirred for 5.5 h at 80° C. (be temperature) under N$_2$. Then 200 ml of water was added to it and extraction took place with dichloromethane (4×50 ml). The combined organic phases were washed with water (6×130 ml) dried over sodium sulphate and evaporated down. Yield: 1.95 g of yellowish oil of 4,5α-epoxy-3,17-dimethoxy-17-(2-phenylethyl)morphinan-6-one, which was used unmodified for the next synthesis step. Analytical data: $^1$H-NMR (CDCl$_3$, δ in ppm): 7.30-7.18 (m, 5 arom. H), 6.69 (d, 1 arom. H, J=8.0 Hz), 6.60 (d, 1 arom. H, J=8.0 Hz), 4.64 (s, CH-5), 3.89 (s, C3-OCH$_3$), 3.18 (s, C14-OCH$_3$).

A solution of 4,5α-epoxy-3,14β-dimethoxy-17-(2-phenylethyl)morphinan-6-one (2.4 g, 5.72 mmol) 25 ml of 48% HBr was reflux heated for 13 min. Then the solution was cooled, poured onto 100 ml ice, alkalised with conc. NH$_4$OH and extracted with dichloromethane (5×50 ml). The combined organic phases were washed with a saturated sodium chloride solution (3×150 ml), dried over sodium sulphate and evaporated down. The evaporation residue (2.40 g of brown oil) was purified using column chromatography (silica gel; CH$_2$Cl$_2$/MeOH/conc. NH$_4$OH 250:2:0.5). Yield: 0.4 (17%) of dark yellow oil of which 0.04 g was dissolved in 5 ml ether and the hydrochloride obtained with etherial HCl. 0.02 g of colourless crystals of 4,5α-epoxy-3-hydroxy-14β-methoxy-17-(2-phenylethyl)morphinan-6-one hydrochloride was isolated. Fp. 259-262° C.; MS (CI): 406 (M$^+$+1); IR (KBr): 1731 (C=O) cm$^{-1}$; $^1$H-NMR (DMSO-d$_6$ δ in ppm): 9.52 (s, OH), 9.28 (s, wide, HN$^+$), 7.38-7.2 (m, 5 arom. H), 6.70 (s, 2 arom. H, CH-1 and CH-2), 4.96 (s, CH-5), 3.40 (s, C14-OCH$_3$).

A solution of 4,5α-epoxy-3-hydroxy-14β-methoxy-17-(2-phenylethyl)morphinan-6-one (0.32 g, 0.7 mmol) and methyl iodide (0.56 g, 3.92 mmol) in 6 ml of water-free acetonitrile was stirred under N$_2$ 40° C. (bath temperature) for 2 days and then evaporated down. The residue (0.32 g of brown oil) was purified using column chromatography (silica gel; CH$_2$Cl$_2$/MeOH 250:2). Yield: 0.07 g (16%) of colourless crystals of the compound 52. Fp. 180-181° C.; MS (CI): 420 (M$^+$+1); IR (KBr): 1727 (C=O) cm$^{-1}$; $^1$H-NMR (D$_2$O, δ in ppm): 7.17-7.14 (m, 5 arom. H), 6.56 (s, 2 arom. H), 5.18 (s, CH-5), 3.64 (s, CH$_3$N$^+$, axial), 3.44 (s, OCH$_3$).

EXAMPLE 50

4,5α-epoxy-17-methyl-14β-[(3-phenylpropyl)oxy]morphinan-6-one (compound 53)

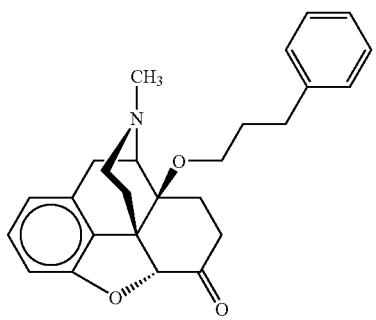

Compound 53

Water-free $K_2CO_3$ (5.67 g, 41.06 mmol) and 5-chloro-1-phenyl-1H-tetrazol (3.02 g, 16.73 mmol) were added to a solution of 4,5α-epoxy-3-hydroxy-17-methyl-14β-[(3-phenylpropyl)oxy]morphinan-6-one (see Example 36) (6.38 g, 15.20 ml) in 40 ml of water-free dimethylformamide and this mixture stirred for 23 h at room temperature. After the addition of 300 ml $H_2O$, extraction took place with $CH_2Cl_2$ (3×75 ml). The combined organic phases were washed with $H_2O$ (2×200 ml) and saturated NaCl solution (3×250 ml), dried over $Na_2SO_4$ and evaporated down. The evaporation residue (7.48 g of yellowish oil) was purified using column chromatography (silica gel; $CH_2Cl_2$/MeOH/conc. $NH_4OH$ (250:2: 0.5)). The appropriate fractions were evaporated down. This gave 6.41 g of yellow oil (4,5α-epoxy-17-methyl-14β-[(3-phenylpropyl)oxy]-3-[(1-phenyl-1H-tetrazol-5-yl)oxy]morphinan-6-one; 75%), which was used for the next reaction step without further purification. For analytical purposes a small quantity was crystallised out of ether and in this way 4,5α-epoxy-17-methyl-14β-[(3-phenylpropyl)oxy]-3-[(1-phenyl-1H-tetrazol-5-yl)oxy]morphinan-6-one was obtained as colourless crystals. Fp. 117-119° C.; MS (CI): 564 ($M^+$+1); IR (KBr): 1723 (C=O) $cm^{-1}$; $^1$H-NMR (DMSO-$d_6$): δ 7.88-7.837 (m, 2 arom. H), 7.73-7.62 (m, 3 arom. H), 7.30-7.16 (m, 6 arom. H), 6.85 (d, J=8.4 Hz, 1 arom. H), 4.93 (s, CH-5), 2.29 (s, 3H, N17-C$\underline{H}_3$).

A mixture of 4,5α-epoxy-17-methyl-14β-[(3-phenylpropyl)oxy]-3-[(1-phenyl-1H-tetrazol-5-yl)oxy]morphinan-6-one (6.20 g, 11.00 mmol), 10% Pd/C catalyst (2.48 g) and 100 ml glacial acetic acid was hydrogenated at 50 psi and 40° C. for 17 h. After filtering off the catalyst, the filtrate was reduced down to a volume of 30 ml, 150 ml of ice/water mixture was added to it and after alkalising with conc. $NH_4OH$ it was extracted with $CH_2Cl_2$ (1×100 ml, 3×75 ml). The combined organic phases were washed with saturated NaCl solution (4×200 ml), dried over $Na_2SO_4$ and evaporated down. The evaporation residue (4.15 g of yellowish oil, DC pure) was crystallised out of a little methanol and in this way 3.20 g (72%) of the compound 53 was obtained as colourless crystals. Fp. 105-109° C.; MS (CI): 404 ($M^+$+1); IR (KBr): 1721 (C=O) $cm^{-1}$; $^1$H-NMR (DMSO-$d_6$): δ 7.29-7.16 (m, 5 arom. H), 7.04 (t, J=8.0 Hz, 1 arom. H), 6.73 (d, J=8.0 Hz, 1 arom. H), 6.64 (d, J=8.0 Hz, 1 arom. H), 4.75 (s, 1H, C5-H), 2.28 (s, 3H, N17-C$\underline{H}_3$).

EXAMPLE 51

17-(cyclopropylmethyl)-4,5α-epoxy-14β-[(3-phenylpropyl)oxy]morphinan-6-one hydrochloride (compound 54.HCl)

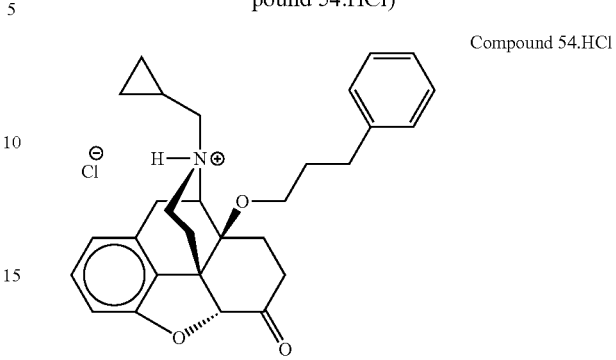

Compound 54.HCl $NaHCO_3$ (3.33 g, 39.65 mmol) and 1-chloroethyl chloroformate (4.32 ml, 39.65 mmol) were added to a solution of 53 (3.20 g, 7.93 mmol) in 40 ml of ethanol-free 1,2-dichloroethane. This mixture was stirred for 13.5 h at 60° C. (oil bath temperature) under $N_2$. Then filtration took place from the inorganic residue, the residue was washed with ethanol-free 1,2-dichloroethane and the filtrate evaporated down. The evaporation residue (3.7 g of yellow-brown oil, DC-pure) was—without further purification and characterisation—reflux heated in a mixture of 15 ml conc. HCl and 35 ml MeOH for 1 h. The reaction solution was evaporated down and the evaporation residue crystallised out of MeOH/$Et_2O$. 2.77 g (82%) of 4,5α-epoxy-14β-[(3-phenylpropyl)oxy]morphinan-6-one hydrochloride was isolated. Fp. >225° C. (decomposition); MS (CI): m/z 390 ($M^+$+1); IR (KBr): 1729 (C=O) $cm^{-1}$; $^1$H-NMR (DMSO-$d_6$): δ 9.25 (s, wide, 1H, $^+$HN), 8.11 (s, wide, 1H, $^+$HN), 7.34-7.12 (m, 5 arom. H), 7.16 (t, j=8.0 Hz, 1 arom. H), 6.85 (d, J=8.0 Hz, 1 arom. H), 6.77 (d, J=8.0 Hz, 1 arom. H), 4.96 (s, 1H, C5-H), 4.28 (ps-d, C9-H).

Water-free $K_2CO_3$ (2.13 g, 15.40 mmol) and cyclopropylmethyl bromide (0.64 ml, 6.67 mmol) were added to a solution of 4,5α-epoxy-14β-[(3-phenylpropyl)oxy]morphinan-6-one hydrochloride (2.36 g, 5.55 mmol) in 20 ml of water-free dimethylformamide under $N_2$. This mixture was stirred at a bath temperature of 80° C. under $N_2$. Since a DC check after 7 h showed that the reaction had not yet completely finished, a further 0.50 ml of cyclopropylmethyl bromide (5.24 mmol) was added. After a further hour the reaction had finished and after cooling filtration from the inorganic material took place, the residue was washed with $CH_2Cl_2$ and the filtrate evaporated down. The evaporation residue was dissolved in 150 ml $CH_2Cl_2$, washed with $H_2O$ (5×150 ml) and saturated NaCl solution (150 ml), dried over $Na_2SO_4$ and evaporated down. This gave 2.43 g (99%) of 17-(cyclopropylmethyl)-4,5α-epoxy-14β-[(3-phenylpropyl)oxy]morphinan-6-one (54) as a yellowish oil which was used for the next reaction without further purification. 0.30 g of the oil was dissolved in ether and after the addition of etherial HCl 0.23 g of 17-(cyclopropylmethyl)-4,5α-epoxy-14β-[(3-phenylpropyl)oxy]morphinan-6-one hydrochloride (compound 54.HCl) was isolated as a colourless powder. Fp. 145-150° C.; MS (CI): m/z 444 ($M^+$+1); IR (KBr): 1726 (C=O) $cm^{-1}$; $^1$H-NMR (DMSO-$d_6$): δ 8.26 (s, wide, 1H), 7.31-7.14 (m, 5 arom. H), 7.18 (t, J=8.0 Hz, 1 arom. H), 6.85 (d, J=8.0 Hz, 1 arom. H), 6.78 (d, J=8.0 Hz, 1 arom. H), 4.96 (s, 1H, C5-H), 4.55 (ps-d, C9-H), 1.09-1.06 (m, 1H, N17-$CH_2C\underline{H}(CH_2)_2$), 0.75-0.69 (m, 2H, N—$CH_2CH(C\underline{H}_2)_2$), 0.55-0.42 (m, 2H, N—$CH_2CH(C\underline{H}_2)_2$).

EXAMPLE 52

17-(cyclopropylmethyl)-4-hydroxy-14β-[(3-phenyl-propyl)oxy]morphinan-6-one hydrochloride (compound 55.HCl)

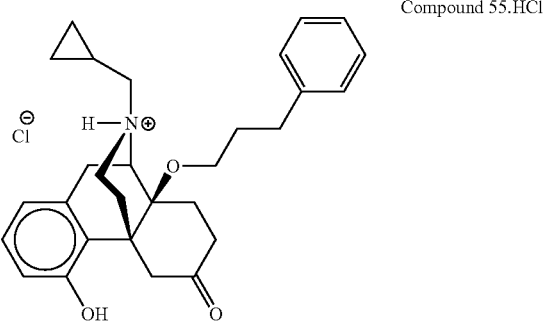

Compound 55.HCl

NH$_4$Cl (0.72 g, 13.46 mmol) was added to a reflux boiling solution of 54 (1.2 g, 2.71 mmol) in 50 ml MeOH under stirring. 0.88 g (13.46 mmol) activated zinc powder was added in small portions to this mixture. This mixture was stirred under reflux for 80 min., then cooled to room temperature and filtered off from the inorganic residue. The inorganic residue was washed with hot methanol and the filtrate evaporated down. 50 ml H$_2$O was added to the evaporation residue which was then alkalised with conc. NH$_4$OH. This mixture was extracted with CH$_2$Cl$_2$ (3×80 ml), the combined organic phases washed with saturated NaCl solution (5×100 ml), dried over Na$_2$SO$_4$ and evaporated down. 1.20 g (99%) of 17-(cyclopropylmethyl)-4-hydroxy-14β-[(3-phenylpropyl)oxy]morphinan-6-one (55) was obtained as a yellowish oil which was used for the next reaction step without further purification. For analytical purposes 0.08 g of the oil was dissolved in ether and after the addition of etherial HCl 0.059 g of 0.17-(cyclopropylmethyl)-4-hydroxy-14β-[(3-phenylpropyl)oxy]morphinan-6-one hydrochloride (55.HCl) was isolated as a colourless powder. Fp. >170° C. (decomposition); MS (CI): m/z 446 (M$^+$+1); IR (KBr): 1709 (C=O) cm$^{-1}$; $^1$H-NMR (DMSO-d$_6$): δ 9.82 (s, 1H, C4-OH), 8.43 (s, wide, 1H, $^+$N17-H), 7.30-7.20 (m, 5 arom. H, C14-O(CH$_2$)$_3$Ph), 7.03 (t, J=8.0 Hz, 1 arom. H, C2-H), 6.66 (m, 2 arom. H), 4.40 (ps-d, C9-H), 1.09 (m, 1H, N17-CH$_2$CH(CH$_2$)$_2$), 0.70-0.67 (m, 2H, N17-CH$_2$CH(CH$_2$)$_2$), 0.52-0.40 (m, 2H, N17-CH$_2$CH(CH$_2$)$_2$).

EXAMPLE 53

17-(cyclopropylmethyl)-4-methoxy-14β-[(3-phenyl-propyl)oxy]morphinan-6-one hydrochloride (56.HCl)

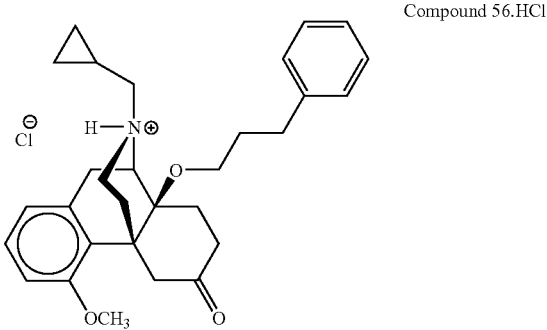

Compound 56.HCl

Water-free K$_2$CO$_3$ (0.37 g, 2.69 mmol) and 0.46 g (2.69 mmol) of phenyltrimethyl ammonium chloride were added to a solution of 55 (0.40 g, 0.90 mmol) in 6 ml of water-free dimethylformamide under N$_2$. This mixture was stirred for 3.5 h at a bath temperature of 80° C. under N$_2$. After cooling filtration from the inorganic material took place, the residue was washed with CH$_2$Cl$_2$ and the filtrate evaporated down. The evaporation residue was dissolved in 100 ml CH$_2$Cl$_2$, washed with saturated NaCl solution (4×150 ml), dried with Na$_2$SO$_4$ and evaporated down. The evaporation residue (0.30 g) was purified using column chromatography (silica gel; CH$_2$Cl$_2$/MeOH/conc. NH$_4$OH (250/4/0.5)) and the appropriate fractions evaporated down. The evaporation residue (0.23 g) was dissolved in ether and after the addition of etherial HCl, 0.22 g (48%) of the compound 56.HCl was isolated as a colourless powder. Fp. 121-126° C.; MS (CI): m/z 460 (M$^+$+1); IR (KBr): (C=O) 1710 cm$^{-1}$; $^1$H-NMR (DMSO-d$_6$): δ 8.34 (s, wide, 1H, $^+$N—H), 7.30-7.16 (m, 5 arom. H), 7.22 (t, J=8.0 Hz, 1 arom. H), 6.88 (d, J=8.0 Hz, 1 arom. H), 6.82 (d, J=8.0 Hz, 1 arom. H), 4.42 (ps-d, C9-H), 3.77 (s, 3H, C4-OCH$_3$), 1.08 (m, 1H, N—CH$_2$CH(CH$_2$)$_2$), 0.70-0.42 (m, 4H, N—CH$_2$CH(CH$_2$)$_2$).

EXAMPLE 54

4-(n-butoxy)-17-(cyclopropylmethyl)-14β-[(3-phenylpropyl)oxy]morphinan-6-one hydrochloride (57.HCl)

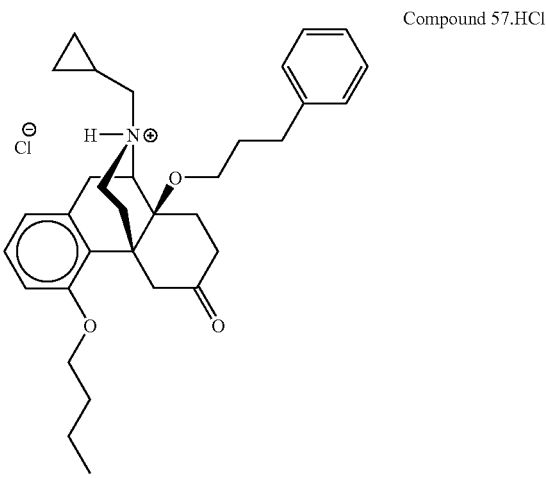

Compound 57.HCl

Water-free K$_2$CO$_3$ (0.55 g, 4.01 mmol) and iodo-butane (0.31 ml, 2.67 mmol) were added to a solution of 55 (0.60 g, 1.34 mmol) in 5 ml of water-free dimethylformamide under N$_2$. This mixture was stirred for 7 h at a bath temperature of 90° C. under N$_2$. Then filtration from the inorganic material took place, the residue was washed with CH$_2$Cl$_2$ and the filtrate evaporated down. The evaporation residue was dissolved in 100 ml CH$_2$Cl$_2$, washed with saturated NaCl solution (3×150 ml), dried over Na$_2$SO$_4$ and evaporated down. The evaporation residue (0.43 g of brown oil) was purified using column chromatography (silica gel; CH$_2$Cl$_2$/MeOH/conc. NH$_4$OH (250:4:0.5)) and the appropriate fractions evaporated down. The evaporation residue (0.26 g) was dissolved in ether and after the addition of etherial HCl, 0.19 g (26%) 57.HCl was isolated as a colourless powder. Fp. 172-177° C.; MS (CI): m/z 502 (M$^+$+1); IR (KBr): (C=O) 1711 cm$^{-1}$; $^1$H-NMR (DMSO-d$_6$): δ 8.52 (s, wide, 1H, $^+$N—H), 7.30-7.15 (m, 6 arom. H), 6.86 (d, J=8.0 Hz, 1 arom. H), 6.80 (d, J=8.0 Hz, 1 arom. H), 4.42 (ps-d, C9-H), 3.95 (t, 2H, J=6.4 Hz, C4-OC$\underline{H_2}$(CH$_2$)$_2$CH$_3$), 1.13-1.06 (m, 1H, N—CH$_2$C $\underline{H}$(CH$_2$)$_2$), 0.95 (t, 3H, J=7.3 Hz, C4-O(CH$_2$)$_3$C$\underline{H_3}$), 0.69-0.40 (m, 4H, N—CH$_2$CH(C$\underline{H_2}$)$_2$).

EXAMPLE 55

Opioid Receptor Binding Studies

Opioid receptor binding studies were carried out on rat's brain homogenisates using [$^3$H]DAMGO (μ-receptor agonist) as radio-ligand and under strict conformance to an earlier published specification (M. Spetea et al., Neurochemical Research 1998, Vol. 23, pp. 1213-1218).

The compounds 8, 17, 17a 17b, 38, 40-43, 48, 49, and 54-56 show very high affinity to p-opioid receptors which are primarily responsible for analgesia (Table 1). All have a clearly higher affinity than the antagonist cyprodime (see H. Schmidhammer et al., J. Med. Chem. 1995, 38, 3071-3077), which is selective to p-opioid receptors. The compounds 8, 17, 17a 17b, 40, 48, and 54-56 show extremely high affinity to p-opioid receptors (in the subnanomolar range). Morphine and the opioid antagonist 3-hydroxycyprodime (see H. Schmidhammer et al., J. Med. Chem. 1995, 38, 3071-3077) show in comparison to these two compounds clearly lower affinity to μ-opioid receptors, whereas 14-methoxymetopon exhibits similar affinity.

TABLE 1

Opioid receptor binding studies of the compounds 8, 17, 17a 17b, 38, 40-43, 48, 49, and 54-56, morphine, 14-methoxymetopon, cyprodime and 3-hydroxycyprodime.

| Compound | $K_i$ (nM) (μ-receptors) |
|---|---|
| 8 | 0.34 |
| 17 | 0.73 |
| 17a | 0.62 |
| 17b | 0.20 |
| 38 | 4.11 |
| 40 | 0.37 |
| 41 | 2.32 |
| 42 | 5.93 |
| 43 | 1.33 |
| 48 | 0.93 |
| 49 | 1.78 |
| 54 | 0.84 |
| 55 | 0.40 |
| 56 | 0.34 |
| Morphine | 6.55 |
| 14-methoxymetopon | 0.55 |
| Cyprodime | 23.7 |
| 3-hydroxycyprodime | 6.15 |

EXAMPLE 56

Analgesia Tests a) "Hot-Plate Test"

A test on mice ("hot-plate test") was carried out as described earlier (E. L. May et al., J. Med. Chem. 2000; 43, 5030-5036).

All tested substances show substantially higher analgesic activity than morphine. The compounds 6-11, 17a, 17b and 53 show extremely high analgesic activity which is significantly higher than that of the reference substance 14-methoxymetopon (see Zs. Furst et al., Eur. J. Pharmacol. 1993; 236: 209-215). Compounds 4 and 32 show in comparison to the compounds 6-11 somewhat lower analgesic activity, because these compounds exhibit an ether function (methoxy group) in Position 3, from which it is known that it reduces the analgesic activity in comparison to the 3-hydroxy analogues. However, the analgesic activity of the compounds 4 and 32 is still surprisingly high. Also, the analgesic activity of the compound 17 with a different ether function (propargyloxy group) in Position 3 is surprisingly high.

TABLE 2

"Hot-plate Test" of compounds 4, 6-11, 17, 17a, 17b, 32, 53, morphine and 14-methoxymetopon.

| Compound | $ED_{50}$ (μg/kg, sc$^a$) |
|---|---|
| 4 | 60 |
| 6 | 5.9 |
| 7 | 3.7 |
| 8 | 2.3 |
| 9 | 11.7 |
| 10 | 1.3 |
| 11 | 1.7 |
| 17 | 38 |
| 17a | 2.6 |
| 17b | 0.10 |
| 32 | 22 |
| 53 | 3.0 |
| Morphine | 850 |
| 14-methoxymetopon | 30 |

$^a$sc = subcutaneous application b) "Mouse Tail Flick Test"

To determine the analgesic activity of non-quaternised compounds, the "Mouse Tail Flick Test" was carried out as earlier described (E. L. May et al., J. Med. Chem. 2000; 43, 5030-5036).

All tested substances show substantially higher analgesic activity than morphine. The compounds 6-8, 10, 11, 17a, 17b and 53 show extremely high analgesic activity which is significantly higher than that of the reference substance 14-methoxymetopon (see Zs. Fürst et al., Eur. J. Pharmacol. 1993; 236: 209-215). Compound 4 shows in comparison to the compounds 6-8, 10, 11, 17a, 17b and 53 a somewhat lower analgesic activity, because this compound exhibits a methoxy group in Position 3, from which it is known that it reduces the analgesic activity in comparison to the 3-hydroxy analogues. However, the analgesic activity of compound 4 is surprisingly high. Similarly, compounds 17a and 32, which surprisingly have a very high analgesic activity, have a methoxy group in Position 3. The most active compound in this series, compound 17b, with an $ED_{50}$ (μg/kg, sc) of 0.08, is more active than the most active analgesically effective substances recognized, etorphine and dihydroetorphine (M. D. Aceto et al., Eur. J. Pharmacol 1997; 338, 215-223).

TABLE 3

"Mouse Tail Flick Test" of compounds 4, 6-8, 10, 11, 17, 17a, 17b, 32, 53, morphine and 14-methoxymetopon.

| Compound | $ED_{50}$ (μg/kg, sc$^a$) |
|---|---|
| 4 | 84 |
| 6 | 5.6 |
| 7 | 8.2 |
| 8 | 3.2 |
| 10 | 7.0 |
| 11 | 1.6 |
| 17 | 21 |
| 17a | 4.4 |

TABLE 3-continued

"Mouse Tail Flick Test" of compounds
4, 6-8, 10, 11, 17, 17a, 17b, 32, 53,
morphine and 14-methoxymetopon.

| Compound | $ED_{50}$ (μg/kg, sc[a]) |
|---|---|
| 17b | 0.08 |
| 32 | 14 |
| 53 | 0.4 |
| Morphine | 1920 |
| 14-methoxymetopon | 30 |

[a]sc = subcutaneous application c) "Rat Tail Flick Test"

To determine the analgesic activity of quaternised compounds, a test on rats, the "Rat Tail Flick Test", was used. The test was carried out as described earlier (Zs. Fürst et al., Eur. J. Pharmacol. 1993; 236: 209-215).

As quaternary ammonium salts, compounds 38 and 42 show a very high analgesic effect—both are substantially more active than morphine after subcutaneous application (Table 3). Compound 42 is somewhat less active than 14-methoxymetopon after subcutaneous application. After intracerebroventricular application, compound 42 is extremely active, which is an indication that it can overcome the blood-brain barrier only to a limited degree and shows its effectiveness therefore primarily in the periphery (outside of the central nervous system). This goes with a very reduced side-effect rate which is relevant to central side effects such as nausea, vomiting, sedation, dizziness, confusion, respiratory depression and mania.

TABLE 4

"Rat Tail Flick Test" of compounds 38, 42, morphine and 14-methoxymetopon.

| Compound | $ED_{50}$ (μg/kg, sc[a]) | $ED_{50}$ (μg/rat[b], icv[c]) |
|---|---|---|
| 38 | 120 | 12 |
| 42 | 16 | 0.22 |
| Morphine | 1900 | — |
| 14-methoxymetopon | 7.2 | — |

[a]sc = subcutaneous application
[b]The weight of the rats used was 120 g in each case
[c]icv = intracerebroventricular application

EXAMPLE 57

Determination of the Antagonistic Activity

Vas Deferens Preparation of the Mouse

This test was carried out as earlier described using DAMGO (μ-receptor agonist) (S. Garadnay et al., Curr. Med. Chem. 2001, 8, 621-626).

Compound 48 shows surprisingly very high antagonistic activity to p-opioid receptors, which is unusual for quaternised morphinans (Table 4).

Normally quaternised morphinans have a substantially lower activity in comparison to the non-quaternised morphinans. It has substantially higher antagonistic activity than the μ-selective opioid receptor antagonist cyprodime. In comparison to naloxone it has a somewhat lower activity, whereas in comparison to 3-hydroxycyprodime it exhibits a somewhat higher activity. Due to its structure as a quaternary ammonium salt, it can only overcome the blood-brain barrier with difficulty and produces its effect mainly in the periphery. Because of this, it can, for example, be used to counter or prevent obstipation or ileus caused by opioids without the analgesia of the administered opioid being cancelled. In comparison to it, naloxone, cyprodime and 3-hydroxycyprodime pass through the blood-brain barrier relatively easily and therefore also cancel the analgesic effect of opioids.

TABLE 5

Antagonistic $K_e$ values of compounds 48, naloxone, cyprodime and 3-hydroxycyprodime in the Vas Deferens preparation of the mouse.

| Compound | $K_e$ (vM) (μ-receptors) |
|---|---|
| 48 | 2.94 |
| Naloxone | 1.4 |
| Cyprodime | 55.4 |
| 3-hydroxycyprodime | 5.62 |

The invention claimed is:

1. A compound of formula (I),

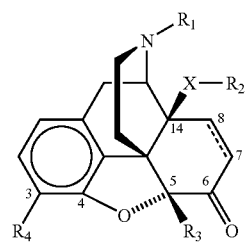

(I)

in which the substituents have the following significance:
R$_1$: C$_2$-C$_6$-alkenyl; C$_2$-C$_6$-alkinyl; C$_3$-C$_{16}$-(cyclical saturated group)alkyl, where alkyl is C$_1$-C$_6$; C$_4$-C$_{16}$-(cyclical saturated group)alkenyl, where alkenyl is C$_2$-C$_6$; C$_4$-C$_{16}$-(cyclical saturated group)alkinyl, where alkinyl is C$_2$-C$_6$; C$_7$-C$_{16}$-arylalkyl, where aryl is C$_6$-C$_{10}$-aryl and alkyl is C$_1$-C$_6$-alkyl; C$_8$-C$_{16}$-arylalkenyl, where aryl is C$_6$-C$_{10}$-aryl and alkenyl is C$_2$-C$_6$-alkenyl; C$_8$-C$_{16}$-arylalkinyl, where aryl is C$_6$-C$_{10}$-aryl and alkinyl is C$_2$-C$_6$-alkinyl;

R$_2$ is C$_2$-C$_6$-alkenyl;

R$_3$: hydrogen; C$_1$-C$_6$-alkyl; C$_2$-C$_6$-alkenyl; C$_7$-C$_{16}$-arylalkyl, where aryl is C$_6$-C$_{10}$-aryl and alkyl is C$_1$-C$_6$-alkyl; C$_8$-C$_{16}$-arylalkenyl, where aryl is C$_6$-C$_{10}$-aryl and alkenyl is C$_2$-C$_6$-alkenyl; alkoxyalkyl, where alkoxy is C$_1$-C$_6$-alkoxy and alkyl is C$_1$-C$_6$-alkyl; CO$_2$(C$_1$-C$_6$-alkyl); CO$_2$H; CH$_2$OH;

R$_4$: C$_1$-C$_6$-alkyloxy; C$_2$-C$_{10}$-alkyloxyalkoxy, where alkyloxy is C$_1$-C$_4$ alkyloxy and alkoxy is C$_1$-C$_6$-alkyloxy; C$_2$-C$_6$-alkenyloxy; C$_2$-C$_6$-alkinyloxy; C$_3$-C$_{16}$-(cyclical saturated group)alkyloxy, where alkyl is C$_1$-C$_6$ alkyl; C$_4$-C$_{16}$-(cyclical saturated group)alkenyloxy, where alkenyl is C$_2$-C$_6$ alkenyl; C$_4$-C$_{16}$-(cyclical saturated group)alkinyloxy where alkinyl is C$_2$-C$_6$ alkinyl; C$_8$-C$_{16}$-arylalkenyloxy, where aryl is C$_6$-C$_{10}$-aryl and alkenyl is C$_2$-C$_6$-alkenyl; C$_8$-C$_{16}$-arylalkinyloxy, where aryl is C$_6$-C$_{10}$-aryl and alkinyl is C$_2$-C$_6$-alkinyl; C$_1$-C$_6$-alkanoyloxy; C$_3$-C$_6$-alkenoytoxy; C$_3$-C$_6$-alkinoyloxy; C$_7$-C$_{16}$-arylalkanoyloxy, where aryl is C$_6$-C$_{10}$-aryl and alkanoyloxy is C$_2$-C$_6$-alkanoyloxy; C$_9$-C$_{16}$-arylalkenoyloxy, where aryl is C$_6$-C$_{10}$-aryl and alkenoyloxy is $C_3$-$C_6$-alkenoyloxy; $C_9$-$C_{16}$-arylalkinoykxy, where aryl is $C_6$-$C_{10}$-aryl and alkinoyloxy is $C_3$-$C_6$-alkinoyloxy;

X is oxygen;

wherein a single or double bond can be present between the carbon atoms of numbers 7 and 8, wherein alkyl, alkenyl and alkinyl can each be branched or unbranched, aryl can be unsubstituted or mono-, di- or trisubstituted, independently in each case, with hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino; $C_5$-$C_6$-cycloalkylamino, $(C_1$-$C_3$-alkanoyl)amido, SH, $SO_3H$, $SO_3(C_1$-$C_3$-alkyl), $SO_2(C_1$-$C_3$-alkyl)$, SO(C_1$-$C_3$-alky), $C_1$-$C_3$-alkylthio or $C_1$-$C_3$-alkanoylthio, and wherein -(cyclical saturated group) is either $C_3$-$C_{10}$-cycloalkyl or a heterocyclic group with 2 to 9 carbon atoms, containing further one or more hetero atoms.

2. A compound of formula (I),

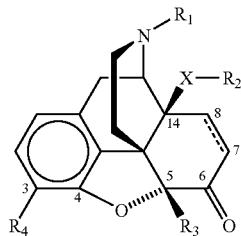

(I)

in which the substituents have the following significance:

$R_1$: $C_2$-$C_6$-alkenyl; $C_2$-$C_6$-alkinyl; $C_3$-$C_{16}$-(cyclical saturated group)alkyl, where alkyl is $C_1$-$C_6$; $C_4$-$C_{16}$-(cyclical saturated group)alkenyl, where alkenyl is $C_2$-$C_6$; $C_4$-$C_{16}$-(cyclical saturated group)alkinyl, where alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl;

$R_2$ is $C_2$-$C_6$-alkenyl;

$R_3$: $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$;

$R_4$: hydrogen; hydroxy; $C_1$-$C_6$-alkyloxy; $C_2$-$C_{10}$-alkyloxyalkoxy, where alkyloxy is $C_1$-$C_4$ alkyloxy and alkoxy is $C_1$-$C_6$-alkyloxy; $C_2$-$C_6$-alkenyloxy; $C_2$-$C_6$-alkinyloxy; $C_3$-$C_{16}$-(cyclical saturated group)alkyloxy, where alkyl is $C_1$-$C_6$ alkyl; $C_4$-$C_{16}$-(cyclical saturated group)alkenyloxy, where alkenyl is $C_2$-$C_6$ alkenyl; $C_4$-$C_{16}$-(cyclical saturated group)alkinyloxy where alkinyl is $C_2$-$C_6$ alkinyl; $C_7$-$C_{16}$-arylalkyloxy, where aryl is $C_6$-$C_{10}$-aryl and alkyl is $C_1$-$C_6$-alkyl; $C_8$-$C_6$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{16}$-aryl and alkinyl is $C_2$-$C_6$-alkinyl; $C_1$-$C_6$-alkanoyloxy; $C_3$-$C_6$-alkenoyloxy; $C_3$-$C_6$-alkinoyloxy; $C_7$-$C_{16}$-arylalkanoyloxy, where aryl is $C_6$-$C_{10}$-aryl and alkanoyloxy is $C_2$-$C_6$-alkanoyloxy; $C_9$-$C_{16}$-arylalkenoyloxy, where aryl is $C_6$-$C_{16}$-aryl and alkenoyloxy is $C_3$-$C_6$-alkenoyloxy; $C_9$-$C_{16}$-arylalkinoyloxy, where aryl is $C_6$-$C_{10}$-aryl and alkinoyloxy is $C_3$-$C_6$-alkinoyloxy;

X is oxygen;

wherein a single or double bond can be present between the carbon atoms of numbers 7 and 8, wherein alkyl, alkenyl and alkinyl can each be branched or unbranched, aryl can be unsubstituted or mono-, di- or trisubstituted, independently in each case, with hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino; $C_5$-$C_6$-cycloalkylamino, $(C_1$-$C_3$-alkanoyl)amido, SH, $SO_3H$, $SO_3(C_1$-$C_3$-alkyl), $SO_2(C_1$-$C_3$-alkyl), $SO(C_1$-$C_3$-alky), $C_1$-$C_3$-alkylthio or $C_1$-$C_3$-alkanoylthio, and wherein -(cyclical saturated group) is either $C_3$-$C_{10}$-cycloalkyl or a heterocyclic group with 2 to 9 carbon atoms, containing further one or more heteroatoms.

3. A pharmaceutical composition comprising (i) a pharmaceutically acceptable carrier and (ii) a compound of formula (I),

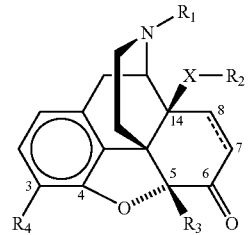

(I)

or a pharmaceutically acceptable addition salt thereof, in which the substituents have the following significance:

$R_1$: $C_2$-$C_6$-alkenyl; $C_2$-$C_6$-alkinyl; $C_3$-$C_{16}$-(cyclical saturated group)alkyl, where alkyl is $C_1$-$C_6$; $C_4$-$C_{16}$-(cyclical saturated group)alkenyl, where alkenyl is $C_2$-$C_6$; $C_4$-$C_{16}$-(cyclical saturated group)alkinyl, where alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl;

$R_2$ is $C_2$-$C_6$-alkenyl;

$R_3$: hydrogen; $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C1$-$C_6$-alkyl); $CO_2H$; $CH_2OH$;

$R_4$: $C1$-$C_6$-alkyloxy; $C_2$-$C_{10}$-alkyloxyalkoxy, where alkyloxy is $C_1$-$C_4$ alkyloxy and alkoxy is $C_1$-$C_6$-alkyloxy; $C_2$-$C_6$-alkenyloxy; $C_2$-$C_6$-alkinyloxy; $C_3$-$C_{16}$-(cyclical saturated group)alkyloxy, where alkyl is $C_1$-$C_6$ alkyl; $C_4$-$C_{16}$-(cyclical saturated group)alkenyloxy, where alkenyl is $C_2$-$C_6$ alkenyl; $C_4$-$C_{16}$-(cyclical saturated group)alkinyloxy where alkinyl is $C_2$-$C_6$ alkinyl; $C_7$-$C_{16}$-arylalkyloxy, where aryl is $C_6$-$C_{10}$-aryl and alkyl is $C1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl arid alkinyl is $C_2$-$C_6$-alkinyl; $C_1$-$C_6$-alkanoyloxy; $C_3$-$C_6$-alkenoyloxy; $C_3$-$C_6$-alkinoyloxy; $C_7$-$C_{16}$-arylalkanoyloxy, where aryl is $C_6$-$C_{10}$-aryl and alkanoyloxy is $C_2$-$C_6$-alkanoyloxy; $C_9$-$C_{16}$-arylalkenoyloxy, where aryl is $C_6$-$C_{10}$-aryl and alkenoyloxy is $C_3$-$C_6$-alkenoyloxy; $C_9$-$C_{16}$-arylalkinoyloxy, where aryl is $C_6$-$C_{10}$-aryl and alkinoyloxy is $C_3$-$C_6$-alkinoyloxy;

X is oxygen;

wherein a single or double bond can be present between the carbon atoms of numbers 7 and 8, wherein alkyl, alkenyl and alkinyl can each be branched or unbranched, aryl can be unsubstituted or mono-, di- or trisubstituted, independently in each case, with hydroxy, halogen, nitro, cyano, tiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino; $C_5$-$C_6$-cycloalkylamino, $(C_1$-$C_3$-alkanoyl)amido, SH, $SO_3H$, $SO_3(C_1$-$C_3$-alkyl), $SO_2(C_1$-$C_3$-alkyl), $SO(C_1$-$C_3$-alkyl), $C_1$-$C_3$-alkylthio or $C_1$-$C_3$-alkanoylthio, and wherein -(cyclical saturated group) is either $C_3$-$C_{10}$-cycloalkyl or a heterocyclic group with 2 to 9 carbon atoms, containing further one or more heteroatoms.

4. A method of treating pain comprising the step of administering to a patient in need thereof an effective amount of the compound of claim 1 or 2, or the composition of claim 3.

5. A compound according to claim 1, wherein $R_3$ is hydrogen.

6. A compound according to claim 2, wherein $R_4$ is OH or alkyloxy.

7. A compound according to claim 1 or 2, wherein a single bond is present between carbon atom numbers 7 and 8.

8. A compound according to claim 1 or 2, wherein $R_1$ is (cyclical saturated group)alkyl or alkenyl.

9. A compound according to claim 1 or 2, wherein $R_1$ is $C_2$-$C_6$-alkenyl or $C_3$-$C_{16}$-(cyclical saturated group)alkyl, where alkyl is $C_1$-$C_6$ alkyl.

10. A compound of formula (I),

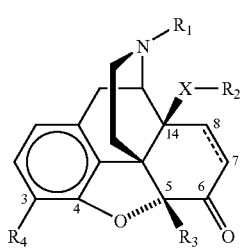

(I)

in which the substituents have the following significance:

$R_1$ is a $C_4$-$C_{16}$ cycloalkylalkyl, wherein the cycloalkyl is $C_3$-$C_{10}$ and the alkyl is $C_1$-$C_6$;

$R_2$: $C_4$-$C_6$-alkyl; $C_2$-$C_6$-alkenyl; $C_2$-$C_6$-alkinyl; $C_3$-$C_{16}$-(cyclical saturated group)alkyl, where alkyl is $C_1$-$C_6$; $C_4$-$C_{16}$-(cyclical saturated group)alkenyl, where alkenyl is $C_2$-$C_6$; $C_4$-$C_{16}$-(cyclical saturated group)alkinyl, where alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_3$-$C_6$-alkenoyl; $C_3$-$C_6$-alkinoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl;

$R_3$: $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$;

$R_4$: hydrogen; hydroxy; $C_1$-$C_6$-alkyloxy; $C_2$-$C_{10}$-alkyloxyalkoxy, where alkyloxy is $C_1C_4$ alkyloxy and alkoxy is $C_1$-$C_6$-alkyloxy; $C_2$-$C_6$-alkenyloxy; $C_2$-$C_6$-alkinyloxy; $C_3$-$C_{16}$-(cyclical saturated group)alkyloxy, where alkyl is $C_1$-$C_6$ alkyl; $C_4$-$C_{16}$-(cyclical saturated group)alkenyloxy, where alkenyl is $C_2$-$C_6$ alkenyl; $C_4$-$C_{16}$-(cyclical saturated group)alkinyloxy where alkinyl is $C_2$-$C_6$ alkinyl; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_3$-$C_6$-alkenoyloxy; $C_3$-$C_6$-alkinoyloxy; $C_7$-$C_{16}$-arylalkanoyloxy, where aryl is $C_6$-$C_{10}$-aryl and alkanoyloxy is $C_2$-$C_6$-alkanoyloxy; $C_9$-$C_{16}$-arylalkenoytoxy, where aryl is $C_6$-$C_{10}$-aryl and alkenoyloxy is $C_3$-$C_6$-alkenoyloxy; $C_9$-$C_{16}$-arylalkinoyloxy, where aryl is $C_6$-$C_{10}$-aryl and alkinoyloxy is $C_3$-$C_6$-alkinoyloxy;

X is oxygen;

wherein a single or double bond can be present between the carbon atoms of numbers 7 and 8, wherein alkyl, alkenyl and alkinyl can each be branched or unbranched, aryl can be unsubstituted or mono-, di- or trisubstituted, independently in each case, with hydroxy, halogen, nitro, cyano, thiocyanato, trifluoromethyl, $C_1$-$C_3$-alkyl, $C_1$-$C_3$-alkoxy, $CO_2H$, $CON_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino; $C_5$-$C_6$-cycloalkylamino, $(C_1$-$C_3$-alkanoyl)amido, SH, $SO_3H$, $SO_3(C_1$-$C_3$-alkyl), 802$(C_1$-$C_3$-alkyl), $SO(C_1$-$C_3$-alkyl), $C_1$-$C_3$-alkylthio or $C_1$-$C_3$-alkanoylthio, wherein -(cyclical saturated group) is either $C_3$-$C_{10}$cycloalkyl or a heterocyclic group with 2 to 9 carbon atoms, containing further one or more heteroatoms, with the exception of compounds where $R_1$ is cyclopropylinethyl and $XR_2$ is beuzyloxy, when $R_4$ is hydrogen or beuzyloxy, and with the further exception of compounds where $R_1$ is cyclopropylmethyl and $XR_2$ is benzyloxy, when $R_4$ is hydrogen, hydroxy or benzyloxy.

11. A pharmaceutical composition comprising (i) a pharmaceutically acceptable carrier and (ii) a compound of formula (I),

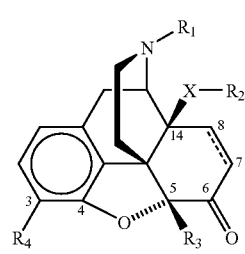

(I)

or a pharmaceutically acceptable addition salt thereof, in which the substituents have the following significance:

$R_1$ is a $C_4$-$C_{16}$ cycloalkylalkyl, wherein the cycloalkyl is $C_3$-$C_{10}$ and the alkyl is $C_1$-$C_6$;

$R_2$: $C_2$-$C_6$-alkyl; $C_2$-$C_6$-alkenyl; $C_2$-$C_6$-alkinyl; $C_3$-$C_{16}$-(cyclical saturated group)alkyl, where alkyl is C1-$C_6$; $C_4$-$C_{10}$-(cyclical saturated group)alkenyl, where alkenyl is $C_2$-$C_6$; $C_4$-$C_{16}$-(cyclical saturated group)alkinyl, where alkinyl is $C_2$-$C_6$; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-aklinyl; $C_3$-$C_6$-alkenoyl; $C_3$-$C_6$-alkinoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl;

$R_3$: $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$;

$R_4$: hydrogen; hydroxy; $C_1$-$C_6$-alkyloxy; $C_2$-$C_{10}$-alkyloxyalkoxy, where alkyloxy is $C_1$-$C_4$ alkyloxy and alkoxy is $C_1$-$C_6$-alkyloxy; $C_2$-$C_6$-alkenyloxy; $C_2$-$C_6$-alkinyloxy; $C_3$-$C_{16}$-(cyclical saturated group)alkyloxy, where alkyl is $C_1$-$C_6$ alkyl; $C_4$-$C_{16}$-(cyclical saturated group)alkenyloxy, where alkenyl is $C_2$-$C_6$ alkenyl; $C_4$-$C_{16}$-(cyclical saturated group)alkinyloxy where alkinyl is $C_2$-$C_6$ alkinyl; $C_7$-$C_{16}$-arylalkyloxy, where aryl is $C_6$-$C_{10}$-aryl and alkyl is $C_1$-$C_6$-alkyl; $C_8$-$C_{16}$-arylalkenyloxy, where aryl is $C_6$-$C_{10}$-aryl and alkenyl is $C_2$-$C_6$-alkenyl; $C_8$-$C_{16}$-arylalkinyloxy, where aryl is $C_6$-$C_{10}$-aryl and alkinyl is $C_2$-$C_6$-alkinyl; $C_1$-$C_6$-alkanoyloxy; $C_3$-$C_6$-alkenoyloxy; $C_3$-$C_6$-alkinoyloxy; $C_7$-$C_{16}$-arylalkanoyloxy, where aryl is $C_6$-$C_{10}$-aryl and alkanoyloxy is $C_2$-$C_6$-alkanoyloxy; $C_9$-$C_{16}$-arylalkenoyloxy, where aryl is $C_6$-$C_{10}$-aryl and alkenoyloxy is $C_3$-$C_6$-alkenoyloxy; $C_9$-$C_{16}$-arylalkinoyloxy, where aryl is $C_6$-$C_{10}$-aryl and alkinoyloxy is $C_3$-$C_6$-alkinoyloxy;

X is oxygen;

wherein a single or double bond can be present between the carbon atoms of numbers 7 and 8, wherein alkyl, alkenyl and alkinyl can each be branched or unbranched, aryl can be unsubstituted or mono-, di- or trisubstituted, independently in each case, with hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; ($C_1$-$C_3$-monoalkyl)amino, ($C_1$-$C_3$-dialkyl)amino; $C_5$-$C_6$-cycloalkylamino, ($C_1$-$C_3$-alkanoyl)amido, SH, $SO_3H$, $SO_3(C_1$-$C_3$-alkyl), $SO_2$($C_1$-$C_3$-alkyl), $SO(C_1$-$C_3$-alkyl), $C_1$-$C_3$-alkylthio or $C_1$-$C_3$-alkanoylthio, wherein -(cyclical saturated group) is either $C_3$-$C_{10}$-cycloalkyl or a heterocyclic group with 2 to 9 carbon atoms, containing further one or more hetero atoms, with the exception of compounds where $R_1$ is cyclopropylmethyl and $XR_2$ is benzyloxy, when $R_4$ is hydrogen or benzyloxy, and with the further exception of compounds where $R_1$ is cyclopropylmethyl and $XR_2$ is benzyloxy, when $R_4$ is hydrogen, hydroxy or benzyloxy.

12. A method of treating pain comprising the step of administering to a patient in need thereof an effective amount of the compound of claim 10 or the composition of claim 11.

13. A compound according to claim 10, wherein $R_4$ is OH.

14. A compound according to claim 10, wherein a single bond is present between carbon atom numbers 7 and 8.

* * * * *